US011279922B2

(12) United States Patent
Ponnapakkam et al.

(10) Patent No.: US 11,279,922 B2
(45) Date of Patent: *Mar. 22, 2022

(54) DELIVERY OF THERAPEUTIC AGENTS BY A COLLAGEN BINDING PROTEIN

(71) Applicants: THE BOARD OF TRUSTEES OF THE UNIVERSITY OF ARKANSAS, Little Rock, AR (US); The Kitasato Institute, Tokyo (JP); MONTEFIORE MEDICAL CENTER, New York, NY (US); NATIONAL UNIVERSITY CORPORATION KAGAWA UNIVERSITY, Kagawa (JP)

(72) Inventors: Tulasi Ponnapakkam, New York, NY (US); Sagaya Theresa Leena Philominathan, Cheshire, CT (US); Joshua Sakon, Fayetteville, AR (US); Ranjitha Katikaneni, New York, NY (US); Takaki Koide, Tokyo (JP); Osamu Matsushita, Kanagawa (JP); Robert C. Gensure, New York, NY (US); Nozomu Nishi, Kagawa (JP)

(73) Assignees: The Board of Trustees of the University of Arkansas, Little Rock, AR (US); The Kitasato Institute, Tokyo (JP); Montefiore Medical Center, New York, NY (US); National University Corporation Kagawa University, Kagawa (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/283,468

(22) Filed: Feb. 22, 2019

(65) Prior Publication Data
US 2019/0249163 A1 Aug. 15, 2019

Related U.S. Application Data

(60) Continuation of application No. 15/407,589, filed on Jan. 17, 2017, now Pat. No. 11,001,820, which is a
(Continued)

(51) Int. Cl.
*A61K 38/29* (2006.01)
*A61K 38/17* (2006.01)
(Continued)

(52) U.S. Cl.
CPC .............. *C12N 9/52* (2013.01); *A61K 8/4913* (2013.01); *A61K 8/64* (2013.01); *A61K 8/65* (2013.01); *A61K 8/66* (2013.01); *A61K 38/179* (2013.01); *A61K 38/18* (2013.01); *A61K 38/1808* (2013.01); *A61K 38/1825* (2013.01); *A61K 38/1841* (2013.01); *A61K 38/1858* (2013.01); *A61K 38/1866* (2013.01); *A61K 38/1875* (2013.01); *A61K 38/193* (2013.01); *A61K 38/27* (2013.01); *A61K 38/29* (2013.01); *A61K 38/30* (2013.01); *A61K 39/3955* (2013.01); *A61K 39/44* (2013.01); *A61K 47/64* (2017.08); *A61Q 7/00* (2013.01); *A61Q 7/02* (2013.01); *C07K 14/475* (2013.01); *C07K 14/485* (2013.01);
(Continued)

(58) Field of Classification Search
None
See application file for complete search history.

(56) References Cited

U.S. PATENT DOCUMENTS 5,914,126 A 6/1999 Li et al.
6,362,163 B1 3/2002 Gardella et al.
(Continued)

FOREIGN PATENT DOCUMENTS

EP 0207751 1/1987
JP 2002-58485 2/2002
(Continued)

OTHER PUBLICATIONS

Komarova, S.V., "Mathematical model of paracrine interactions between osteoclasts and osteoblasts predicts anabolic action of parathyroid hormone on bone," Endocrinology. (2005) 146(8):3589-95. Epub Apr. 28, 2005.
(Continued)

*Primary Examiner* — Nita M. Minnifield
(74) *Attorney, Agent, or Firm* — Quarles & Brady LLP

(57) ABSTRACT

Methods of delivering therapeutic agents by administering compositions including a bacterial collagen-binding polypeptide segment linked to the therapeutic agent to subjects in need of treatment with the therapeutic agent are provided. In these methods, the therapeutic agent is not a PTH/PTHrP receptor agonist or antagonist, basic fibroblast growth factor (bFGF) or epidermal growth factor (EGF). The bacterial collagen-binding polypeptide segment delivers the agent to sites of partially untwisted or under-twisted collagen. Methods of treating collagenopathies using a composition including a collagen-binding polypeptide and a PTH/PTHrP receptor agonist are also provided. In addition, methods of treating hyperparathyroidism, and hair loss using compositions comprising a collagen binding polypeptide and a PTH/PTHrP receptor agonist are provided. Finally, methods of reducing hair regrowth by administering a composition including a collagen binding polypeptide and a PTH/PTHrP receptor antagonist are provided.

19 Claims, 21 Drawing Sheets
Specification includes a Sequence Listing.

Related U.S. Application Data division of application No. 14/365,226, filed as application No. PCT/US2012/069831 on Dec. 14, 2012, now Pat. No. 9,579,273, application No. 16/283,468, which is a division of application No. 15/386,626, filed on Dec. 21, 2016, now Pat. No. 10,213,488, which is a division of application No. 14/378,067, filed as application No. PCT/US2013/025541 on Feb. 11, 2013, now Pat. No. 9,526,765, which is a continuation-in-part of application No. PCT/US2012/069831, filed on Dec. 14, 2012.

(60) Provisional application No. 61/570,620, filed on Dec. 14, 2011, provisional application No. 61/596,869, filed on Feb. 9, 2012.

(51) Int. Cl.

| | | |
|---|---|---|
| A61K 38/18 | (2006.01) | |
| A61K 38/19 | (2006.01) | |
| A61K 39/395 | (2006.01) | |
| C12N 9/52 | (2006.01) | |
| A61K 8/49 | (2006.01) | |
| A61K 8/65 | (2006.01) | |
| A61Q 7/00 | (2006.01) | |
| A61K 47/64 | (2017.01) | |
| A61K 8/64 | (2006.01) | |
| A61K 8/66 | (2006.01) | |
| A61K 38/30 | (2006.01) | |
| A61K 39/44 | (2006.01) | |
| A61Q 7/02 | (2006.01) | |
| A61K 38/27 | (2006.01) | |
| C07K 14/475 | (2006.01) | |
| C07K 14/485 | (2006.01) | |
| C07K 14/49 | (2006.01) | |
| C07K 14/495 | (2006.01) | |
| C07K 14/50 | (2006.01) | |
| C07K 14/51 | (2006.01) | |
| C07K 14/535 | (2006.01) | |
| C07K 14/61 | (2006.01) | |
| C07K 14/71 | (2006.01) | |
| C07K 16/18 | (2006.01) | |
| A61K 39/00 | (2006.01) | |
| A61K 38/00 | (2006.01) | |

(52) U.S. Cl.
CPC ............ *C07K 14/49* (2013.01); *C07K 14/495* (2013.01); *C07K 14/50* (2013.01); *C07K 14/51* (2013.01); *C07K 14/535* (2013.01); *C07K 14/61* (2013.01); *C07K 14/71* (2013.01); *C07K 16/18* (2013.01); *C12Y 304/24003* (2013.01); *A61K 38/00* (2013.01); *A61K 2039/505* (2013.01); *A61K 2039/6031* (2013.01); *A61K 2800/57* (2013.01); *C07K 2319/31* (2013.01); *C07K 2319/70* (2013.01); *C07K 2319/74* (2013.01)

(56) References Cited

U.S. PATENT DOCUMENTS

| | | |
|---|---|---|
| 8,450,273 B2 | 5/2013 | Sakon et al. |
| 8,617,543 B2 | 12/2013 | Huang et al. |
| 9,062,300 B2 | 6/2015 | Gensure et al. |
| 9,248,164 B2 | 2/2016 | Uchida et al. |
| 9,354,240 B2 | 5/2016 | Yamagata et al. |
| 9,526,765 B2 | 12/2016 | Ponnapakkam et al. |
| 9,528,099 B2 | 12/2016 | Gensure et al. |
| 9,579,273 B2 | 2/2017 | Ponnapakkam et al. |
| 9,757,435 B2 | 9/2017 | Herber |
| 10,111,983 B2 | 10/2018 | Shimp |
| 10,202,434 B2 * | 2/2019 | Gensure ............... A61P 19/00 |
| 10,213,488 B2 | 2/2019 | Ponnapakkam et al. |
| 10,358,471 B2 * | 7/2019 | Gensure ............... A61P 35/04 |
| 10,519,213 B2 * | 12/2019 | Gensure ............... A61K 8/64 |
| 2002/0102709 A1 | 8/2002 | Ishikawa et al. |
| 2002/0164719 A1 | 11/2002 | Hall et al. |
| 2003/0187232 A1 | 10/2003 | Hubbell et al. |
| 2004/0053368 A1 | 3/2004 | Ishikawa et al. |
| 2004/0220094 A1 | 11/2004 | Skinner et al. |
| 2005/0119183 A1 | 6/2005 | Wells et al. |
| 2005/0124537 A1 | 6/2005 | Kostemuik et al. |
| 2005/0180986 A1 | 8/2005 | Rich et al. |
| 2006/0014687 A1 | 1/2006 | Crine et al. |
| 2006/0257376 A1 | 11/2006 | Scadden et al. |
| 2008/0108562 A1 | 5/2008 | Riviere et al. |
| 2009/0305352 A1 | 12/2009 | Dai et al. |
| 2010/0129341 A1 | 5/2010 | Sakon et al. |
| 2010/0159564 A1 | 6/2010 | Dwulet et al. |
| 2013/0287759 A1 | 10/2013 | Muñoz Montano |
| 2013/0337017 A1 | 12/2013 | Gensure et al. |
| 2014/0377215 A1 | 12/2014 | Ponnapakkam et al. |
| 2015/0038423 A1 | 2/2015 | Ponnapakkam et al. |
| 2015/0284701 A1 | 10/2015 | Gensure et al. |
| 2016/0339078 A1 | 11/2016 | Hamill et al. |
| 2017/0101457 A1 | 4/2017 | Gensure et al. |
| 2017/0106093 A1 | 4/2017 | Ponnapakkam et al. |
| 2017/0204390 A1 | 7/2017 | Ponnapakkam et al. |
| 2018/0055918 A1 | 3/2018 | Herber |
| 2018/0140742 A1 | 5/2018 | Uchida et al. |

FOREIGN PATENT DOCUMENTS

| | | |
|---|---|---|
| JP | 2004-500838 | 1/2004 |
| JP | 2010-523671 | 7/2010 |
| WO | WO 2000006195 | 2/2000 |
| WO | WO 2000049159 | 8/2000 |
| WO | WO 2003052091 | 6/2003 |
| WO | WO 2004071543 | 8/2004 |
| WO | WO 2006072623 | 7/2006 |
| WO | WO 2008/124166 | 10/2008 |
| WO | WO 2009/014854 | 1/2009 |
| WO | WO 2010087397 | 8/2010 |
| WO | WO 2011142425 | 11/2011 |
| WO | WO 2012/124338 | 9/2012 |
| WO | WO 2012157339 | 11/2012 |
| WO | WO 2013/090770 | 6/2013 |
| WO | WO 2013/120060 | 8/2013 |
| WO | WO 2016/060252 | 4/2016 |

OTHER PUBLICATIONS

Kousteni, S. et al., "The cell biology of parathyroid hormone in osteoblasts," Curr Osteoporos. Rep. (2008) 6(2):72-6.

Kroll, M.H., "Parathyroid hormone temporal effects on bone formation and resorption," Bull Math Biol. (2000) 62(1):163-88.

Lemaire, V. et al., "Modeling the interactions between osteoblast and osteoclast activities in bone remodeling," J Theor Biol. (2004) 229(3):293-309.

Li, X. et al., "Determination of dual effects of parathyroid hormone on skeletal gene expression in vivo by microarray and network analysis," J Biol Chem. (2007) 282(45):33086-97. Epub Aug. 9, 2007.

Li, X. et al., "In vivo parathyroid hormone treatments and RNA isolation and analysis," Methods Mol Biol. (2008) 455:79-87.

Liu, J. et al., "Intermittent PTH administration: a novel therapy method for periodontitis-associated alveolar bone loss," Med Hypotheses. (2009) 72(3):294-6. Epub Nov. 30, 2008.

Locklin, R.M. et al., "Mediators of the biphasic responses of bone to intermittent and continuously administered parathyroid hormone," J Cell Biochem. (2003) 89(1):180-90.

Locus BAA06251 (GI 710023), Collagenase precursor from Clostridium histolyticum, Jan. 30, 2003. This amino acid sequence is disclosed in this application as SEQ ID No. 6. The sequence of residues 901-1021 of BAA06251 corresponds to the collagen binding domain included in the fusion protein of SEQ ID No. 1.

(56) References Cited

OTHER PUBLICATIONS

Locus EAW68494 (GI 119588900), Parathyroid hormone isoform from *Homo sapiens*, Dec. 18, 2006. Residues 64-147 of EAW68494 correspond to the PTH of SEQ ID No. 7.
Lotinun, S. et al., "Differential effects of intermittent and continuous administration of parathyroid hormone on bone histomorphometry and gene expression," Endocrine. (2002) 17(1):29-36.
Lotinun, S. et al., "Triazolopyrimidine (trapidil), a platelet-derived growth factor antagonist, inhibits parathyroid bone disease in an animal model for chronic hyperparathyroidism," Endocrinology. (2003) 144(5):2000-7.
Lumachi, F. et al., "Lumbar spine bone mineral density changes in patients with primary hyperparathyroidism according to age and gender," Ann N Y Acad Sci. (2007) 1117:362-6. Epub Jul. 26, 2007.
Ma, Y.L. et al., "Catabolic effects of continuous human PTH (1—38) in vivo is associated with sustained stimulation of RANKL and inhibition of osteoprotegerin and gene-associated bone formation," Endocrinology (2001) 142(9):4047-54.
Machado Do Reis, L. et al., "Accentuated osteoclastic response to parathyroid hormone undermines bone mass acquisition in osteonectin-null mice," Bone (2008) 43(2):264-73. Epub Apr. 13, 2008.
Malluche, H.H. et al., "Endogenous calcitonin does not protect against hyperparathyroid bone disease in renal failure," Miner. Electrolyte Metab. (1986) 12(2):113-8.
Malluche, H.H. et al., "Osteomalacia and hyperparathyroid bone disease in patients with nephrotic syndrome," J Clin Invest. (1979) 63(3):494-500.
Malluche, H.H. et al., "Influence of the parathyroid glands on bone metabolism," Eur J Clin Invest. (2006) 36(Suppl 2):23-33.
Malluche, H.H. et al., "Effects of long-term infusion of physiologic doses of 1-34 PTH on bone" Am J Physiol. (1982) 242(2):F197-201.
Masi, L. et al., "Molecular, biochemical and cellular biology of PTH anabolic action," J Endocrinol Invest. (2005) 28(8 Suppl):37-40.
Mathias, R. et al., "Renal bone disease in pediatric and young adult patients on hemodialysis in a children's hospital," J Am Soc Nephrol. (1993) 3(12):1938-46.
Matsushita, O. et al., "A study of the collagen-binding domain of a 116-kDa Clostridium histolyticum collagenase," J Biological Chem (1998) 273(6):3643-3648.
Matsushita, O. et al., "Gene duplication and multiplicity of C. Histolyticum collagenases," J. Bacteriol. (1999) 181:923-933.
Matsushita, O. et al., "Substrate recognition by the collagen-binding domain of Clostridium histolyticum class I collagenase," J of Biological Chem (2001) 276(12):8761-8770.
Matsushita, O., "Studies on the Clostridal Collagenases," Nippon Saikingaku Zasshi (1999) 54(4):753-761.
McCauley, L.K. et al., "PTH/PTHrP receptor is temporally regulated during osteoblast differentiation and is associated with collagen synthesis," J Cell Biochem (1996) 61:638-647.
McCauley, L.K. et al., "Proto-oncogene c-fos is transcriptionally regulated by parathyroid hormone (PTH) and PTH-related protein in a cyclic adenosine monophosphate-dependent manner in osteoblastic cells," Endocrinology (1997) 138(12):5427-33.
McCauley, L.K. et al., "Parathyroid hormone stimulates fra-2 expression in osteoblastic cells in vitro and in vivo," Endocrinology (2001) 142(5):1975-81.
Minisola, S. et al., "Trabecular bone mineral density in primary hyperparathyroidism: relationship to clinical presentation and biomarkers of skeletal turnover," Bone Miner. (1993) 20(2):113-23.
Minisola, S. et al., "Uneven deficits in vertebral bone density in postmenopausal patients with primary hyperparathyroidism as evaluated by posterior-anterior and lateral dual-energy absorptiometry," Osteoporos Int. (2002) 13(8):618-23.
Mitlak, B.H. et al., "Asymptomatic primary hyperparathyroidism," J Bone Miner Res. (1991) 6(Suppl 2):S103-10; discussion S121-4.
Miyachi, Y. et al., "Long-term safety and efficacy of high-concentration (20 mug/g) tacalcitol ointment in psoriasis vulgaris," Eur J Dermatol (2002) 12(5):463-468.
Morley, P. et al., "Anabolic effects of parathyroid hormone on bone," Trends Endocrinol. Metab. (1997) 8(6):225-31.
Morley, P. et al., "Parathyroid hormone: an anabolic treatment for osteoporosis," Curr Pharm Des. (2001) 7(8):671-87.
Murray, E.J. et al., "E64d, a membrane-permeable cysteine protease inhibitor, attenuates the effects of parathyroid hormone on osteoblasts in vitro," Metabolism (1997) 46(9):1090-4.
Nasu, M. et al., "Stimulatory effects of parathyroid hormone and 1,25-dihydroxyvitamin D3 on insulin-like growth factor-binding protein-5 mRNA expression in osteoblastic UMR-106 cells: the difference between transient and continuous treatments," FEBS Lett. (1997) 409(1):63-6.
Neer, R.M. et al., "Effect of parathyroid hormone (1-34) on fractures and bone mineral density in postmenopausal women with osteoporosis," N. Engl. J. Med. (2001) 344(19):1434-1441.
Nemeth, E.F., "Pharmacological regulation of parathyroid hormone secretion," Curr Pharm. Des. (2002) 8(23):2077-87.
Nilsson, P., "Bone disease in renal failure. Clinical and histomorphometric studies," Scand J Urol Nephrol Suppl. (1984) 84:1-68.
Nishi, N. et al., "Collagen-binding growth factors: Production and characterization of functional fusion proteins having a collagen-binding domain," PNAS (1998) 95(12):7018-7023.
Nomura, R. et al., "Contribution of the Collagen-Binding Proteins of *Streptococcus mutans* to Bacterial Colonization of Inflamed Dental Pulp" PLoS One (2016) 11(7):e0159613.
O'Brien, C.A. et al., "IL-6 is not required for parathyroid hormone stimulation of RANKL expression, osteoclast formation, and bone loss in mice," Am J Physiol Endocrinol Metab. (2005) 289(5):E784-93. Epub Jun. 14, 2005.
Okazaki, R., "Parathyroid hormone—its mechanisms of action and issues on clinical application," Clin Calcium. (2005) 15(5):845-51.
Olgaard, K. et al., "Can hyperparathyroid bone disease be arrested or reversed?," Clin J Am Soc Nephrol. (2006) l(3):367-73. Epub Mar. 29, 2006.
Onyia, J.E. et al., "Molecular profile of catabolic versus anabolic treatment regimens of parathyroid hormone (PTH) in rat bone: an analysis by DNA microarray," J Cell Biochem. (2005) 95(2):403-18.
Owens, R.J. et al., "Mapping the collagen-binding site of human fibronectin by expression in *Escherichia coli*," The EMBO Journal (1986) 5(11)2825-2830.
Paillard, M. et al., "Determinants of parathormone secretion in primary hyperparathyroidism," Horm Res. (1989) 32(1-3):89-92.
Parfitt, A.M., "The actions of parathyroid hormone on bone: relation to bone remodeling and turnover, calcium homeostasis, and metabolic bone disease. Part IV of IV parts: The state of the bones in uremic hyperaparathyroidism—the mechanisms of skeletal resistance to PTH in renal failure and pseudohypoparathyroidism and the role of PTH in osteoporosis, osteopetrosis, and osteofluorosis," Metabolism. (1976) 25(10):1157-88.
Parfitt, A.M. et al., "Hypercalcemia due to constitutive activity of the parathyroid hormone (PTH)/PTH-related peptide receptor: comparison with primary hyperparathyroidism," J Clin Endocrinol Metab. (1996) 81(10):3584-8.
Peters, E.M.J. et al., "A new strategy for modulating chemotherapy-induced alopecia, using PTH/PTHrP receptor agonist and antagonist," J Invest Dermatol (2001) 117(2):173-178.
Pettway, et al., "Anabolic actions of PTH (1-34): Use of a novel tissue engineering model to investigate temporal effects on bone," Bone (2005) 36(6):959-970.
Phelps, E. et al., "Parathyroid hormone induces receptor activity modifying protein-3 (RAMP3) expression primarily via 3',5'-cyclic adenosine monophosphate signaling in osteoblasts," Calcif Tissue Int. (2005) 77(2):96-103. Epub Aug. 11, 2005.
Philominathan et al., "Unidirectional binding of Clostridial Collageanse to Triple Helical Substrates," Journal of Biological Chemistry (2009) 284(16):10868-10876.
Philominathan et al., "Bacterial collagen-binding domain targets undertwisted regions of collagen," Protein Sci. (2012) 21(10):1554-65.
Pirih, F.Q. et al., "Parathyroid hormone induces the NR4A family of nuclear orphan receptors in vivo," Biochem Biophys Res Commun. (2005) 332(2):494-503.

(56) References Cited

OTHER PUBLICATIONS

Podbesek, R. et al., "Effects of two treatment regimes with synthetic human parathyroid hormone fragment on bone formation and the tissue balance of trabecular bone in greyhounds," Endocrinology (1983) 112(3):1000-6.
Ponnapakkam, T. et al., "A fusion protein of parathyroid hormone (PTH) and a collagen binding domain shows superior efficacy and longer duration of action compared to PTH(1-34) as an anabolic bone agent in normal female mice," Bone (2009) 44:S35-S36.
Ponnapakkam, T., et al., "Monthly administration of a novel PTH-collagen binding domain fusion protein is anabolic in mice," Calcif Tissue Int.2011;88:511-520.
Ponnapakkam, T. et al., "A Single Injection of the Anabolic Bone Agent, Parathyroid Hormone-Collagen Binding Domain (PTH-CBD), Results in Sustained Increases in Bone Mineral Density for up to 12 Months in Normal Female Mice" Calcified Tissue (2012) 91(30:196-203.
Poole, K.E. et al., "Parathyroid hormone—a bone anabolic and catabolic agent," Curr Opin Pharmacol. (2005) 5(6):612-7. Epub Sep. 21, 2005.
Potter, L.K. et al., "Response to continuous and pulsatile PTH dosing: a mathematical model for parathyroid hormone receptor kinetics," Bone (2005) 37(2):159-169.
Potts, J.T., "Parathyroid hormone: past and present," J Endocronology (2005) 187:311-325.
Qin, L. et al., "Parathyroid hormone: a double-edged sword for bone metabolism," Trends Endocrinol Metab. (2004) 15(2):60-5.
Rattanakul, C. et al., "Modeling of bone formation and resorption mediated by parathyroid hormone: response to estrogen/PTH therapy" Biosystems (2003) 70(1):55-72.
Richardson, M.L. et al., "Bone mineral changes in primary hyperparathyroidism," Skeletal Radiol. (1986) 15(2):85-95.
Rickard, D.J. et al., "Intermittent treatment with parathyroid hormone (PTH) as well as a non-peptide small molecule agonist of the PTH1 receptor inhibits adipocyte differentiation in human bone marrow stromal cells," Bone (2006) 39(6):1361-1372. Epub Aug. 10, 2006.
Rixon, R.H. et al., "Parathyroid hormone fragments may stimulate bone growth in ovariectomized rats by activating adenylyl cyclase," J Bone Miner Res. (1994) 9(8):1179-89.
Robinson, J.A. et al., "Identification of a PTH regulated gene selectively induced in vivo during PTH-mediated bone formation," J Cell Biochem. (2006) 98(5):1203-20.
Rosen, C.J., "The cellular and clinical parameters of anabolic therapy for osteoporosis," Crit Rev Eukaryot Gene Expr. (2003) 13(1):25-38.
Rubin, M.R. et al., "The potential of parathyroid hormone as a therapy for osteoporosis," Int J Fertil Womens Med. (2002) 47(3):103-15.
Rubin, M. et al., "The anabolic effects of parathyroid hormone therapy," Osteoporosis International (2002) 13(4):267-277.
Rubin, M.R. et al., "The anabolic effects of parathyroid hormone therapy," Clin Geriatr Med. (2003) 19(2):415-32.
Safer, J.D. et al., "A topical parathyroid hormone/parathyroid hormone-related peptide receptor antagonist stimulates hair growth in mice," Endocrinology (2007)148:1167-1170.
Schaefer, F., "Pulsatile parathyroid hormone secretion in health and disease," Novartis Found Symp. (2000) 227:225-39; discussion 239-43.
Schilli, M.B. et al., "Control of hair growth with parathyroid hormone (7-34)," J Invest Dermatol (1997) 108:928-932.
Schluter, K.-D. et al., "A N-terminal PTHrP peptide fragment void of a PTH/PTHrP-receptor binding domain activates cardiac ETA receptors," British Journal of Pharmacology (2001) 132:427-432.
Schmitt, C.P. et al., "Intermittent administration of parathyroid hormone (1-37) improves growth and bone mineral density in uremic rats," Kidney Int. (2000) 57(4):1484-92.
Schmitt, C.P. et al., "Structural organization and biological relevance of oscillatory parathyroid hormone secretion," Pediatr Nephrol. (2005) 20(3):346-51. Epub Feb. 8, 2005.

Schneider, A. et al., "Skeletal homeostasis in tissue-engineered bone," J Orthop Res. (2003) 21(5):859-64.
Seeman, E. et al., "Reconstructing the skeleton with intermittent parathyroid hormone," Trends Endocrinol Metab. (2001) 12(7):281-3.
Sekiguchi, H. et al., "Acceleration of bone formation during fracture healing by poly(pro-hyp-gly)10 and basic fibroblast growth factor containing polycystic kidney disease and collagen-binding domains from Clostridium histolyticum collagenase" J. Biomed Mater Res A. (2016) 104(6):1372-1378.
Shen, V. et al., "Skeletal effects of parathyroid hormone infusion in ovariectomized rats with or without estrogen repletion," J Bone Miner Res. (2000) 15(4):740-6.
Shin, H., et al. Efficacy of Interventions for Prtevention of Chemotherapy-Induced Alopecia: A systematic review and meta-analysis. International Journal of Cancer. 2015. 136: E442-E454.
Shinoda, Y. et al., "Mechanisms underlying catabolic and anabolic functions of parathyroid hormone on bone by combination of culture systems of mouse cells," J. of Cellular Biology (2010) 109(4):755-63.
Silver, J. et al., "Harnessing the parathyroids to create stronger bones," Curr Opin Nephrol Hypertens. (2004) 13(4):471-6.
Silverberg, S.J. et al., "Skeletal disease in primary hyperparathyroidism," J Bone Miner Res., (1989) 4(3):283-91.
Skripitz, R. et al., "Parathyroid hormone—a drug for orthopedic surgery?," Acta Orthop Scand. (2004) 75(6):654-62.
Skripitz, R. et al., "Stimulation of implant fixation by parathyroid hormone (I-34)—A histomorphometric comparison of PMMA cement and stainless steel," J Orthop Res. (2005) 23(6): 1266-70. Epub Jun. 16, 2005.
Smajilovic, S. et al., "Effect of intermittent versus continuous parathyroid hormone in the cardiovascular system of rats," Open Cardiovasc. Med. J. (2010) 4:110-6.
Spurney, R.F. et al., "Anabolic effects of a G protein-coupled receptor kinase inhibitor expressed in osteoblasts," J Clin Invest. (2002) 109(10):1361-71.
Stewart, A.F., "PTHrP(1-36) as a skeletal anabolic agent for the treatment of osteoporosis," Bone (1996) 19(4):303-306.
Stracke, S. et al., "Long-term outcome after total parathyroidectomy for the management of secondary hyperparathyroidism," Nephron Clin Pract. (2009) 111(2):c102-9. Epub Jan. 13, 2009.
Strewler, G.J., "Local and systemic control of the osteoblast," J. of Clin. Invest. (2001) 107:271-272.
Suttamanatwong, S. et al., "Regulation of matrix Gla protein by parathyroid hormone in MC3T3-E1 osteoblast-like cells involves protein kinase A and extracellular signal-regulated kinase pathways," J Cell Biochem. (2007) 102(2):496-505.
Suttamanatwong, S. et al., "Sp proteins and Runx2 mediate regulation of matrix gla protein (MGP) expression by parathyroid hormone," J Cell Biochem. (2009) 107(2):284-92.
Suzuki, A. et al., "PTH/cAMP/PKA signaling facilitates canonical Wnt signaling via inactivation of glycogen synthase kinase-3beta in osteoblastic Saos-2 cells," J Cell Biochem. (2008) 104(1):304-17.
Abdelhadi, M. et al., "Bone mineral recovery after parathyroidectomy in patients with primary and renal hyperparathyroidism," J Clin Endocrinol Metab. (1998) 83(11):3845-51.
Abe, Y. et al., "Enhancement of graft bone healing by intermittent administration of human parathyroid hormone (1-34) in a rat spinal arthrodesis model," Bone (2007) 41(5):775-785.
Abshirini, H. et al., "Pathologic fractures: a neglected clinical feature of parathyroid adenoma," Case (2010) p. 357029. Epub Nov. 29, 2010.
Akimoto, M. et al., "Effects of CB-VEGF-A injection in rat flap models for improved survival," (2013) Plast. Reconstr. Surg. 131(4):717-725.
Aleksyniene, R. et al., "Parathyroid hormone—possible future drug for orthopedic surgery," Medicina (Kaunas) (2004) 40(9):842-9.
Andrade, M.C., et al., "Bone mineral density and bone histomorphometry in children on long-term dialysis," Pediatr Nephrol. (2007) 22(10):1767-72. Epub Aug. 7, 2007.
Barros, S.P., et al., "Parathyroid hormone protects against periodontitis-associated bone loss," J Dent Res. (2003) 82(10):791-5.

(56) References Cited

OTHER PUBLICATIONS

Bauer, R., et al., "Structural comparison of ColH and ColG collagen-binding domains from Clostridium histolyticum," (2013) *Journal of Bacteriology*, 195(2), 318-327.

Bedi, B., et al., "Inhibition of antigen presentation and T cell costimulation blocks PTH-induced bone loss," Ann N Y Acad Sci. (2010) 1192:215-21.

Belinsky, G.S. et al., "Direct measurement of hormone-induced acidification in intact bone," J Bone Miner Res., (2000) 15(3):550-6.

Bellido, T., et al., "Chronic elevation of parathyroid hormone in mice reduces expression of sclerostin by osteocytes: a novel mechanism for hormonal control of osteoblastogenesis," Endocrinology (2005) 146(11):4577-83. Epub Aug. 4, 2005.

Bergenstock, M.K. et al., "Parathyroid hormone stimulation of noncanonical Wnt signaling in bone," Ann N Y Acad Sci. (2007) 1116:354-9.

Bergwitz, C. et al., "Rapid desensitization of parathyroid hormone dependent adenylate cyclase in perifused human osteosarcoma cells (SaOS-2)," Biochem Biophys Acta. (1994) 1222(3):447-56.

Bianchi, E.N. et al., "Beta-arrestin2, regulates parathyroid hormone effects on a p38 MAPK and NFkappaB gene expression network in osteoblasts" Bone (2009) 45(4):716-25. Epub Jun. 25, 2009.

Bilezikian, J.P. et al., "Asymptomatic primary hyperparathyroidism: new issues and new questions—bridging the past with the future," J Bone Miner Res. (2002) 17(Suppl 2):N57-67.

Bilezikian, J.P. et al., "Characterization and evaluation of asymptomatic primary hyperparathyroidism," J Bone Miner Res. (1991) 6(Suppl 2):S85-9; discussion S121-4.

Blachowicz, A. et al., "Serum 1-84 and 7-84 parathyroid hormone concentrations and bone in patients with primary hyperparathyroidism," Langenbecks Arch Surg. (2008) 393(5):709-13. Epub Jul. 11, 2008.

Buargub, M.A. et al., "Prevalence and pattern of renal osteodystrophy in chronic hemodialysis patients: a cross sectional study of 103 patients," Saudi J Kidney Dis Transpl. (2006) 17(3):401-7.

Calvi, L.M. et al., "Activated parathyroid hormone/parathyroid hormone-related protein receptor in osteoblastic cells differentially affects cortical and trabecular bone," J. Clin. Invest. (2001)107:277-286.

Calvi, L.M. et al., "Osteoblastic cells regulate the haematopoietic stem cell niche," Nature (2003) 425:841-846.

Canalis, E., "Effect of hormones and growth factors on alkaline phosphatase activity and collagen synthesis in cultured rat calvariae," Metabolism (1983) 32(1):14-20.

Canalis, E. et al., "Insulin-like growth factor I mediates selective anabolic effects of parathyroid hormone in bone cultures," J Clin Invest. (1989) 83(1):60-5.

Carter, P.H. et al., "Selective and Nonselective Inverse Agonists for Constitutively Active Type-1 Parathyroid Hormone Receptors: Evidence for Altered Receptor Conformations," Endocrinology (2001) 142(4):1534-1545.

Chan, H.W. et al., "Prospective study on dialysis patients after total parathyroidectomy without autoimplant," Nephrology (2009) 15(4):441-7.

Chen, B. et al., "Homogeneous osteogenesis and bone regeneration by demineralized bone matrix loading with collagen-targeting bone morphogenetic protein-2," Biomaterials (2007) 28:1027-1035.

Chen, Q. et al., "Effects of an excess and a deficiency of endogenous parathyroid hormone on volumetric bone mineral density and bone geometry determined by peripheral quantitative computed tomography in female subjects," J Clin Endocrinol Metab. (2003) 88(10):4655-8.

Cherian, P.P. et al., "Role of gap junction, hemichannels, and connexin 43 in mineralizing in response to intermittent and continuous application of parathyroid hormone," Cell Commun Adhes. (2008) 15(1):43-54.

Chevalley, T. et al., "Bone and hormones. Effects of parathyroid hormone on the bone," Presse Med. (1999) 28(10):547-53.

Cohen, A. et al., "Osteoporosis in adult survivors of adolescent cardiac transplantation may be related to hyperparathyroidism, mild renal insufficiency, and increased bone turnover," J Heart Lung Transplant. (2005) 24(6):696-702.

Compston, J.E., "Skeletal actions of intermittent parathyroid hormone: effects on bone remodelling and structure," Bone (2007) 40(6):1447-1452.

Cormier, C., "Parathyroid hormone in osteoporosis," Presse Med. (2006) 35(3 Pt 2):495-501.

Corsi, A. et al., "Osteomalacic and hyperparathyroid changes in fibrous dysplasia of bone: core biopsy studies and clinical correlations," J Bone Miner Res. (2003) 18(7):1235-46.

Cosman, F., "Parathyroid hormone treatment for osteoporosis," Current Opinion in Endocrinology, Diabetes & Obesity (2008) 15:495-501.

Cundy, T. et al., "Hyperparathyroid bone disease in chronic renal failure," Ulster Med J. (1985) 54(Suppl):S34-43.

Datta, N.S. et al., "Distinct roles for mitogen-activated protein kinase phosphatase-1 (MKP-1) and ERK-MAPK in PTH1R signaling during osteoblast proliferation and differentiation," Cell (2010) 22(3):457-66. Epub.

Deal, C., "The use of intermittent human parathyroid hormone as a treatment for osteoporosis," Curr Rheumatol Rep. (2004) 6(1):49-58.

Demiralp, B. et al., "Anabolic actions of parathyroid hormone during bone growth are dependent on c-fos," Endocrinology (2002) 143(10):4038-47.

Dobnig, H. et al., "The effects of programmed administration of human parathyroid hormone fragment (1-34) on bone histomorphometry and serum chemistry in rats," Endocrinology (1997) 138(11):4607-12.

Drake, M.T. et al., "Parathyroid hormone increases the expression of receptors for epidermal growth factor in UMR 106-01 cells," Endocrinology (1994) 134(4):1733-7.

Endo, K. et al., "1,25-dihydroxyvitamin D3 as well as its analogue OCT lower blood calcium through inhibition of bone resorption in hypercalcemic rats with continuous parathyroid hormone-related peptide infusion," J Bone Miner Res. (2000) 15(1):175-81.

Etoh, M. et al., "Repetition of continuous PTH treatments followed by periodic withdrawals exerts anabolic effects on rat bone," J Bone Miner Metab. (2010) 28(6):641-649.

Farhanigan, M.E., et al. Treatment of Alopecia Areata in the United States: A Retrospective Cross-Sectional Study.J Drugs Dermatology. 2015 14(9):1012-4.

Fitzpatrick, L.A. et al., "Acute primary hyperparathyroidism," Am J Med. (1987) 82(2):275-82.

Fleming, A. et al., "High-throughput in vivo screening for bone anabolic compounds with zebrafish," J Biomol Screen. (2005) 10(8):823-31. Epub Oct. 18, 2005.

Fouda, M.A., "Primary hyperparathyroidism: King Khalid University Hospital Experience," Ann Saudi Med. (1999) 19(2):110-5.

Fox, J. et al., "Effects of daily treatment with parathyroid hormone 1-84 for 16 months on density, architecture and biomechanical properties of cortical bone in adult ovariectomized rhesus monkeys," Bone (2007) 41(3):321-330.

Fraher, L.J. et al., "Comparison of the biochemical responses to human parathyroid hormone-(1-31)NH2 and hPTH-(1-34) in healthy humans," J Clin Endocrinol Metab. (1999) 84(8):2739-43.

Frolik, C.A et al., "Anabolic and catabolic bone effects of human parathyroid hormone (1-34) are predicted by duration of hormone exposure," Bone (2003) 33(3):372-379.

Fujita, T., "Parathyroid hormone in the treatment of osteoporosis," BioDrugs (2001) 15(11):721-728.

Fukayama, S. et al., "New insights into interactions between the human PTH/PTHrP receptor and agonist/antagonist binding," Am. J. Physiol. Endocrinol. Metab. (1998) 274:297-303.

Gao, Y. et al., "T cells potentiate PTH-induced cortical bone loss through CD40L signaling," Cell Metab. (2008) 8(2):132-45.

Gardella, T.J. et al., "Converting Parathyroid Hormone-related Peptide (PTHrP) into a Potent PTH-2 Receptor Agonist," J. of Biological Chemistry, (1996) 271(33):19888-19893.

(56) References Cited

OTHER PUBLICATIONS

Gensure, R.C. et al., "Parathyroid hormone and parathyroid hormone-related peptide, and their receptors," Biochem Biophys Res Commun. (2005) 328(3):666-78.
Gensure, R.C. et al., "Parathyroid hormone without parathyroid glands," Endocrinology (2005) 146(2):544-546.
Gensure, R.C. et al., "Parathyroid hormone-related peptide and the hair cycle—is it the agonists or the antagonists that cause hair growth?" (2014) Experimental Dermatology, 23(12):865-867.
Gevers, E.F.et al., "Bone marrow adipocytes: a neglected target tissue for growth hormone," Endocrinology (2002) 143(10):4065-73.
Goltzman, D., "Studies on the mechanisms of the skeletal anabolic action of endogenous and exogenous parathyroid hormone," Arch Biochem Biophys. (2008) 473(2):218-24. Epub Mar. 10, 2008.
Gopalakrishnan, R. et al., "Role of matrix Gla protein in parathyroid hormone inhibition of osteoblast mineralization," Cells Tissues Organs (2005) 181(3-4):166-75.
Gosavi, A. et al., "An unusual presentation of parathyroid adenoma—a case report," Indian J Pathol Microbiol. (2005) 48(2):208-10.
Gu, W.X. et al., "Mutual up-regulation of thyroid hormone and parathyroid hormone receptors in rat osteoblastic osteosarcoma 17/2.8 cells," Endocrinology (2001) 142(1):157-64.
Hall, A.K. et al., "The effects of parathyroid hormone on osteoblast-like cells from embryonic chick calvaria," Acta Endocrinol (Copenh). (1985) 108(2):217-23.
Han, B. et al., "Collagen-targeted BMP3 fusion proteins arrayed on collagen matrices or porous ceramics impregnated with Type I collagen enhance osteogenesis in a rat cranial defect model," J Orthopaedic Research (2002) 20:747-755.
Headley, C.M., "Hungry bone syndrome following parathyroidectomy," Anna J., (1998) 25(3):283-9; quiz 290-1.
Heath, H., 3rd, "Clinical spectrum of primary hyperparathyroidism: evolution with changes in medical practice and technology," J Bone Miner Res. (1991) 6(Suppl 2):S63-70; discussion S83-4.
Hoare, S.R. et al., "Specificity and stability of a new PTH1 receptor antagonist, mouse TIP(7-39)," Peptides (2002) 23(5):989-998.
Hock, J.M. et al., "Human parathyroid hormone-(1-34) increases bone mass in ovariectomized and orchidectomized rats," Endocrinology (1988) 122(6):2899-2904.
Hock, J.M. et al., "Effects of continuous and intermittent administration and inhibition of resorption on the anabolic response of bone to parathyroid hormone," J Bone Miner Res. (1992) 7(1):65-72.
Holick, M.F. et al., "Topical PTH (1-34) is a novel, safe and effective treatment for psoriasis: a randomized self-controlled trial and an open trial," (2003) British J. Dermatology 149:370-376.
Homme, M. et al., "Differential regulation of RGS-2 by constant and oscillating PTH concentrations," Calcif Tissue Int. (2009) 84(4):305-12. Epub Feb. 20, 2009.
Horwitz, M.J. et al., "Parathyroid hormone-related protein for the treatment of postmenopausal osteoporosis: defining the maximal tolerable dose," J Clin Endocrinol Metab. (2010) 95(3):1279-87.
Horwitz, M.J. et al., "Continuous PTH and PTHrP infusion causes suppression of bone formation and discordant effects on 1,25(OH)2 vitamin D," J Bone Miner Res. (2005) 20(10):1792-803. Epub Jun. 6, 2005.
Hruska, K.A. et al., "Regulation of skeletal remodeling by parathyroid hormone," Contrib Nephrol. (1991) 91:38-42.
Iida-Klein, A. et al., "Short-term continuous infusion of human parathyroid hormone 1-34 fragment is catabolic with decreased trabecular connectivity density accompanied by hypercalcemia in C57BL/J6 mice," J Endocrinol. (2005) 186(3):549-57.
Ishii, H. et al., "Daily intermittent decreases in serum levels of parathyroid hormone have an anabolic-like action on the bones of uremic rats with low-tumover bone and osteomalacia," Bone (2000) 26(2):175-82.
Ishikawa, T. et al., "Delivery of a growth factor fusion protein having collagen-binding activity to wound tissues," Artif. Organs (2003) 27(2):147-154.
Ishikawa, T. et al., "Production of a biologically active epidermal growth factor fusion protein with high collagen affinity," J. Biochem. (2001) 129(4)627-633.
Ishizuya, T. et al., "Parathyroid hormone exerts disparate effects on osteoblast differentiation depending on exposure time in rat osteoblastic cells," J Clin Invest. (1997) 99(12):2961-70.
Ito, M., "Parathyroid hormone and bone quality," Clin Calcium. (2005) 15(12):31-7.
Ito, M., "Parathyroid and bone: Effect of parathyroid hormone on bone quality," Clin Calcium. (2007) 17(12):1858-64.
Jansen, P.L. et al., "Hernia disease and collagen gene regulation: are there clues for intervention?" Hernia (2006) 10:486-491.
Jeon, E. et al., "Engineering and application of collagen-binding fibroblast growth factor 2 for sustained release," (2013) J. of Biomed. Materials Research: Part A.
Jilka, R.L., "Molecular and cellular mechanisms of the anabolic effect of intermittent PTH," Bone (2007) 40(6):1434-1446. Epub Apr. 6, 2007.
Jilka, R.L. et al., "Continuous elevation of PTH increases the number of osteoblasts via both osteoclast-dependent and -independent mechanisms," J Bone Miner Res. (2010) 25(11):2427-37.
Kaji, H., "Parathyroid and bone: Effects of parathyroid hormone on bone resorption and formation: differences between intermittent and continuous treatment," Clin Calcium., (2007) 17(12):1836-42.
Katikaneni et al., "Treatment for chemotherapy-induced alopecia in mice using parathyroid hormone agonists and antagonists linked to coolagen binding domain," Int. J. Cancer (2012) 131(5):E813-821.
Katikaneni et al., "Therapy for alopecia areata in mice using parathyroid hormone agonists and antagonists, linked to a collagen-binding domain," J. of Investigative Dermatology Symposium Proceedings, (2013) 16(1):S61-S62.
Katikaneni R., et al. Parathyroid hormone linked to a collagen binding domain (PTH-CBD) promotes hair growth in a mouse model of chemotherqapy-induced alopecia in a dose-dependent manner. Anticancer Drugs. 2014. 25(7): 819-825.
Katikaneni, R. et al. Treatment and Prevention of Chemotherapy-induced alopecia with PTH-CBD, a collagen targeted parathyroid hormone analog, in a non-depilated mouse model. Anticancer Drugs. 2014. 25(1): 30-38.
Katikaneni, R. et al. Therapy for alopecia Areata in Mice by Stimulating the Hair Cycle with Parathyroid Hormone Agonists Linked to a Collagen-Binding Domain. The Journal of Investigative Dermatology Symposium. 2015. 17: 13-15.
Kaye, M. et al., "Elective total parathyroidectomy without autotransplant in end-stage renal disease," Kidney Int. (1989) 35(6):1390-9.
Khan, A. et al., "Primary hyperparathyroidism: pathophysiology and impact on bone," Cmaj. (2000) 163(2):184-7.
Kido, S. et al., "Mechanism of PTH actions on bone," Clin Calcium. (2003) 13(1):14-8.
Kistler, H., "Primary hyperparathyroidism: An analysis of 152 patients with special references to acute life threatening complications (acute parathyroidism)," Schweiz Med Wochenschr. (1976) 106(Suppl 3):1-61.
Kitazawa, R. et al., "Effects of continuous infusion of parathyroid hormone and parathyroid hormone-related peptide on rat bone in vivo: comparative study by histomorphometry," Bone Miner. (1991) 12(3):157-66.
Klempa, I., "Treatment of secondary and tertiary hyperparathyroidism—surgical viewpoints," Chirurg. (1999) 70(10):1089-101.
Koh, A.J. et al., "3',5'-Cyclic adenosine monophosphate activation in osteoblastic cells: effects on parathyroid hormone-1 receptors and osteoblastic differentiation in vitro," Endocrinology (1999) 140(7):3154-62.
Swarthout, J.T. et al., "Parathyroid hormone-dependent signaling pathways regulating genes in bone cells," Gene (2002) 282(1-2):1-17.
Swarthout, J.T. et al., "Stimulation of extracellular signal-regulated kinases and proliferation in rat osteoblastic cells by parathyroid hormone is protein kinase C-dependent," J Biol Chem. (2001) 276(10):7586-92. Epub Dec. 6, 2000.
Takada, H. et al., "Response of parathyroid hormone to anaerobic exercise in adolescent female athletes," Acta Paediatr Jpn. (1998) 40(1):73-7.

(56) References Cited

OTHER PUBLICATIONS

Takasu, H. et al., "Dual signaling and ligand selectivity of the human PTH/PTHrP receptor," J Bone Miner Res. (1999) 14(1):11-20.
Talmage, R.V. et al., "Calcium homeostasis: reassessment of the actions of parathyroid hormone," Gen Comp Endocrinol. (2008) 156(1):1-8. Epub Nov. 12, 2007.
Tam, C.S. et al., "Parathyroid hormone stimulates the bone apposition rate independently of its resorptive action: differential effects of intermittent and continuous administration," Endocrinology (1982) 110(2):506-12.
Tawfeek, H. et al., "Disruption of PTH receptor 1 in T cells protects against PTH-induced bone loss," PLoS (2010) 5(8):e12290.
Tokumoto, M. et al., "Parathyroid cell growth in patients with advanced secondary hyperparathyroidism: vitamin D receptor, calcium sensing receptor, and cell cycle regulating factors," Ther Apher Dial. (2005) 9(Suppl 1):S27-34.
Tollin, S.R. et al., "Serial changes in bone mineral density and bone turnover after correction of secondary hyperparathyroidism in a patient with pseudohypoparathyroidism type Ib," J Bone Miner Res. (2000) 15(7):1412-6.
Toyoshima, T. et al., "Collagen-binding domain of a Clostridium histolyticum collagenase exhibits a broad substrate spectrum both in vitro and in vivo," Connective Tissue Research (2001) 42(4):281-290.
Uzawa, T. et al., "Comparison of the effects of intermittent and continuous administration of human parathyroid hormone(1-34) on rat bone," Bone (1995) 16(4):477-84.
Vanstone, M.B. et al., "Rapid correction of bone mass after parathyroidectomy in an adolescent with primary hyperparathyroidism," J. Clin Endocrinol. Metab. (2011) 96(2): E347-50. Epub Nov. 24, 2010.
Wan, Q. et al., "Intra-articular injection of parathyroid hormone in the temporomandibular joint as a novel therapy for mandibular asymmetry," Med Hypotheses (2009) 74(4):685-7.
Wang, C.A. et al., "Natural history of parathyroid carcinoma. Diagnosis, treatment, and results," Am J Surg. (1985) 149(4):522-7.
Wang, Y. et al., "A theoretical model for simulating effect of parathyroid hormone on bone metabolism at cellular level," Mol Cell Biomech. (2009) 6(2):101-12.
Wang, Y. et al., "Gender differences in the response of CD-1 mouse bone to parathyroid hormone: potential role of IGF-I," J Endocrinol. (2006) 189(2):279-87.
Watson, P.H. et al., "Enhanced osteoblast development after continuous infusion of hPTH(1-84) in the rat," Bone (1999) 24(2):89-94.
Weir, E.C. et al., "Synthetic parathyroid hormone-like protein (1-74) is anabolic for bone in vivo," Calcif Tissue Int. (1992) 51(1):30-4.
Whitfield, J.F., "Taming Psoriatic Keratinocytes-PTHs' uses go up another notch," J. Cell. Biochem. (2004) 93:251-256.
Wilson, J.J. et al., "A bacterial collagen-binding domain with novel calcium-binding motif controls domain orientation," EMBO Journal (2003) 22(8)1743-1752.
Xu, M. et al., "Basal bone phenotype and increased anabolic responses to intermittent parathyroid hormone in healthy male COX-2 knockout mice," Bone (2010) 47(2):341-52. Epub May 13, 2010.
Yang, C. et al., "Effects of continuous and pulsatile PTH treatments on rat bone marrow stromal cells," Biochem Biophys Res Commun. (2009) 380(4):791-6. Epub Feb. 3, 2009.
Yoshihara, K. et al., "Cloning and nucleotide sequence analysis of the colH gene from Clostridium histolyticum encoding a collagenase and a gelatinase," J Bacteriol (1994) 176:6489-6496.
Younes, N.A. et al., "Laboratory screening for hyperparathyroidism," Clin Chim Acta. (2005) 353(1-2):1-12.
Zang, X.Y. et al., "Effects of parathyroid hormone and estradiol on proliferation and function of human osteoblasts from fetal long bone: An in vitro study," Chin Med J (Engl). (1994) 107(8):600-3.
Zaruba, M.M. et al., "Parathyroid hormone treatment after myocardial infarction promotes cardiac repair by enhanced neovascularization and cell survival," Cardiovasc Res (2008) 77(4):722-731.
Zhou, H. et al., "Anabolic action of parathyroid hormone on cortical and cancellous bone differs between axial and appendicular skeletal sites in mice," Bone (2003) 32(5):513-520.
International Search Report and Written Opinion of the International Searching Authority for Application No. PCT/US08/004589 dated Oct. 28, 2008 (17 pages).
Extended European Search Report for Application No. 08742686.2 dated Aug. 4, 2010 (8 pages).
United States Patent Office Action for U.S. Appl. No. 12/594,547 dated Aug. 6, 2012 (12 pages).
International Search Report and Written Opinion of the International Searching Authority for Application No. PCT/US12/69831 dated Mar. 14, 2013 (12 pages).
International Search Report and Written Opinion of the International Searching Authority for Application No. PCT/US2013/25541 dated Jun. 17, 2013 (16 pages).
Restriction Requirement for U.S. Appl. No. 14/365,226 dated Jun. 22, 2015 (8 pages).
United States Patent Office Action for U.S. Appl. No. 14/365,226 dated Nov. 24, 2015 (8 pages).
United States Patent Office Action for U.S. Appl. No. 14/365,226 dated Jun. 10, 2016 (9 pages).
Partial Supplementary European Search Report dated Oct. 1, 2015 (7 pages).
Extended European Search Report for Application No. 12857691.5 dated Feb. 8, 2016 (16 pages).
Restriction Requirement for U.S. Appl. No. 14/378,067 dated Oct. 23, 2015 (9 pages).
United States Patent Office Action for U.S. Appl. No. 14/378,067 dated Feb. 17, 2016 (16 pages).
Restriction requirement for U.S. Appl. No. 14/743,629 dated Apr. 20, 2016 (8 pages).
Restriction requirement for U.S. Appl. No. 15/407,589 dated Jan. 8, 2018 (5 pages).
United States Patent Office Action for U.S. Appl. No. 15/407,589 dated Jun. 26, 2018 (44 pages).
United States Patent Office Action for U.S. Appl. No. 15/407,589 dated Jun. 26, 2019 (7 pages).

\* cited by examiner

Fig. 1

```
              3₁₀  A →           B →              C →              D →
       900        910       920           930           940           950
ColG s3b       LKEKE NDSSDK VIPMFNTTMQ SLIG-DGSRDYISEYKEEGEVNIELDKKDE
Csporogenes C  IHEKE NDSFES KIVLN-APIL SING-EDLRDIYSFEIKETKDINTKLTNLNN
CbotulinumA3C  IYEKE NDSFET KIMLN-TTVL NLNG-KDVRDIYSPDIKEAKDLDIKLNNLNN
Bcereus_AH603  LTESE NRPEE RIGLN-TTIK SLIG-GDHTDVTTFNVASAKNINISVLNEYG
Banthracis     LTESE NRPEE RIGLN-TTIK SLIG-GDHTDVYTFNVASAKNIDISVLNEYG
BB14905 B      KTHIE NRPEE MLPFN-TPLS SIME-DDHTDVYEFNVTSPKEIDISVLNENQ
Lsphaericus B  KAEIE NRPEE ILPFN-TPLK RLMD-DDHTDVYEFNVTSPKEIDISVLNENR
CcerusG9842    VTENE NNEPRQ KVNFH-TPYK TLHN-SDRVDVTTFQIDSPENINISLLNEQN
Bmycoides      SVEKE NNSFQT KLQLN-QLIR SLGN-GDTSDYFEINVETARNLQINVTKENN
Bweihensteph   AVEKE NNSFDA PLSLN-ALLR NLSD-QDQVRFVIDVKDPKDLQITVTNEQN
Bbrevis A      EKEQE NNSFSE PLKSN-VELS QTSK-QDDKDIFALKVLGNGTVKLNVTSEHD
Bbrevis B      PTEVE NNSFDD TLQLG-KEIS QTDR-TDDKDTMIQVEEGVIQVTVSSEKD
CperfringensB  IKEVE NDFDK MKVDSN-SKIV TLSN-DDLKDIYSDINIVENLDN
Csporogenes B  ISEKE NDSFDK RVGKN-QTVL TLDT-KDNRDTYYFDALAARTIDIVMENTDN
CbotulinumA3B  ISEKE NNSFDK RVCKN-QSVI TLDT-NDPRDTYYFDALIAGNIEVTAGNTDN
Csporogenes A  VSEKE NDFTT PVYYK-DLVN SVSS-SDNKDTYYFTYTKPSDITITVERTNN
CbotulinumA3A  VSEKE NDYVN PVYSK-DLVN SVSS-SDDRDITYFNVTRPSDITINVEKINK
Csordellii B   GVEQE NNSFEK PFSIN-QLVK ELDNNKDTSDYFKEVKEDAQLNISLEKTEG
ColG s3a       TKEME NDIKE GPIVEGVTVK DLNG-SDDADTFYDVKEDGDVTIELPYSGS
CperfringensA  INESE NNDFEK QIAKSNMLVK TLSE-EDYSKIYFDVAKKGNVKITLNNLNS
Csordellii A   SQEVG DDTFET GPIKINTNYS DLSD-TDNKDYYFNLDNPSNINITLENLDN
ColH s3        GTEKE NNSKET GPIVPGIPVS TIEN-TSDQYFFDVITPGEVKIDINKLGY
       970        880       890           900           910           920
              3₁₀             B →              C →              D →
```

PROXYL-(POG)₆POA(POG)₃

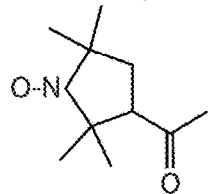
Pro-Hyp-Gly-Pro-Hyp-Gly-Pro-Hyp-Gly-Pro-Hyp-Gly-Pro-Hyp-Gly-Pro-
Hyp-Gly-Pro-Hyp-<u>Ala</u>-Pro-Hyp-Gly-Pro-Hyp-Gly-Pro-Hyp-Gly-NH₂

PROXYL-(POG)₅POA(POG)₄

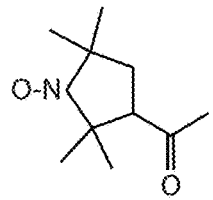
Pro-Hyp-Gly-Pro-Hyp-Gly-Pro-Hyp-Gly-Pro-Hyp-Gly-Pro-Hyp-Gly-Pro-
Hyp-<u>Ala</u>-Pro-Hyp-Gly-Pro-Hyp-Gly-Pro-Hyp-Gly-Pro-Hyp-Gly-NH₂

PROXYL-(POG)₄POA(POG)₅

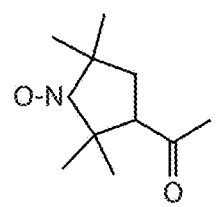
Pro-Hyp-Gly-Pro-Hyp-Gly-Pro-Hyp-Gly-Pro-Hyp-Gly-Pro-Hyp-<u>Ala</u>-Pro-
Hyp-Gly-Pro-Hyp-Gly-Pro-Hyp-Gly-Pro-Hyp-Gly-Pro-Hyp-Gly-NH₂

PROXYL-(POG)₃POA(POG)₆

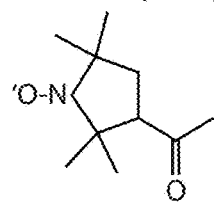
Pro-Hyp-Gly-Pro-Hyp-Gly-Pro-Hyp-Gly-Pro-Hyp-<u>Ala</u>-Pro-Hyp-Gly-Pro-
Hyp-Gly-Pro-Hyp-Gly-Pro-Hyp-Gly-Pro-Hyp-Gly-Pro-Hyp-Gly-NH₂

(POG)₄POA(POG)₅C-PROXYL

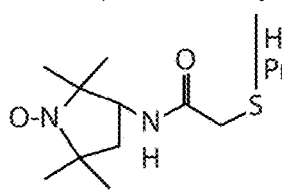
H-Pro-Hyp-Gly-Pro-Hyp-Gly-Pro-Hyp-Gly-Pro-Hyp-Gly-Pro-Hyp-Ala-
Pro-Hyp-Gly-Pro-Hyp-Gly-Pro-Hyp-Gly-Pro-Hyp-Gly-Pro-Hyp-Gly-Cys-NH₂

¹¹PROXYL-(POG)₃PCG(POG)₄

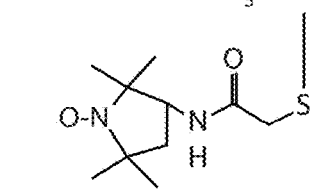
H-Pro-Hyp-Gly-Pro-Hyp-Gly-Pro-Hyp-Gly-Pro-Cys-Gly-Pro-
Hyp-Gly-Pro-Hyp-Gly-Pro-Hyp-Gly-Pro-Hyp-Gly-NH₂

Fig. 8A,
Fig. 8B
Fig. 8C,
Fig. 8D
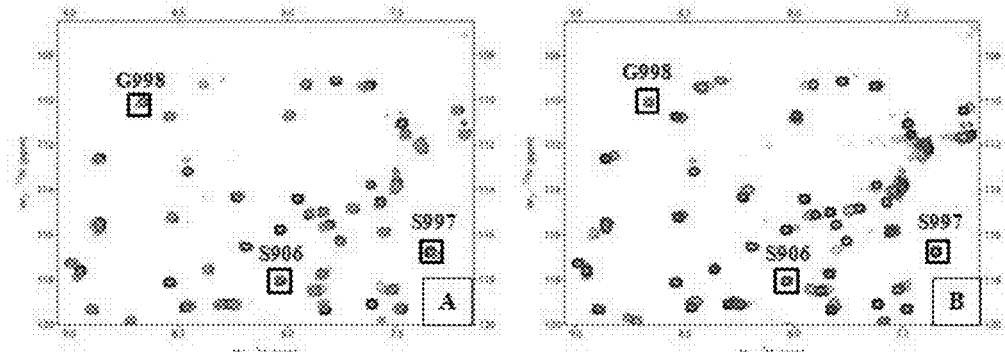
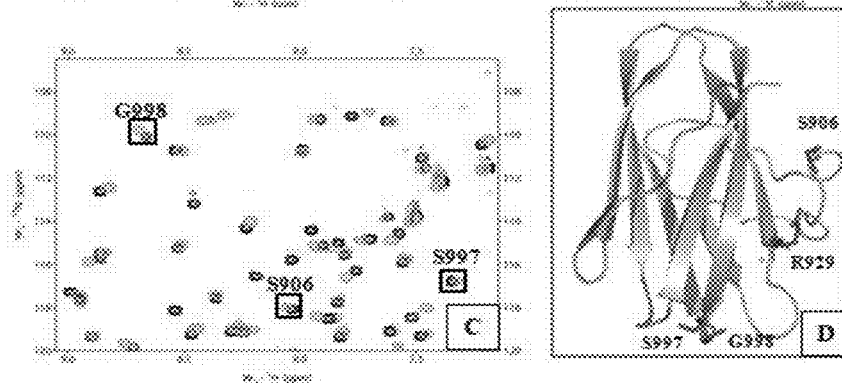
Fig. 8E,
Fig. 8F
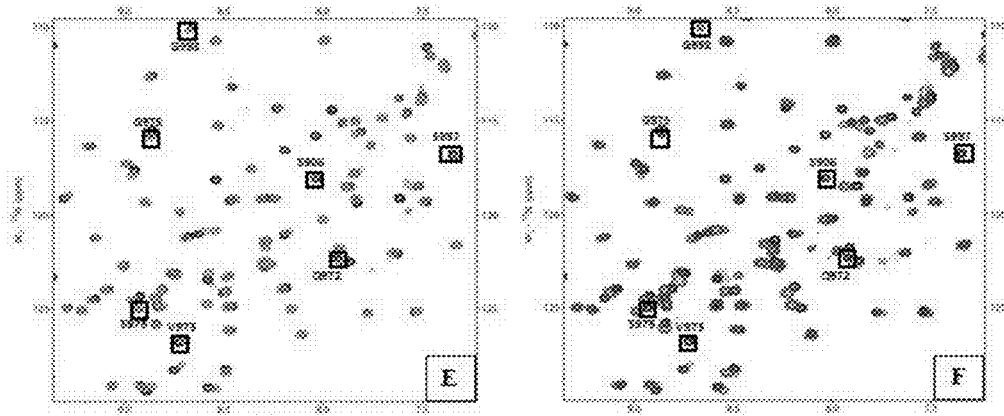
Fig. 8G,
Fig. 8H
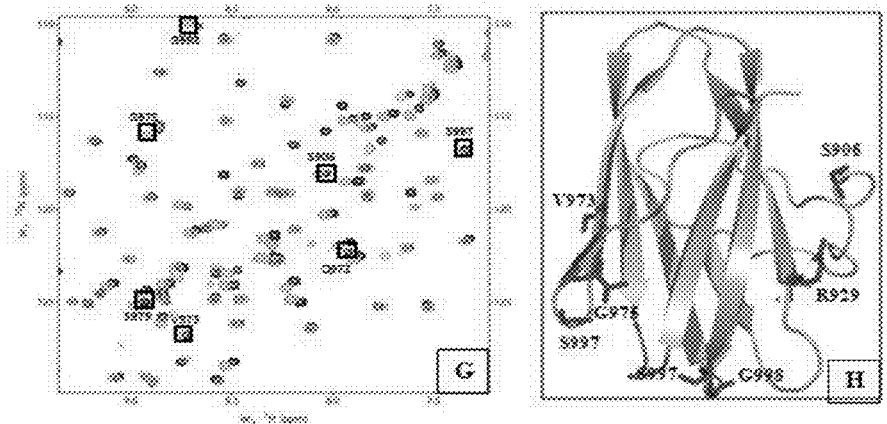

Fig. 13
A) Normal Control
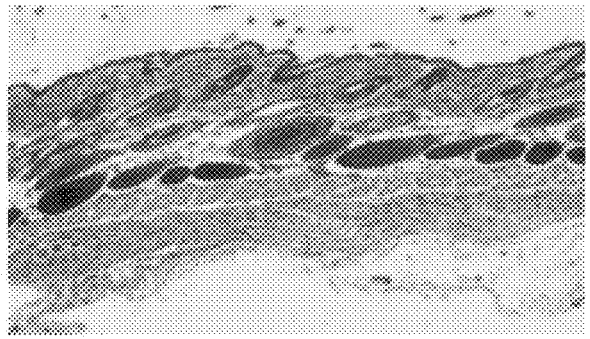
B) CYP
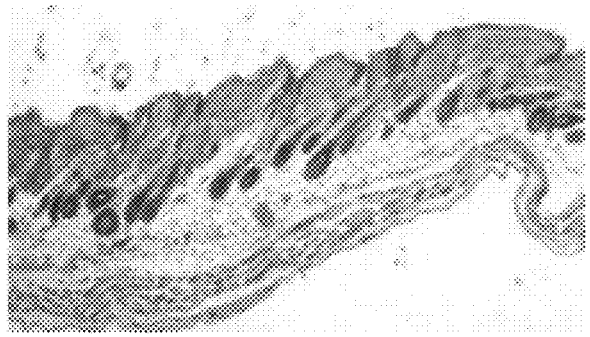
C) CYP + Agonist
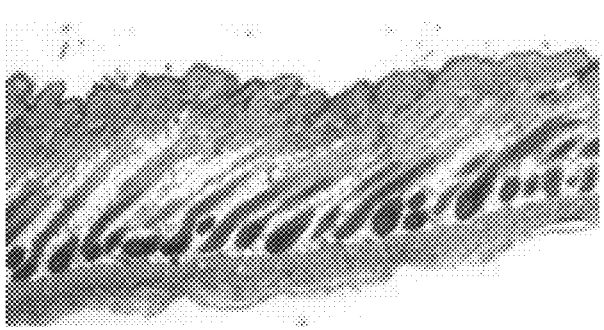
D) CYP + Antagonist
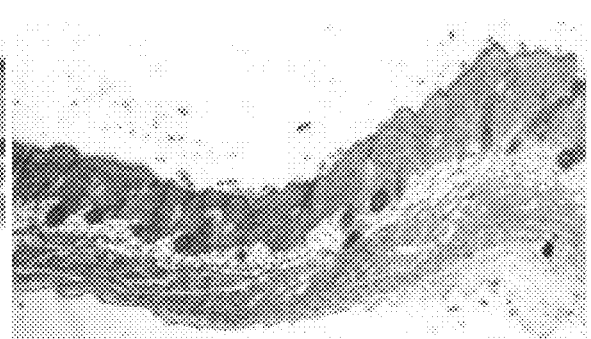

Fig. 15
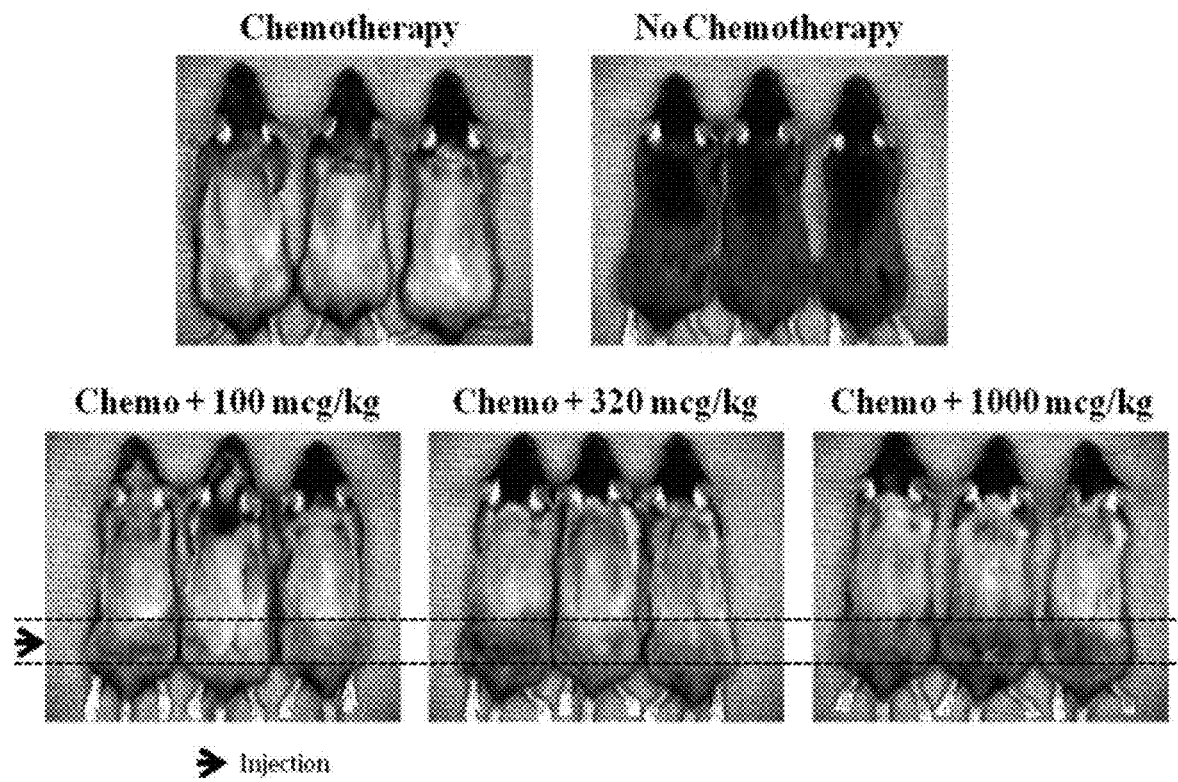
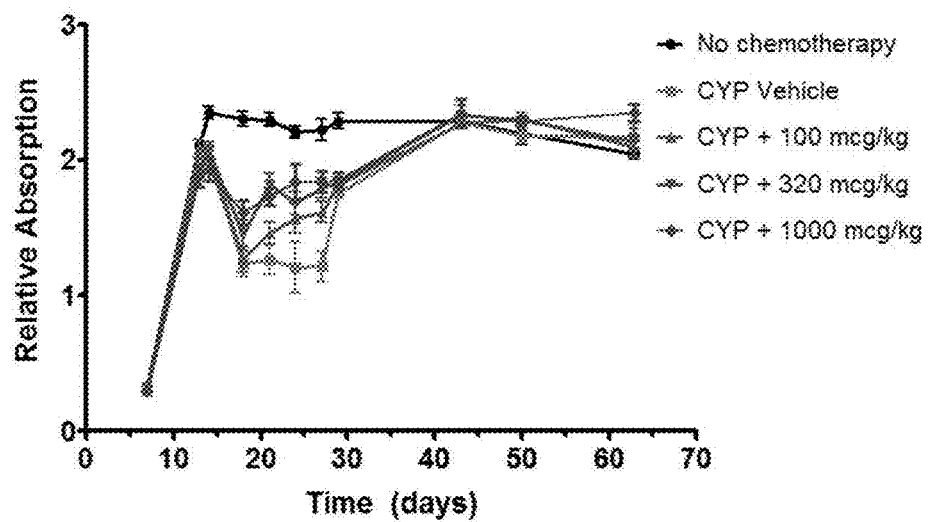

Fig. 17
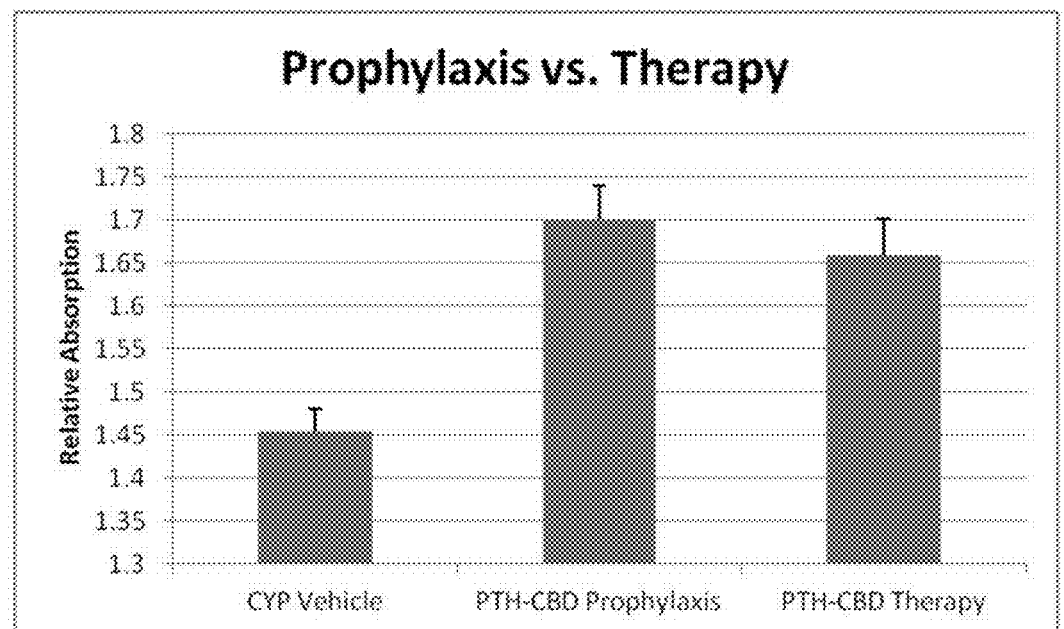
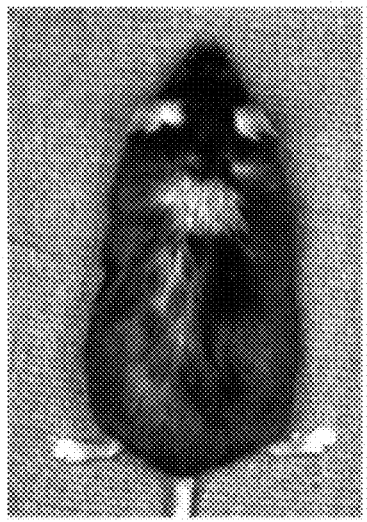
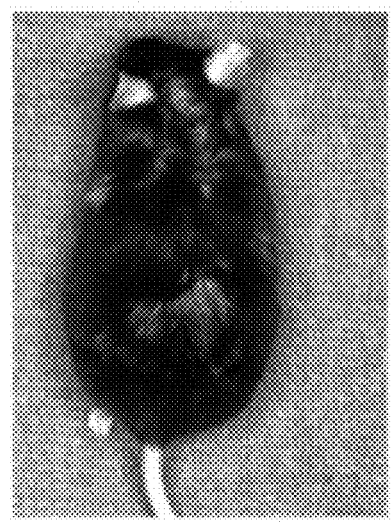

SEQUENCE LISTING

```
<160> NUMBER OF SEQ ID NOS: 47

<210> SEQ ID NO 1
<211> LENGTH: 158
<212> TYPE: PRT
<213> ORGANISM: Artificial Sequence
<220> FEATURE:
<223> OTHER INFORMATION: Synthetic fusion protein containing parathyroid
      hormone segment and collagen-binding domain

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Gly Ile Asn Ser Pro Val Tyr Pro Ile Gly Thr Glu Lys Glu Pro
        35                  40                  45

Asn Asn Ser Lys Glu Thr Ala Ser Gly Pro Ile Val Pro Gly Ile Pro
    50                  55                  60

Val Ser Gly Thr Ile Glu Asn Thr Ser Asp Gln Asp Tyr Phe Tyr Phe
65                  70                  75                  80

Asp Val Ile Thr Pro Gly Glu Val Lys Ile Asp Ile Asn Lys Leu Gly
                85                  90                  95

Tyr Gly Gly Ala Thr Trp Val Val Tyr Asp Glu Asn Asn Asn Ala Val
            100                 105                 110

Ser Tyr Ala Thr Asp Asp Gly Gln Asn Leu Ser Gly Lys Phe Lys Ala
        115                 120                 125

Asp Lys Pro Gly Arg Tyr Tyr Ile His Leu Tyr Met Phe Asn Gly Ser
    130                 135                 140

Tyr Met Pro Tyr Arg Ile Asn Ile Glu Gly Ser Val Gly Arg
145                 150                 155

<210> SEQ ID NO 2
<211> LENGTH: 251
<212> TYPE: PRT
<213> ORGANISM: Artificial Sequence
<220> FEATURE:
<223> OTHER INFORMATION: Synthetic fusion protein containing parathyroid
      hormone fragment and collagen-binding domain and polycystic kidney
      disease domain of ColH.
```

<400> SEQUENCE: 2

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Gly Ile Pro Glu Ile Lys Asp Leu Ser Glu Asn Lys Leu Pro Val
        35                  40                  45

Ile Tyr Met His Val Pro Lys Ser Gly Ala Leu Asn Gln Lys Val Val
    50                  55                  60

Phe Tyr Gly Lys Gly Thr Tyr Asp Pro Asp Gly Ser Ile Ala Gly Tyr
65                  70                  75                  80

Gln Trp Asp Phe Gly Asp Gly Ser Asp Phe Ser Ser Glu Gln Asn Pro
                85                  90                  95

Ser His Val Tyr Thr Lys Lys Gly Glu Tyr Thr Val Thr Leu Arg Val
            100                 105                 110

Met Asp Ser Ser Gly Gln Met Ser Glu Lys Thr Met Lys Ile Lys Ile
        115                 120                 125

Thr Asp Pro Val Tyr Pro Ile Gly Thr Glu Lys Glu Pro Asn Asn Ser
    130                 135                 140

Lys Glu Thr Ala Ser Gly Pro Ile Val Pro Gly Ile Pro Val Ser Gly
145                 150                 155                 160

Thr Ile Glu Asn Thr Ser Asp Gln Asp Tyr Phe Tyr Phe Asp Val Ile
                165                 170                 175

Thr Pro Gly Glu Val Lys Ile Asp Ile Asn Lys Leu Gly Tyr Gly Gly
            180                 185                 190

Ala Thr Trp Val Val Tyr Asp Glu Asn Asn Asn Ala Val Ser Tyr Ala
        195                 200                 205

Thr Asp Asp Gly Gln Asn Leu Ser Gly Lys Phe Lys Ala Asp Lys Pro
    210                 215                 220

Gly Arg Tyr Tyr Ile His Leu Tyr Met Phe Asn Gly Ser Tyr Met Pro
225                 230                 235                 240

Tyr Arg Ile Asn Ile Glu Gly Ser Val Gly Arg
                245                 250

<210> SEQ ID NO 3
<211> LENGTH: 5464
<212> TYPE: DNA
<213> ORGANISM: Artificial Sequence
<220> FEATURE:
<223> OTHER INFORMATION: Synthetic expression vector

<400> SEQUENCE: 3
agcttatcga ctgcacggtg caccaatgct tctggcgtca ggcagccatc ggaagctgtg     60
gtatggctgt gcaggtcgta aatcactgca taattcgtgt cgctcaaggc gcactcccgt    120
tctggataat gttttttgcg ccgacatcat aacggttctg gcaaatattc tgaaatgagc    180
tgttgacaat taatcatcgg ctcgtataat gtgtggaatt gtgagcggat aacaatttca    240
cacaggaaac agtattcatg tcccctatac taggttattg gaaaattaag ggccttgtgc    300
aacccactcg acttcttttg gaatatcttg aagaaaata tgaagagcat tgtatgagc     360 gcgatgaagg tgataaatgg cgaaacaaaa agtttgaatt gggtttggag tttcccaatc    420
ttccttatta tattgatggt gatgttaaat taacacagtc tatggccatc atacgttata    480
tagctgacaa gcacaacatg ttgggtggtt gtccaaaaga gcgtgcagag atttcaatgc    540

```
ttgaaggagc ggttttggat attagatacg gtgtttcgag aattgcatat agtaaagact    600
ttgaaactct caaagttgat tttcttagca agctacctga aatgctgaaa atgttcgaag    660
atcgtttatg tcataaaaca tatttaaatg gtgatcatgt aacccatcct gacttcatgt    720
tgtatgacgc tcttgatgtt gttttataca tggacccaat gtgcctggat gcgttcccaa    780
aattagtttg ttttaaaaaa cgtattgaag ctatcccaca aattgataag tacttgaaat    840
ccagcaagta tatagcatgg cctttgcagg gctggcaagc cacgtttggt ggtggcgacc    900
atcctccaaa atcggatctg atcgaaggtc gttctgtgag tgaaatacag cttatgcata    960
acctgggaaa acatctgaac tcgatggaga gagtagaatg gctgcgtaag aagctgcagg   1020
atgtgcacaa tggaattaat tccccggtat atccaatagg cactgaaaaa gaaccaaata   1080
acagtaaaga aactgcaagt ggtccaatag taccaggtat acctgttagt ggaaccatag   1140
aaaatacaag tgatcaagat tatttctatt ttgatgttat aacaccagga gaagtaaaaa   1200
tagatataaa taaattaggg tacggaggag ctacttgggt agtatatgat gaaaataata   1260
atgcagtatc ttatgccact gatgatgggc aaaatttaag tggaaagttt aaggcagata   1320
aaccaggtag atattacatc catctttaca tgtttaatgg tagttatatg ccatatagaa   1380
ttaatataga aggttcagta ggaagataat atttttattag ttgaggtaac tccactcgaa   1440
ttggtcgact cgagcggccg catcgtgact gactgacgat ctgcctcgcg cgtttcggtg   1500
atgacggtga aaacctctga cacatgcagc tcccggagac ggtcacagct tgtctgtaag   1560
cggatgccgg gagcagacaa gcccgtcagg gcgcgtcagc gggtgttggc gggtgtcggg   1620
gcgcagccat gacccagtca cgtagcgata gcggagtgta taattcttga agacgaaagg   1680
gcctcgtgat acgcctattt ttataggtta atgtcatgat aataatggtt tcttagacgt   1740
caggtggcac ttttcgggga atgtgcgcg gaacccctat ttgtttattt ttctaaatac   1800
attcaaatat gtatccgctc atgagacaat aaccctgata aatgcttcaa taatattgaa   1860
aaaggaagag tatgagtatt caacatttcc gtgtcgccct tattccctttt tttgcggcat   1920
tttgccttcc tgttttttgct cacccagaaa cgctggtgaa agtaaaagat gctgaagatc   1980
agttgggtgc acgagtgggt tacatcgaac tggatctcaa cagcggtaag atccttgaga   2040
gttttcgccc cgaagaacgt tttccaatga tgagcacttt taaagttctg ctatgtggcg   2100
cggtattatc ccgtgttgac gccgggcaag agcaactcgg tcgccgcata cactattctc   2160
agaatgactt ggttgagtac tcaccagtca cagaaaagca tcttacggat ggcatgacag   2220
taagagaatt atgcagtgct gccataacca tgagtgataa cactgcggcc aacttacttc   2280
tgacaacgat cggaggaccg aaggagctaa ccgcttttttt gcacaacatg ggggatcatg   2340
taactcgcct tgatcgttgg gaaccggagc tgaatgaagc cataccaaac gacgagcgtg   2400
acaccacgat gcctgcagca atggcaacaa cgttgcgcaa actattaact ggcgaactac   2460
ttactctagc ttcccggcaa caattaatag actggatgga gcggataaag ttgcaggac   2520
cacttctgcg ctcggccctt ccggctggct ggtttattgc tgataaatct ggagccggtg   2580
agcgtgggtc tcgcggtatc attgcagcac tggggccaga tggtaagccc tcccgtatcg   2640
tagttatcta cacgacgggg agtcaggcaa ctatggatga acgaaataga cagatcgctg   2700
agataggtgc ctcactgatt aagcattggt aactgtcaga ccaagtttac tcatatatac   2760
tttagattga tttaaaactt catttttaat ttaaaaggat ctaggtgaag atccttttttg   2820
ataatctcat gaccaaaatc ccttaacgtg agttttcgtt ccactgagcg tcagaccccg   2880
tagaaaagat caaaggatct tcttgagatc ctttttttct gcgcgtaatc tgctgcttgc   2940
```

```
aaacaaaaaa accaccgcta ccagcggtgg tttgtttgcc ggatcaagag ctaccaactc    3000
tttttccgaa ggtaactggc ttcagcagag cgcagatacc aaatactgtc cttctagtgt    3060
agccgtagtt aggccaccac ttcaagaact ctgtagcacc gcctacatac ctcgctctgc    3120
taatcctgtt accagtggct gctgccagtg gcgataagtc gtgtcttacc gggttggact    3180
caagacgata gttaccggat aaggcgcagc ggtcgggctg aacgggggt  tcgtgcacac    3240
agcccagctt ggagcgaacg acctacaccg aactgagata cctacagcgt gagctatgag    3300
aaagcgccac gcttcccgaa gggagaaagg cggacaggta tccggtaagc ggcagggtcg    3360
gaacaggaga gcgcacgagg gagcttccag ggggaaacgc ctggtatctt tatagtcctg    3420
tcgggtttcg ccacctctga cttgagcgtc gattttgtg  atgctcgtca gggggcgga    3480
gcctatggaa aaacgccagc aacgcggcct ttttacggtt cctggccttt tgctggcctt    3540
ttgctcacat gttctttcct gcgttatccc ctgattctgt ggataaccgt attaccgcct    3600
ttgagtgagc tgataccgct cgccgcagcc gaacgaccga cgcagcgag  tcagtgagcg    3660
aggaagcgga agagcgcctg atgcggtatt ttctccttac gcatctgtgc ggtatttcac    3720
accgcataaa ttccgacacc atcgaatggt gcaaaacctt tcgcggtatg gcatgatagc    3780
gcccggaaga gagtcaattc agggtggtga atgtgaaacc agtaacgtta tacgatgtcg    3840
cagagtatgc cggtgtctct tatcagaccg tttcccgcgt ggtgaaccag gccagccacg    3900
tttctgcgaa aacgcgggaa aaagtggaag cggcgatggc ggagctgaat tacattccca    3960
accgcgtggc acaacaactg gcgggcaaac agtcgttgct gattggcgtt gccacctcca    4020
gtctggccct gcacgcgccg tcgcaaattg tcgcggcgat taaatctcgc gccgatcaac    4080
tgggtgccag cgtggtggtg tcgatggtag aacgaagcgg cgtcgaagcc tgtaaagcgg    4140
cggtgcacaa tcttctcgcg caacgcgtca gtgggctgat cattaactat ccgctggatg    4200
accaggatgc cattgctgtg gaagctgcct gcactaatgt tccggcgtta tttcttgatg    4260
tctctgacca gacacccatc aacagtatta ttttctccca tgaagacggt acgcgactgg    4320
gcgtggagca tctggtcgca ttgggtcacc agcaaatcgc gctgttagcg ggcccattaa    4380
gttctgtctc ggcgcgtctg cgtctggctg gctggcataa atatctcact cgcaatcaaa    4440
ttcagccgat agcggaacgg gaaggcgact ggagtgccat gtccggtttt caacaaacca    4500
tgcaaatgct gaatgagggc atcgttccca ctgcgatgct ggttgccaac gatcagatgg    4560
cgctgggcgc aatgcgcgcc attaccgagt ccgggctgcg cgttggtgcg gatatctcgg    4620
tagtgggata cgacgatacc gaagacagct catgttatat cccgccgtta accaccatca    4680
aacaggattt cgcctgctg  gggcaaacca gcgtggaccg cttgctgcaa ctctctcagg    4740
gccaggcggt gaagggcaat cagctgttgc ccgtctcact ggtgaaaaga aaaccaccc     4800
tggcgcccaa tacgcaaacc gcctctcccc gcgcgttggc cgattcatta atgcagctgg    4860
cacgacaggt ttcccgactg gaaagcgggc agtgagcgca acgcaattaa tgtgagttag    4920
ctcactcatt aggcacccca ggctttacac tttatgcttc cggctcgtat gttgtgtgga    4980
attgtgagcg gataacaatt tcacacagga aacagctatg accatgatta cggattcact    5040
ggccgtcgtt ttacaacgtc gtgactggga aaaccctggc gttacccaac ttaatcgcct    5100
tgcagcacat ccccctttcg ccagctggcg taatagcgaa gaggcccgca ccgatcgccc    5160
ttcccaacag ttgcgcagcc tgaatggcga atggcgcttt gcctggtttc cggcaccaga    5220
agcggtgccg gaaagctggc tggagtgcga tcttcctgag gccgatactg tcgtcgtccc    5280
```

```
ctcaaactgg cagatgcacg gttacgatgc gcccatctac accaacgtaa cctatcccat      5340
tacggtcaat ccgccgtttg ttcccacgga gaatccgacg ggttgttact cgctcacatt      5400
taatgttgat gaaagctggc tacaggaagg ccagacgcga attattttg atggcgttgg       5460 aatt                                                                   5464
```

<210> SEQ ID NO 4
<211> LENGTH: 383
<212> TYPE: PRT
<213> ORGANISM: Artificial Sequence
<220> FEATURE:
<223> OTHER INFORMATION: Synthetic GST-PTH-CBD fusion protein

<400> SEQUENCE: 4

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Ile Glu Gly
    210                 215                 220

Arg Ser Val Ser Glu Ile Gln Leu Met His Asn Leu Gly Lys His Leu
225                 230                 235                 240

Asn Ser Met Glu Arg Val Glu Trp Leu Arg Lys Lys Leu Gln Asp Val
                245                 250                 255

His Asn Gly Ile Asn Ser Pro Val Pro Ile Gly Thr Glu Lys Glu
            260                 265                 270

Pro Asn Asn Ser Lys Glu Thr Ala Ser Gly Pro Ile Val Pro Gly Ile
        275                 280                 285

Pro Val Ser Gly Thr Ile Glu Asn Thr Ser Asp Gln Asp Tyr Phe Tyr
    290                 295                 300

Phe Asp Val Ile Thr Pro Gly Glu Val Lys Ile Asp Ile Asn Lys Leu
305                 310                 315                 320

Gly Tyr Gly Gly Ala Thr Trp Val Val Tyr Asp Glu Asn Asn Asn Ala
```

```
                325                 330                 335

Val Ser Tyr Ala Thr Asp Asp Gly Gln Asn Leu Ser Gly Lys Phe Lys
            340                 345                 350

Ala Asp Lys Pro Gly Arg Tyr Tyr Ile His Leu Tyr Met Phe Asn Gly
        355                 360                 365

Ser Tyr Met Pro Tyr Arg Ile Asn Ile Glu Gly Ser Val Gly Arg
    370                 375                 380

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide: Factor Xa recognition
      sequence

<400> SEQUENCE: 5

Ile Glu Gly Arg
1

<210> SEQ ID NO 6
<211> LENGTH: 1021
<212> TYPE: PRT
<213> ORGANISM: Clostridium histolyticum

<400> SEQUENCE: 6

Met Lys Arg Lys Cys Leu Ser Lys Arg Leu Met Leu Ala Ile Thr Met
1               5                   10                  15

Ala Thr Ile Phe Thr Val Asn Ser Thr Leu Pro Ile Tyr Ala Ala Val
            20                  25                  30

Asp Lys Asn Asn Ala Thr Ala Ala Val Gln Asn Glu Ser Lys Arg Tyr
        35                  40                  45

Thr Val Ser Tyr Leu Lys Thr Leu Asn Tyr Tyr Asp Leu Val Asp Leu
    50                  55                  60

Leu Val Lys Thr Glu Ile Glu Asn Leu Pro Asp Leu Phe Gln Tyr Ser
65                  70                  75                  80

Ser Asp Ala Lys Glu Phe Tyr Gly Asn Lys Thr Arg Met Ser Phe Ile
                85                  90                  95

Met Asp Glu Ile Gly Arg Arg Ala Pro Gln Tyr Thr Glu Ile Asp His
            100                 105                 110

Lys Gly Ile Pro Thr Leu Val Glu Val Val Arg Ala Gly Phe Tyr Leu
        115                 120                 125

Gly Phe His Asn Lys Glu Leu Asn Glu Ile Asn Lys Arg Ser Phe Lys
    130                 135                 140

Glu Arg Val Ile Pro Ser Ile Leu Ala Ile Gln Lys Asn Pro Asn Phe
145                 150                 155                 160

Lys Leu Gly Thr Glu Val Gln Asp Lys Ile Val Ser Ala Thr Gly Leu
                165                 170                 175

Leu Ala Gly Asn Glu Thr Ala Pro Pro Glu Val Val Asn Asn Phe Thr
            180                 185                 190

Pro Ile Leu Gln Asp Cys Ile Lys Asn Ile Asp Arg Tyr Ala Leu Asp
        195                 200                 205

Asp Leu Lys Ser Lys Ala Leu Phe Asn Val Leu Ala Ala Pro Thr Tyr
    210                 215                 220

Asp Ile Thr Glu Tyr Leu Arg Ala Thr Lys Glu Lys Pro Glu Asn Thr
225                 230                 235                 240

Pro Trp Tyr Gly Lys Ile Asp Gly Phe Ile Asn Glu Leu Lys Lys Leu
```

```
                    245                 250                 255
Ala Leu Tyr Gly Lys Ile Asn Asp Asn Asn Ser Trp Ile Ile Asp Asn
                260                 265                 270

Gly Ile Tyr His Ile Ala Pro Leu Gly Lys Leu His Ser Asn Asn Lys
            275                 280                 285

Ile Gly Ile Glu Thr Leu Thr Glu Val Met Lys Val Tyr Pro Tyr Leu
        290                 295                 300

Ser Met Gln His Leu Gln Ser Ala Asp Gln Ile Lys Arg His Tyr Asp
305                 310                 315                 320

Ser Lys Asp Ala Glu Gly Asn Lys Ile Pro Leu Asp Lys Phe Lys Lys
                325                 330                 335

Glu Gly Lys Glu Lys Tyr Cys Pro Lys Thr Tyr Thr Phe Asp Asp Gly
            340                 345                 350

Lys Val Ile Ile Lys Ala Gly Ala Arg Val Glu Glu Lys Val Lys
        355                 360                 365

Arg Leu Tyr Trp Ala Ser Lys Glu Val Asn Ser Gln Phe Phe Arg Val
    370                 375                 380

Tyr Gly Ile Asp Lys Pro Leu Glu Glu Gly Asn Pro Asp Asp Ile Leu
385                 390                 395                 400

Thr Met Val Ile Tyr Asn Ser Pro Glu Glu Tyr Lys Leu Asn Ser Val
                405                 410                 415

Leu Tyr Gly Tyr Asp Thr Asn Asn Gly Gly Met Tyr Ile Glu Pro Glu
            420                 425                 430

Gly Thr Phe Phe Thr Tyr Glu Arg Glu Ala Gln Glu Ser Thr Tyr Thr
        435                 440                 445

Leu Glu Glu Leu Phe Arg His Glu Tyr Thr His Tyr Leu Gln Gly Arg
    450                 455                 460

Tyr Ala Val Pro Gly Gln Trp Gly Arg Thr Lys Leu Tyr Asp Asn Asp
465                 470                 475                 480

Arg Leu Thr Trp Tyr Glu Glu Gly Gly Ala Glu Leu Phe Ala Gly Ser
                485                 490                 495

Thr Arg Thr Ser Gly Ile Leu Pro Arg Lys Ser Ile Val Ser Asn Ile
            500                 505                 510

His Asn Thr Thr Arg Asn Asn Arg Tyr Lys Leu Ser Asp Thr Val His
        515                 520                 525

Ser Lys Tyr Gly Ala Ser Phe Glu Phe Tyr Asn Tyr Ala Cys Met Phe
    530                 535                 540

Met Asp Tyr Met Tyr Asn Lys Asp Met Gly Ile Leu Asn Lys Leu Asn
545                 550                 555                 560

Asp Leu Ala Lys Asn Asn Asp Val Asp Gly Tyr Asp Asn Tyr Ile Arg
                565                 570                 575

Asp Leu Ser Ser Asn Tyr Ala Leu Asn Asp Lys Tyr Gln Asp His Met
            580                 585                 590

Gln Glu Arg Ile Asp Asn Tyr Glu Asn Leu Thr Val Pro Phe Val Ala
        595                 600                 605

Asp Asp Tyr Leu Val Arg His Ala Tyr Lys Asn Pro Asn Glu Ile Tyr
    610                 615                 620

Ser Glu Ile Ser Glu Val Ala Lys Leu Lys Asp Ala Lys Ser Glu Val
625                 630                 635                 640

Lys Lys Ser Gln Tyr Phe Ser Thr Phe Thr Leu Arg Gly Ser Tyr Thr
                645                 650                 655

Gly Gly Ala Ser Lys Gly Lys Leu Glu Asp Gln Lys Ala Met Asn Lys
            660                 665                 670
```

Phe Ile Asp Asp Ser Leu Lys Lys Leu Asp Thr Tyr Ser Trp Ser Gly
            675                 680                 685

Tyr Lys Thr Leu Thr Ala Tyr Phe Thr Asn Tyr Lys Val Asp Ser Ser
        690                 695                 700

Asn Arg Val Thr Tyr Asp Val Phe His Gly Tyr Leu Pro Asn Glu
705                 710                 715                 720

Gly Asp Ser Lys Asn Ser Leu Pro Tyr Gly Lys Ile Asn Gly Thr Tyr
                725                 730                 735

Lys Gly Thr Glu Lys Glu Lys Ile Lys Phe Ser Ser Glu Gly Ser Phe
            740                 745                 750

Asp Pro Asp Gly Lys Ile Val Ser Tyr Glu Trp Asp Phe Gly Asp Gly
            755                 760                 765

Asn Lys Ser Asn Glu Glu Asn Pro Glu His Ser Tyr Asp Lys Val Gly
        770                 775                 780

Thr Tyr Thr Val Lys Leu Lys Val Thr Asp Asp Lys Gly Glu Ser Ser
785                 790                 795                 800

Val Ser Thr Thr Thr Ala Glu Ile Lys Asp Leu Ser Glu Asn Lys Leu
                805                 810                 815

Pro Val Ile Tyr Met His Val Pro Lys Ser Gly Ala Leu Asn Gln Lys
            820                 825                 830

Val Val Phe Tyr Gly Lys Gly Thr Tyr Asp Pro Asp Gly Ser Ile Ala
            835                 840                 845

Gly Tyr Gln Trp Asp Phe Gly Asp Gly Ser Asp Phe Ser Ser Glu Gln
        850                 855                 860

Asn Pro Ser His Val Tyr Thr Lys Lys Gly Glu Tyr Thr Val Thr Leu
865                 870                 875                 880

Arg Val Met Asp Ser Ser Gly Gln Met Ser Glu Lys Thr Met Lys Ile
                885                 890                 895

Lys Ile Thr Asp Pro Val Tyr Pro Ile Gly Thr Glu Lys Glu Pro Asn
            900                 905                 910

Asn Ser Lys Glu Thr Ala Ser Gly Pro Ile Val Pro Gly Ile Pro Val
        915                 920                 925

Ser Gly Thr Ile Glu Asn Thr Ser Asp Gln Asp Tyr Phe Tyr Phe Asp
    930                 935                 940

Val Ile Thr Pro Gly Glu Val Lys Ile Asp Ile Asn Lys Leu Gly Tyr
945                 950                 955                 960

Gly Gly Ala Thr Trp Val Val Tyr Asp Glu Asn Asn Asn Ala Val Ser
                965                 970                 975

Tyr Ala Thr Asp Asp Gly Gln Asn Leu Ser Gly Lys Phe Lys Ala Asp
            980                 985                 990

Lys Pro Gly Arg Tyr Tyr Ile His Leu Tyr Met Phe Asn Gly Ser Tyr
            995                 1000                1005

Met Pro Tyr Arg Ile Asn Ile Glu Gly Ser Val Gly Arg
        1010                1015                1020

<210> SEQ ID NO 7
<211> LENGTH: 84
<212> TYPE: PRT
<213> ORGANISM: Homo sapiens

<400> SEQUENCE: 7

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His

```
                20                  25                  30
Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 8
<211> LENGTH: 141
<212> TYPE: PRT
<213> ORGANISM: Homo sapiens

<400> SEQUENCE: 8

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
                20                  25                  30

Thr Ala Glu Ile Arg Ala Thr Ser Glu Val Ser Pro Asn Ser Lys Pro
            35                  40                  45

Ser Pro Asn Thr Lys Asn His Pro Val Arg Phe Gly Ser Asp Asp Glu
        50                  55                  60

Gly Arg Tyr Leu Thr Gln Glu Thr Asn Lys Val Glu Thr Tyr Lys Glu
65                  70                  75                  80

Gln Pro Leu Lys Thr Pro Gly Lys Lys Lys Gly Lys Pro Gly Lys
                85                  90                  95

Arg Lys Glu Gln Glu Lys Lys Arg Arg Thr Arg Ser Ala Trp Leu
            100                 105                 110

Asp Ser Gly Val Thr Gly Ser Gly Leu Glu Gly Asp His Leu Ser Asp
        115                 120                 125

Thr Ser Thr Thr Ser Leu Glu Leu Asp Ser Arg Arg His
        130                 135                 140

<210> SEQ ID NO 9
<211> LENGTH: 160
<212> TYPE: PRT
<213> ORGANISM: Artificial Sequence
<220> FEATURE:
<223> OTHER INFORMATION: Synthetic Gly-Ser-PTH(1-33)-CBD fusion protein

<400> SEQUENCE: 9

Gly Ser Ser Val Ser Glu Ile Gln Leu Met His Asn Leu Gly Lys His
1               5                   10                  15

Leu Asn Ser Met Glu Arg Val Glu Trp Leu Arg Lys Lys Leu Gln Asp
                20                  25                  30

Val His Asn Gly Ile Asn Ser Pro Val Tyr Pro Ile Gly Thr Glu Lys
            35                  40                  45

Glu Pro Asn Asn Ser Lys Glu Thr Ala Ser Gly Pro Ile Val Pro Gly
        50                  55                  60

Ile Pro Val Ser Gly Thr Ile Glu Asn Thr Ser Asp Gln Asp Tyr Phe
65                  70                  75                  80

Tyr Phe Asp Val Ile Thr Pro Gly Glu Val Lys Ile Asp Ile Asn Lys
                85                  90                  95

Leu Gly Tyr Gly Gly Ala Thr Trp Val Val Tyr Asp Glu Asn Asn Asn
            100                 105                 110
```

```
Ala Val Ser Tyr Ala Thr Asp Asp Gly Gln Asn Leu Ser Gly Lys Phe
            115                 120                 125

Lys Ala Asp Lys Pro Gly Arg Tyr Tyr Ile His Leu Tyr Met Phe Asn
    130                 135                 140

Gly Ser Tyr Met Pro Tyr Arg Ile Asn Ile Glu Gly Ser Val Gly Arg
145                 150                 155                 160

<210> SEQ ID NO 10
<211> LENGTH: 152
<212> TYPE: PRT
<213> ORGANISM: Artificial Sequence
<220> FEATURE:
<223> OTHER INFORMATION: Synthetic PTH(7-33)-CBD fusion protein

<400> SEQUENCE: 10

Leu Met His Asn Leu Gly Lys His Leu Asn Ser Met Glu Arg Val Glu
1               5                   10                  15

Trp Leu Arg Lys Lys Leu Gln Asp Val His Asn Gly Ile Asn Ser Pro
            20                  25                  30

Val Tyr Pro Ile Gly Thr Glu Lys Glu Pro Asn Asn Ser Lys Glu Thr
        35                  40                  45

Ala Ser Gly Pro Ile Val Pro Gly Ile Pro Val Ser Gly Thr Ile Glu
    50                  55                  60

Asn Thr Ser Asp Gln Asp Tyr Phe Tyr Phe Asp Val Ile Thr Pro Gly
65                  70                  75                  80

Glu Val Lys Ile Asp Ile Asn Lys Leu Gly Tyr Gly Gly Ala Thr Trp
                85                  90                  95

Val Val Tyr Asp Glu Asn Asn Ala Val Ser Tyr Ala Thr Asp Asp
            100                 105                 110

Gly Gln Asn Leu Ser Gly Lys Phe Lys Ala Asp Lys Pro Gly Arg Tyr
            115                 120                 125

Tyr Ile His Leu Tyr Met Phe Asn Gly Ser Tyr Met Pro Tyr Arg Ile
        130                 135                 140

Asn Ile Glu Gly Ser Val Gly Arg
145                 150

<210> SEQ ID NO 11
<211> LENGTH: 35
<212> TYPE: PRT
<213> ORGANISM: Artificial Sequence
<220> FEATURE:
<223> OTHER INFORMATION: Synthetic PTH(1-33) with Gly-Ser amino terminal
      extension

<400> SEQUENCE: 11

Gly Ser Ser Val Ser Glu Ile Gln Leu Met His Asn Leu Gly Lys His
1               5                   10                  15

Leu Asn Ser Met Glu Arg Val Glu Trp Leu Arg Lys Lys Leu Gln Asp
            20                  25                  30

Val His Asn
        35

<210> SEQ ID NO 12
<211> LENGTH: 6
<212> TYPE: PRT
<213> ORGANISM: Artificial Sequence
<220> FEATURE:
<223> OTHER INFORMATION: Synthetic thrombin cleavage sequence

<400> SEQUENCE: 12
```

Leu Val Pro Arg Gly Ser
1               5

<210> SEQ ID NO 13
<211> LENGTH: 111
<212> TYPE: PRT
<213> ORGANISM: Clostridium histolyticum

<400> SEQUENCE: 13

Leu Lys Glu Lys Glu Asn Asn Asp Ser Ser Asp Lys Ala Thr Val Ile
1               5                   10                  15

Pro Asn Phe Asn Thr Thr Met Gln Gly Ser Leu Leu Gly Asp Asp Ser
                20                  25                  30

Arg Asp Tyr Tyr Ser Phe Glu Val Lys Glu Glu Gly Glu Val Asn Ile
            35                  40                  45

Glu Leu Asp Lys Lys Asp Glu Phe Gly Val Thr Trp Thr Leu His Pro
    50                  55                  60

Glu Ser Asn Ile Asn Asp Arg Ile Thr Tyr Gly Gln Val Asp Gly Asn
65                  70                  75                  80

Lys Val Ser Asn Lys Val Lys Leu Arg Pro Gly Lys Tyr Tyr Leu Leu
                85                  90                  95

Val Tyr Lys Tyr Ser Gly Ser Gly Asn Tyr Glu Leu Arg Val Asn
                100                 105                 110

<210> SEQ ID NO 14
<211> LENGTH: 111
<212> TYPE: PRT
<213> ORGANISM: C. sporogenes

<400> SEQUENCE: 14

Ile His Glu Lys Glu Asn Asn Asp Ser Phe Glu Ser Ala Asn Lys Ile
1               5                   10                  15

Val Leu Asn Ala Pro Ile Leu Gly Ser Leu Asn Gly Glu Asp Leu Arg
                20                  25                  30

Asp Ile Tyr Ser Phe Glu Ile Lys Glu Thr Lys Asp Leu Asn Ile Lys
            35                  40                  45

Leu Thr Asn Leu Asn Asn Leu Gly Leu Thr Trp Thr Leu Tyr Lys Glu
    50                  55                  60

Ser Asp Leu Asn Asn Tyr Ile Ala Tyr Gly Ser Lys Leu Gly Ser Thr
65                  70                  75                  80

Ile Val Gly Asn Cys His Val Thr Pro Gly Lys Tyr Tyr Leu Tyr Val
                85                  90                  95

Tyr Lys Tyr Ser Gly Asn Asn Gly Asn Tyr Ser Leu Ile Ile Lys
                100                 105                 110

<210> SEQ ID NO 15
<211> LENGTH: 111
<212> TYPE: PRT
<213> ORGANISM: C. botulinum

<400> SEQUENCE: 15

Ile Tyr Glu Lys Glu Asn Asn Asp Ser Phe Glu Thr Ala Asn Lys Ile
1               5                   10                  15

Met Leu Asn Thr Thr Val Leu Gly Asn Leu Asn Gly Lys Asp Val Arg
                20                  25                  30

Asp Ile Tyr Ser Phe Asp Ile Lys Glu Ala Lys Asp Leu Asp Ile Lys
            35                  40                  45

Leu Asn Asn Leu Asn Asn Leu Gly Leu Ala Trp Asn Leu Tyr Lys Glu

```
                50                  55                  60
Ser Asp Leu Asn Asn Tyr Ile Ala Tyr Gly Ser Val Ser Gly Asn Thr
 65                  70                  75                  80

Ile Lys Gly Lys Cys Asn Val Ala Pro Gly Lys Tyr Tyr Leu Tyr Val
                 85                  90                  95

Tyr Lys Tyr Ser Gly Asp Asn Gly Asn Tyr Ser Leu Ala Ile Lys
                100                 105                 110
```

<210> SEQ ID NO 16
<211> LENGTH: 111
<212> TYPE: PRT
<213> ORGANISM: B. cereus

<400> SEQUENCE: 16

```
Leu Thr Glu Ser Glu Pro Asn Asn Arg Pro Glu Glu Ala Asn Arg Ile
 1               5                  10                  15

Gly Leu Asn Thr Thr Ile Lys Gly Ser Leu Ile Gly Gly Asp His Thr
                 20                  25                  30

Asp Val Tyr Thr Phe Asn Val Ala Ser Ala Lys Asn Ile Asn Ile Ser
                 35                  40                  45

Val Leu Asn Glu Tyr Gly Ile Gly Met Thr Trp Val Leu His His Glu
         50                  55                  60

Ser Asp Met Gln Asn Tyr Ala Ala Tyr Gly Gln Val Asn Gly Asn His
 65                  70                  75                  80

Ile Glu Ala Asn Phe Asn Ala Lys Pro Gly Lys Tyr Tyr Leu Tyr Val
                 85                  90                  95

Tyr Lys Tyr Asp Asn Gly Asp Gly Thr Tyr Glu Leu Ser Val Lys
                100                 105                 110
```

<210> SEQ ID NO 17
<211> LENGTH: 111
<212> TYPE: PRT
<213> ORGANISM: B. anthracis

<400> SEQUENCE: 17

```
Leu Thr Glu Ser Glu Pro Asn Asn Arg Pro Glu Glu Ala Asn Arg Ile
 1               5                  10                  15

Gly Leu Asn Thr Thr Ile Lys Gly Ser Leu Ile Gly Gly Asp His Thr
                 20                  25                  30

Asp Val Tyr Thr Phe Asn Val Ala Ser Ala Lys Asn Ile Asp Ile Ser
                 35                  40                  45

Val Leu Asn Glu Tyr Gly Ile Gly Met Thr Trp Val Leu His His Glu
         50                  55                  60

Ser Asp Met Gln Asn Tyr Ala Ala Tyr Gly Gln Ala Asn Gly Asn His
 65                  70                  75                  80

Ile Glu Ala Asn Phe Asn Ala Lys Pro Gly Lys Tyr Tyr Leu Tyr Val
                 85                  90                  95

Tyr Lys Tyr Asp Asn Gly Asp Gly Thr Tyr Glu Leu Ser Val Lys
                100                 105                 110
```

<210> SEQ ID NO 18
<211> LENGTH: 111
<212> TYPE: PRT
<213> ORGANISM: Bacillus sp.

<400> SEQUENCE: 18

```
Lys Thr Glu Ile Glu Pro Asn Asn Arg Pro Glu Glu Ala Thr Met Leu
 1               5                  10                  15
```

```
Pro Phe Asn Thr Pro Leu Ser Gly Ser Leu Met Glu Asp Asp His Thr
            20                  25                  30

Asp Val Tyr Glu Phe Asn Val Thr Ser Pro Lys Glu Ile Asp Ile Ser
        35                  40                  45

Val Leu Asn Glu Asn Gln Ile Gly Met Thr Trp Val Leu Tyr His Glu
    50                  55                  60

Ser Asp Ser Gln Asn Tyr Ala Ser Phe Gly Gln Glu Asp Gly Asn Met
65                  70                  75                  80

Ile Asn Gly Lys Trp Asn Ala Lys Pro Gly Lys Tyr Tyr Leu Tyr Val
                85                  90                  95

Tyr Lys Phe Glu Asn Glu Asn Gly Thr Tyr Thr Val His Val Gln
            100                 105                 110
```

<210> SEQ ID NO 19
<211> LENGTH: 111
<212> TYPE: PRT
<213> ORGANISM: L. sphaericus

<400> SEQUENCE: 19

```
Lys Ala Glu Ile Glu Pro Asn Asn Arg Pro Glu Glu Ala Thr Ile Leu
1               5                   10                  15

Pro Phe Asn Thr Pro Leu Lys Gly Arg Leu Met Asp Asp Asp His Thr
            20                  25                  30

Asp Val Tyr Glu Phe Asn Val Thr Ser Pro Lys Glu Leu Asp Ile Ser
        35                  40                  45

Val Leu Asn Glu Asn Arg Ile Gly Met Thr Trp Val Leu Tyr His Glu
    50                  55                  60

Ser Asp Ser Gln Asn Tyr Ala Ser Phe Gly Gln Glu Gly Asn Met
65                  70                  75                  80

Ile Asn Gly Lys Leu His Ala Glu Pro Gly Lys Tyr Tyr Leu Tyr Val
                85                  90                  95

Tyr Lys Phe Glu Asn Glu Asn Gly Thr Tyr Thr Val Gln Val Gln
            100                 105                 110
```

<210> SEQ ID NO 20
<211> LENGTH: 111
<212> TYPE: PRT
<213> ORGANISM: C. cerus

<400> SEQUENCE: 20

```
Val Thr Glu Asn Glu Pro Asn Asn Gly Pro Arg Gln Ala Asn Lys Val
1               5                   10                  15

Asn Phe His Thr Pro Val Lys Gly Thr Leu His Asn Ser Asp Arg Val
            20                  25                  30

Asp Val Phe Thr Phe Gln Ile Asp Ser Pro Glu Asn Ile Asn Ile Ser
        35                  40                  45

Leu Leu Asn Glu Gln Asn Ile Gly Met Thr Trp Val Leu His His Glu
    50                  55                  60

Ser Asp Leu Asn Asn Tyr Val Ala Tyr Gly Glu Asn Glu Gly Asn Val
65                  70                  75                  80

Val Lys Gly Thr Tyr Asn Ala Lys Pro Gly Lys Tyr Tyr Leu Tyr Val
                85                  90                  95

Tyr Lys Tyr Glu Asn Lys Asp Gly Ser Tyr Val Leu Asn Ile Lys
            100                 105                 110
```

<210> SEQ ID NO 21

-continued

```
<211> LENGTH: 111
<212> TYPE: PRT
<213> ORGANISM: B. mycoides

<400> SEQUENCE: 21

Ser Val Glu Lys Glu Pro Asn Asn Ser Phe Gln Thr Ala Asn Lys Leu
1               5                   10                  15

Gln Leu Asn Gln Leu Leu Arg Ala Ser Leu Gly Asn Gly Asp Thr Ser
            20                  25                  30

Asp Tyr Phe Glu Ile Asn Val Glu Thr Ala Arg Asn Leu Gln Ile Asn
        35                  40                  45

Val Thr Lys Glu Asn Asn Ile Gly Val Asn Trp Val Leu Tyr Ser Ala
    50                  55                  60

Ala Asp Leu Asn Asn Tyr Val Thr Tyr Ala Gln Thr Gln Gly Asn Lys
65                  70                  75                  80

Leu Val Gly Ser Tyr Asn Ala His Pro Gly Lys Tyr Tyr Leu His Val
                85                  90                  95

Tyr Gln Tyr Gly Gly Gly Thr Gly Asn Tyr Thr Val Glu Val Lys
            100                 105                 110

<210> SEQ ID NO 22
<211> LENGTH: 112
<212> TYPE: PRT
<213> ORGANISM: B. weihensteph

<400> SEQUENCE: 22

Ala Val Glu Lys Glu Pro Asn Asn Ser Phe Asp Ala Ala Asn Pro Leu
1               5                   10                  15

Ser Leu Asn Ala Leu Leu Arg Gly Asn Leu Ser Asp Gln Asp Gln Val
            20                  25                  30

Asp Arg Phe Val Ile Asp Val Lys Asp Pro Lys Asp Leu Gln Ile Thr
        35                  40                  45

Val Thr Asn Glu Gln Asn Leu Gly Leu Asn Trp Val Leu Tyr Ser Glu
    50                  55                  60

Ser Asp Leu Asn Asn Tyr Val Thr Tyr Ala Thr Lys Arg Asp Gly Asn
65                  70                  75                  80

Lys Leu Leu Gly Asn Tyr Asn Ala Lys Pro Gly Lys Tyr Tyr Leu Ser
                85                  90                  95

Val Tyr Lys Tyr Gly Gly Gly Thr Gly Asn Phe Thr Val Glu Val Lys
            100                 105                 110

<210> SEQ ID NO 23
<211> LENGTH: 111
<212> TYPE: PRT
<213> ORGANISM: B. brevis

<400> SEQUENCE: 23

Glu Lys Glu Gln Glu Pro Asn Asn Ser Phe Ser Glu Ala Asn Pro Leu
1               5                   10                  15

Lys Ser Asn Val Glu Leu Ser Gly Gln Thr Ser Lys Gln Asp Asp Lys
            20                  25                  30

Asp Ile Phe Ala Leu Lys Val Leu Gly Asn Gly Thr Val Lys Ile Asn
        35                  40                  45

Val Thr Ser Glu His Asp Thr Gly Leu Asn Trp Val Val His His Glu
    50                  55                  60

Asp Asp Leu Asn Asn Tyr Leu Ala Tyr Pro Lys Thr Ser Gly Lys Thr
65                  70                  75                  80
```

```
Leu Ser Gly Glu Phe Glu Ala Thr Pro Gly Thr Tyr Tyr Leu Ser Val
                85                  90                  95

Tyr Asn Phe Asn Gly Glu Thr Ile Pro Tyr Lys Val Thr Ala Glu
            100                 105                 110

<210> SEQ ID NO 24
<211> LENGTH: 111
<212> TYPE: PRT
<213> ORGANISM: B. brevis

<400> SEQUENCE: 24

Pro Thr Glu Val Glu Pro Asn Asn Ser Phe Asp Asp Ala Asn Thr Leu
1               5                   10                  15

Gln Leu Gly Lys Glu Ile Ser Gly Gln Thr Asp Arg Thr Asp Asp Lys
            20                  25                  30

Asp Thr Tyr Met Ile Gln Val Glu Glu Glu Gly Val Ile Gln Val Thr
        35                  40                  45

Val Ser Ser Glu Lys Asp Glu Gly Leu Asn Trp Val Val Phe His Glu
    50                  55                  60

Asp Asp Leu Lys Thr Tyr Phe Ala Tyr Pro Lys Thr Thr Gly Lys Lys
65                  70                  75                  80

Leu Thr Gly Glu Phe Glu Ala Lys Pro Gly Lys Tyr Tyr Leu Leu Val
                85                  90                  95

Tyr Asn Thr Asn Asn Thr Lys Ile Pro Tyr Lys Ala Ile Val Asn
            100                 105                 110

<210> SEQ ID NO 25
<211> LENGTH: 112
<212> TYPE: PRT
<213> ORGANISM: C. perfringens

<400> SEQUENCE: 25

Ile Lys Glu Val Glu Asn Asn Asn Asp Phe Asp Lys Ala Met Lys Val
1               5                   10                  15

Asp Ser Asn Ser Lys Ile Val Gly Thr Leu Ser Asn Asp Asp Leu Lys
            20                  25                  30

Asp Ile Tyr Ser Ile Asp Ile Lys Asn Pro Ser Asp Leu Asn Ile Val
        35                  40                  45

Val Glu Asn Leu Asp Asn Ile Lys Met Asn Trp Leu Leu Tyr Ser Ala
    50                  55                  60

Asp Asp Leu Ser Asn Tyr Val Asp Tyr Ala Asn Ala Asp Gly Asn Lys
65                  70                  75                  80

Leu Ser Asn Thr Cys Lys Leu Asn Pro Gly Lys Tyr Tyr Leu Cys Val
                85                  90                  95

Tyr Gln Phe Glu Asn Ser Gly Thr Gly Asn Tyr Thr Val Asn Leu Gln
            100                 105                 110

<210> SEQ ID NO 26
<211> LENGTH: 115
<212> TYPE: PRT
<213> ORGANISM: C. sporogenes

<400> SEQUENCE: 26

Ile Ser Glu Lys Glu Asp Asn Asp Ser Phe Asp Lys Ala Asn Arg Val
1               5                   10                  15

Gly Lys Asn Gln Thr Val Leu Ala Thr Leu Asp Thr Lys Asp Asn Arg
            20                  25                  30

Asp Thr Tyr Tyr Phe Asp Ala Leu Ala Ala Arg Thr Ile Asp Ile Val
```

```
                35                  40                  45
Met Glu Asn Thr Asp Asn Ser Thr Ile Phe Asn Trp Leu Ala Tyr
        50                  55                  60
Ser Ser Asp Asn Thr Asn Asn Tyr Ile Gly Tyr Pro Thr Lys Lys Glu
65                  70                  75                  80
Gly Asn Lys Leu Met Gly Ser Phe Lys Val Pro Lys Pro Gly Arg Tyr
                85                  90                  95
Tyr Ile Leu Ala Tyr Lys Asn Ser Ser Asn Lys Ile Asn Tyr Lys Leu
            100                 105                 110
Thr Ile Asn
        115

<210> SEQ ID NO 27
<211> LENGTH: 115
<212> TYPE: PRT
<213> ORGANISM: C. botulinum

<400> SEQUENCE: 27

Ile Ser Glu Lys Glu Asp Asn Asn Ser Phe Asp Lys Ala Asn Arg Val
1               5                   10                  15
Cys Lys Asn Gln Ser Val Ile Ala Thr Leu Asp Thr Asn Asp Pro Arg
            20                  25                  30
Asp Thr Tyr Tyr Phe Asp Ala Leu Thr Ala Gly Asn Ile Glu Val Thr
        35                  40                  45
Met Gly Asn Thr Asp Asn Ser Ser Asn Glu Phe Asn Trp Leu Ala Tyr
    50                  55                  60
Ser Ser Asp Asn Thr Asn Asn Tyr Ile Gly Tyr Ala Thr Lys Arg Glu
65                  70                  75                  80
Gly Asn Lys Ile Thr Gly Asn Phe Lys Val Asp Lys Pro Gly Arg Tyr
                85                  90                  95
Tyr Ile Val Ala Tyr Lys Thr Ser Ser Asn Lys Ile Asn Tyr Lys Leu
            100                 105                 110
Asn Ile Lys
        115

<210> SEQ ID NO 28
<211> LENGTH: 115
<212> TYPE: PRT
<213> ORGANISM: C. sporogenes

<400> SEQUENCE: 28

Val Ser Glu Lys Glu Asp Asn Asn Asp Phe Thr Thr Ala Asn Pro Val
1               5                   10                  15
Tyr Tyr Lys Asp Leu Val Asn Gly Ser Val Ser Ser Ser Asp Asn Lys
            20                  25                  30
Asp Thr Phe Tyr Phe Thr Val Thr Lys Pro Ser Asp Ile Thr Ile Thr
        35                  40                  45
Val Glu Lys Thr Asn Asn Asp Lys Ser Glu Phe Asn Trp Leu Leu Phe
    50                  55                  60
Ser Asp Glu Asp Lys Ser Asn Tyr Met Ala Phe Pro Asn Lys Glu Leu
65                  70                  75                  80
Gly Asn Gln Leu Ser Asn Thr Val Lys Ile Asn Lys Pro Gly Lys Tyr
                85                  90                  95
Tyr Leu Val Ile Tyr Lys Thr Leu Gly Glu Lys Val Asp Tyr Lys Phe
            100                 105                 110
Ser Ile Glu
```

-continued

```
                115

<210> SEQ ID NO 29
<211> LENGTH: 115
<212> TYPE: PRT
<213> ORGANISM: C. botulinum

<400> SEQUENCE: 29

Val Ser Glu Lys Glu Asn Asn Asn Asp Tyr Val Asn Ala Asn Pro Val
1               5                   10                  15

Tyr Ser Lys Asp Leu Val Asn Gly Ser Val Ser Ser Asp Asp Arg
                20                  25                  30

Asp Ile Phe Tyr Phe Asn Val Thr Lys Pro Ser Asp Ile Thr Ile Asn
            35                  40                  45

Val Glu Lys Ile Asn Lys Asp Lys Ser Glu Phe Ser Trp Leu Leu Phe
    50                  55                  60

Ser Glu Glu Asp Lys Ser Asn Tyr Ile Thr Tyr Pro Asn Lys Glu Leu
65                  70                  75                  80

Glu Asn Leu Phe Tyr Ser Thr Val Lys Ile Asp Lys Pro Gly Lys Tyr
                85                  90                  95

Tyr Leu Val Ile Tyr Lys Val Ser Gly Glu Lys Ser Asp Tyr Arg Phe
            100                 105                 110

Asn Ile Glu
        115

<210> SEQ ID NO 30
<211> LENGTH: 113
<212> TYPE: PRT
<213> ORGANISM: C. sordellii

<400> SEQUENCE: 30

Gly Val Glu Gln Glu Asp Asn Asn Ser Phe Glu Lys Ala Asn Pro Phe
1               5                   10                  15

Ser Ile Asn Gln Leu Val Lys Gly Glu Leu Asn Asn Lys Asp Thr
                20                  25                  30

Ser Asp Tyr Phe Lys Phe Glu Val Lys Glu Asp Ala Gln Leu Asn Ile
            35                  40                  45

Ser Leu Glu Lys Thr Glu Gly Asp Gly Val Asn Trp Leu Leu Phe Lys
    50                  55                  60

Asp Ser Asp Leu Glu Asn Tyr Ile Ala Ser Pro Thr Glu Ser Ile Asp
65                  70                  75                  80

Asn Lys Leu Asn Gly Lys Val Asp Leu Lys Val Gly Thr Tyr Tyr Leu
                85                  90                  95

Glu Val Tyr Gly Tyr Gly Ser Ser Pro Val Lys Tyr Asn Phe Lys Val
            100                 105                 110

Thr

<210> SEQ ID NO 31
<211> LENGTH: 113
<212> TYPE: PRT
<213> ORGANISM: Clostridium histolyticum

<400> SEQUENCE: 31

Thr Lys Glu Met Glu Pro Asn Asp Asp Ile Lys Glu Ala Asn Gly Pro
1               5                   10                  15

Ile Val Glu Gly Val Thr Val Lys Gly Asp Leu Asn Gly Ser Asp Asp
                20                  25                  30
```

```
Ala Asp Thr Phe Tyr Phe Asp Val Lys Glu Asp Gly Asp Val Thr Ile
        35                  40                  45

Glu Leu Pro Tyr Ser Gly Ser Ser Asn Phe Thr Trp Leu Val Tyr Lys
    50                  55                  60

Glu Gly Asp Asp Gln Asn His Ile Ala Ser Gly Ile Asp Lys Asn Asn
65                  70                  75                  80

Ser Lys Val Gly Thr Phe Lys Ser Thr Lys Gly Arg His Tyr Val Phe
                85                  90                  95

Ile Tyr Lys His Asp Ser Ala Ser Asn Ile Ser Tyr Ser Leu Asn Ile
            100                 105                 110

Lys

<210> SEQ ID NO 32
<211> LENGTH: 113
<212> TYPE: PRT
<213> ORGANISM: C. perfringens

<400> SEQUENCE: 32

Ile Asn Glu Ser Glu Pro Asn Asn Asp Phe Glu Lys Ala Asn Gln Ile
1               5                   10                  15

Ala Lys Ser Asn Met Leu Val Lys Gly Thr Leu Ser Glu Glu Asp Tyr
            20                  25                  30

Ser Asp Lys Tyr Tyr Phe Asp Val Ala Lys Lys Gly Asn Val Lys Ile
        35                  40                  45

Thr Leu Asn Asn Leu Asn Ser Val Gly Ile Thr Trp Thr Leu Tyr Lys
    50                  55                  60

Glu Gly Asp Leu Asn Asn Tyr Val Leu Tyr Ala Thr Gly Asn Glu Gly
65                  70                  75                  80

Thr Val Leu Lys Gly Glu Lys Thr Leu Glu Pro Gly Arg Tyr Tyr Leu
                85                  90                  95

Ser Val Tyr Thr Tyr Asp Asn Gln Ser Gly Ala Tyr Thr Val Asn Val
            100                 105                 110

Lys

<210> SEQ ID NO 33
<211> LENGTH: 113
<212> TYPE: PRT
<213> ORGANISM: C. sordellii

<400> SEQUENCE: 33

Ser Gln Glu Val Gly Asn Asp Asp Thr Phe Glu Thr Ala Asn Gly Pro
1               5                   10                  15

Ile Lys Ile Asn Thr Asn Tyr Ser Gly Asp Leu Ser Asp Thr Asp Asn
            20                  25                  30

Lys Asp Tyr Tyr Tyr Phe Asn Leu Asp Asn Pro Ser Asn Ile Asn Ile
        35                  40                  45

Thr Leu Glu Asn Leu Asp Asn Lys Gly Ile Ser Trp Gln Leu Phe His
    50                  55                  60

Glu Ser Asp Leu Asn Asn Tyr Val Ala Tyr Pro Thr Thr Ser Gly Ala
65                  70                  75                  80

Ile Leu Asn Gly Asp Tyr Asn Ala Thr Lys Pro Gly Lys Tyr Tyr Ile
                85                  90                  95

Leu Val Tyr Asn His Asp Lys Ser Ile Ala Asn Tyr Asn Leu Lys Val
            100                 105                 110

Asn
```

<210> SEQ ID NO 34
<211> LENGTH: 111
<212> TYPE: PRT
<213> ORGANISM: Clostridium histolyticum

<400> SEQUENCE: 34

Gly Thr Glu Lys Glu Pro Asn Asn Ser Lys Glu Thr Ala Ser Gly Pro
1               5                   10                  15

Ile Val Pro Gly Ile Pro Val Ser Gly Thr Ile Glu Asn Thr Ser Asp
            20                  25                  30

Gln Asp Tyr Phe Tyr Phe Asp Val Ile Thr Pro Gly Glu Val Lys Ile
        35                  40                  45

Asp Ile Asn Lys Leu Gly Tyr Gly Gly Ala Thr Trp Val Val Tyr Asp
    50                  55                  60

Glu Asn Asn Asn Ala Val Ser Tyr Ala Thr Asp Asp Gly Gln Asn Leu
65                  70                  75                  80

Ser Gly Lys Phe Lys Ala Asp Lys Pro Gly Arg Tyr Tyr Ile His Leu
                85                  90                  95

Tyr Met Phe Asn Gly Ser Tyr Met Pro Tyr Arg Ile Asn Ile Glu
            100                 105                 110

<210> SEQ ID NO 35
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(30)
<223> OTHER INFORMATION: Any Xaa is hydroxyproline

<400> SEQUENCE: 35

Pro Xaa Gly Pro Xaa Gly Pro Xaa Gly Pro Xaa Gly Pro Xaa Gly Pro
1               5                   10                  15

Xaa Gly Pro Xaa Gly Pro Xaa Gly Pro Xaa Gly Pro Xaa Gly
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(30)
<223> OTHER INFORMATION: Any Xaa is hydroxyproline

<400> SEQUENCE: 36

Pro Xaa Gly Pro Xaa Gly Pro Xaa Gly Pro Xaa Gly Pro Xaa Gly Pro
1               5                   10                  15

Xaa Gly Pro Xaa Ala Pro Xaa Gly Pro Xaa Gly Pro Xaa Gly
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(30)

<223> OTHER INFORMATION: Any Xaa is hydroxyproline

<400> SEQUENCE: 37

Pro Xaa Gly Pro Xaa Gly Pro Xaa Gly Pro Xaa Gly Pro Xaa Gly Pro
1               5                   10                  15

Xaa Ala Pro Xaa Gly Pro Xaa Gly Pro Xaa Gly Pro Xaa Gly
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(30)
<223> OTHER INFORMATION: Any Xaa is hydroxyproline

<400> SEQUENCE: 38

Pro Xaa Gly Pro Xaa Gly Pro Xaa Gly Pro Xaa Gly Pro Xaa Ala Pro
1               5                   10                  15

Xaa Gly Pro Xaa Gly Pro Xaa Gly Pro Xaa Gly Pro Xaa Gly
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(30)
<223> OTHER INFORMATION: Any Xaa is hydroxyproline

<400> SEQUENCE: 39

Pro Xaa Gly Pro Xaa Gly Pro Xaa Gly Pro Xaa Ala Pro Xaa Gly Pro
1               5                   10                  15

Xaa Gly Pro Xaa Gly Pro Xaa Gly Pro Xaa Gly Pro Xaa Gly
            20                  25                  30

<210> SEQ ID NO 40
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(24)
<223> OTHER INFORMATION: Any Xaa is hydroxyproline

<400> SEQUENCE: 40

Pro Xaa Gly Pro Xaa Gly Pro Xaa Gly Pro Cys Gly Pro Xaa Gly Pro
1               5                   10                  15

Xaa Gly Pro Xaa Gly Pro Xaa Gly
            20

<210> SEQ ID NO 41
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature

```
<222> LOCATION: (1)..(31)
<223> OTHER INFORMATION: Any Xaa is hydroxyproline

<400> SEQUENCE: 41

Pro Xaa Gly Pro Xaa Gly Pro Xaa Gly Pro Xaa Gly Pro Xaa Ala Pro
1               5                   10                  15

Xaa Gly Pro Xaa Gly Pro Xaa Gly Pro Xaa Gly Pro Xaa Gly Cys
            20                  25                  30

<210> SEQ ID NO 42
<211> LENGTH: 22
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(22)
<223> OTHER INFORMATION: Any Xaa is hydroxyproline

<400> SEQUENCE: 42

Gly Pro Xaa Gly Pro Xaa Gly Pro Xaa Gly Pro Xaa Gly Pro Xaa Gly
1               5                   10                  15

Pro Xaa Gly Pro Xaa Gly
            20

<210> SEQ ID NO 43
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(31)
<223> OTHER INFORMATION: Any Xaa is hydroxyproline

<400> SEQUENCE: 43

Gly Pro Xaa Gly Pro Xaa Gly Pro Xaa Gly Pro Xaa Gly Pro Xaa Gly
1               5                   10                  15

Pro Xaa Gly Pro Xaa Gly Pro Arg Gly Pro Arg Gly Pro Arg Gly
            20                  25                  30

<210> SEQ ID NO 44
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(9)
<223> OTHER INFORMATION: Any Xaa is hydroxyproline

<400> SEQUENCE: 44

Pro Xaa Gly Pro Xaa Gly Pro Xaa Gly
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(9)
<223> OTHER INFORMATION: Any Xaa is hydroxyproline
```

```
<400> SEQUENCE: 45

Pro Xaa Gly Pro Xaa Gly Pro Xaa Ala
1               5

<210> SEQ ID NO 46
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(26)
<223> OTHER INFORMATION: Any Xaa is hydroxyproline

<400> SEQUENCE: 46

Gly Pro Arg Gly Pro Xaa Gly Pro Xaa Gly Pro Xaa Gly Pro Xaa Gly
1               5                   10                  15

Pro Xaa Gly Pro Xaa Gly Pro Xaa Gly Cys
            20                  25

<210> SEQ ID NO 47
<211> LENGTH: 7
<212> TYPE: PRT
<213> ORGANISM: Artificial Sequence
<220> FEATURE:
<223> OTHER INFORMATION: Synthetic peptide: GST Tag

<400> SEQUENCE: 47

Gly Ser Pro Gly Ile Pro Gly
1               5
```

DELIVERY OF THERAPEUTIC AGENTS BY A COLLAGEN BINDING PROTEIN

CROSS-REFERENCE TO RELATED APPLICATIONS

This patent application is a continuation application of U.S. application Ser. No. 15/407,589, filed Jan. 17, 2017 which is a divisional application of U.S. application Ser. No. 14/365,226, filed Jun. 13, 2014, which is a national stage filing under 35 U.S.C. 371 of International Application No. PCT/US2012/069831, filed Dec. 14, 2012, which claims the benefit of priority of U.S. Provisional Patent Application No. 61/570,620, filed Dec. 14, 2011 and of U.S. Provisional Patent Application No. 61/596,869, filed Feb. 9, 2012, all of which are incorporated herein by reference in their entireties.

This patent application is a also a divisional application of U.S. application Ser. No. 15/386,626 filed Dec. 21, 2016 and issuing on Feb. 26, 2019 as U.S. Pat. No. 10,213,488, which application is a division of U.S. patent application Ser. No. 14/378,067 filed Aug. 11, 2014 (U.S. Pat. No. 9,526,765, issued Dec. 27, 2016), which application is a national stage filing under 35 U.S.C. 371 of International Application No. PCT/US2013/025541, filed Feb. 11, 2013, which claims the benefit of priority of U.S. Provisional Patent Application No. 61/596,869, filed Feb. 9, 2012, and of International Application No. PCT/US2012/069831, filed Dec. 14, 2012, all of which are incorporated herein by reference in their entireties.

STATEMENT REGARDING FEDERALLY SPONSORED RESEARCH

This invention was made with United States government support awarded by the National Institutes of Health grant number NCRR COBRE 8P30GM103450 and INBRE GM103429. The United States may have certain rights in this invention.

SEQUENCE LISTING

A Sequence Listing accompanies this application and is incorporated herein by reference in its entirety. The Sequence Listing was filed with the application as a text file on Dec. 14, 2012.

INTRODUCTION

Delivery of therapeutic agents to sites within the body of a subject where a particular therapeutic agent is needed in order to be effective is a developing area. Such delivery systems will allow more efficient use of therapeutic agents while reducing toxicity caused by some therapeutic agents. Use of targeted liposomes or polypeptides, such as antibodies, to target therapeutic agents to particular sites within the body has proved successful, but additional delivery agents are needed.

Alopecia (hair loss) is a psychologically and emotionally distressing event with multiple causes. Alopecia occurs most commonly in male-pattern baldness, affecting approximately two thirds of males by age 35; a similar pattern of hair loss can be observed in females with polycystic ovarian syndrome. In both of these disorders, the hair loss is androgen mediated. Alopecia can also occur as an autoimmune disease, termed alopecia areata; a disorder which affects 1.7% of the population. It can occur as a side-effect of medical treatments, particularly in chemotherapy, with 65-85% of chemotherapy patients experiencing some degree of alopecia. Psychological consequences of hair loss have been well studied in the chemotherapy setting. Chemotherapy-induced alopecia (CIA) can result in anxiety, depression, a negative body image, lowered self-esteem and a reduced sense of well-being. In fact, 47-58% of female cancer patients consider hair loss to be the most traumatic aspect of chemotherapy, and 8% would decline treatment for fear of hair loss. In addition to these studies in chemotherapy patients, evidence exists in other forms of alopecia to support therapy to reduce psychological consequences of hair loss. Thus a new treatment to stop hair loss or speed hair regrowth would be beneficial.

While drugs with mild anti-androgenic effects (i.e. spironolactone) had been used with limited success as therapy for alopecia, the first effective medication for alopecia was minoxidil (Rogaine). This antihypertensive has an observed side-effect of causing hair growth, and is now used as topical therapy for many forms of alopecia. However, responses are incomplete, with some subjects showing only slowing of hair loss rather than actual regrowth. Finasteride (Propecia) is a newer agent that blocks conversion of testosterone to dihydrotestosterone, resulting in improvements in androgenic alopecia at the expense of partial systemic androgen blockade. However, response rates with long-term (10 years) therapy are only around 50%. Overall, despite considerable research in this area, there is still no adequate therapy for hair loss.

In addition, unwanted hair growth is a cosmetic issue many people deal with on a regular basis. Unwanted hair growth on the face, legs, arms, chest or back is a growing cosmetic problem. Many people use laser therapy, waxing or other therapies to remove unwanted hair. There are currently no topical pharmaceuticals to limit hair growth.

Collagenopathies represent a large number of diseases in which collagen structure or formation is not normal. This group of diseases results in a broad spectrum of symptoms including bone defects, vascular defects, and skin defects. Many of these diseases have no or only ineffective treatments available.

For example, osteogenesis imperfecta (OI), also known as brittle bone disease, is caused by an inborn mutation of type I collagen. Approximately 25,000 to 50,000 Americans are affected and the effects of the disease range from mild, in which many individuals are unaware of the disease, to severe in which individuals cannot live a normal life due to recurrent broken bones. Most OI patients carry a mutation which causes an amino acid change in collagen changing a glycine to a bulkier amino acid which results in disruption of the triple helix structure of the collagen and under-twisting. The body may respond by hydrolyzing the collagen and this may result in a reduction in bone strength. There is currently no cure and few treatments for OI.

SUMMARY

Provided herein are methods of delivering therapeutic agents by administering compositions including a bacterial collagen-binding polypeptide segment linked to the therapeutic agent to subjects in need of treatment with the therapeutic agent. In these methods, the therapeutic agent is not a PTH/PTHrP receptor agonist or antagonist, basic fibroblast growth factor (bFGF) or epidermal growth factor (EGF) and the bacterial collagen-binding polypeptide segment delivers the agent to sites of partially untwisted or under-twisted collagen.

In another aspect, methods of treating a subject with a collagenopathy, such as osteogenesis imperfecta, by administering a composition comprising a bacterial collagen-binding polypeptide segment linked to a PTH/PTHrP receptor agonist to a subject in an amount effective to treat the collagenopathy are provided. The bacterial collagen-binding polypeptide segment delivers the agent to sites of partially untwisted or under-twisted collagen.

In yet another aspect, methods of treating hyperparathyroidism by administering a composition comprising a bacterial collagen-binding polypeptide segment linked to a PTH/PTHrP receptor agonist to a subject are provided.

In still a further aspect, methods of slowing hair growth or regrowth after removal by administering a composition comprising a bacterial collagen-binding polypeptide segment linked to a PTH/PTHrP receptor antagonist to a subject are provided.

In a still further aspect, methods of increasing hair growth or the speed of hair re-growth after removal or loss by administering a composition comprising a bacterial collagen-binding polypeptide segment linked to a PTH/PTHrP receptor agonist to a subject are provided.

BRIEF DESCRIPTION OF THE DRAWINGS

FIG. 1 is a sequence alignment showing the alignment of several M9B bacterial collagenases from the *Bacillus* and *Clostridium* families. The residues shown in blue are important for collagen binding activity, those shown in green are important for maintaining the architecture or protein folding. Both of these are also underlined for the top and bottom sequences. Residues shown in red are critical for $Ca^{2+}$ binding and those in orange are critical for positioning the $Ca^{2+}$ binding residues. The sequences are also included in the Sequence Listing filed herewith as SEQ ID NOs: 13-34, where SEQ ID NO: 13 is the first listed ColG s3b sequence and SEQ ID NO: 34 is the ColH s3 sequence.

FIG. 2 is a set of drawings showing the chemical structures of synthesized peptides.

FIG. 5A shows an overlay of $^1$H-$^{15}$N HSQC spectrum of CBD (black) and $^1$H-$^{15}$N HSQC spectrum of [(POG)$_{10}$]$_3$:CBD complex (green) at 1:1 ratio. Amide resonance of V973, G975 and S979 are present during this titration. FIG. 5B shows an overlay of $^1$H-$^{15}$N HSQC spectrum of CBD (black) and $^1$H-$^{15}$N HSQC spectrum of [PROXYL-(POG)$_6$POA(POG)$_3$]$_3$:CBD complex (red) at 1:1 ratio. Amide resonances of V973, G975 and S979 disappeared because of their proximity to the spin-labeled group. FIG. 5C is a cartoon showing the structure of CBD and the CBD residues that are line broadened upon titration with [PROXYL-(POG)$_6$POA(POG)$_3$]$_3$.

FIG. 6A shows an overlay of $^1$H-$^{15}$N HSQC spectrum of CBD (black) and $^1$H-$^{15}$N HSQC spectrum of [(POG)$_{10}$]$_3$:CBD complex (green) at 1:1 ratio. Amide resonances of Q972, V973, G975 and S979 are present during this titration. FIG. 6B shows an overlay of $^1$H-$^{15}$N HSQC spectrum of CBD (black) and $^1$H-$^{15}$N HSQC spectrum of [PROXYL-(POG)$_5$POA(POG)$_4$]$_3$:CBD complex (red) at ratio 1:1. Amide resonances of Q972, V973, G975 and S979 are line broadened due to the PROXYL moiety. FIG. 6C is a cartoon of the structure of CBD showing the CBD residues that are uniquely line broadened upon titration with [PROXYL-(POG)$_5$POA(POG)$_4$]$_3$. FIG. 6D shows an overlay of $^1$H-$^{15}$N HSQC spectrum of CBD (black) and $^1$H-$^{15}$N HSQC spectrum of [(POG)$_{10}$]$_3$:CBD complex (green) at 1:1 ratio. Amide resonances of L946, Q972, V973, G975 and S979 are present during this titration. FIG. 6E shows an overlay of $^1$H-$^{15}$N HSQC spectrum of CBD (black) and $^1$H-$^{15}$N HSQC spectrum of [PROXYL-(POG)$_4$POA (POG)$_5$]$_3$:CBD complex (red) at 1:1 ratio. Amide resonances of L946, Q972, V973, G975 and S979 disappeared because of the spin-label. FIG. 6F shows an overlay of $^1$H-$^{15}$N HSQC spectrum of CBD (black) and $^1$H-$^{15}$N HSQC spectrum of [(POG)$_4$POA(POG)$_5$]$_3$:CBD (cyan) at ratio 1:1. In the absence of spin label, amide resonances of L946, Q972, V973, G975 and S979 are not line broadened. FIG. 6G shows an overlay of $^1$H-$^{15}$N HSQC spectrum of CBD (black) and $^1$H-$^{15}$N HSQC spectrum of [(POG)$_{10}$]$_3$:CBD complex (green) at 1:1 ratio. Amide resonances of L946, G953, Q972, V973, D974, G975, N976, V978, S979 are present during this titration. FIG. 6H shows an overlay of $^1$H-$^{15}$N HSQC spectrum of CBD (black) and $^1$H-$^{15}$N HSQC spectrum of [PROXYL-(POG)$_3$POA(POG)$_6$]$_3$:CBD complex (red) at ratio 1:1. Amide resonances of L946, G953, Q972, V973, D974, G975, N976, V978, S979 are line broadened due to the PROXYL moiety. FIG. 6I is a cartoon of the structure of CBD showing the CBD residues that are line broadened by the spin label of [PROXYL-(POG)$_3$POA (POG)$_6$]$_3$.

FIG. 8A to FIG. 8H are a set of plots showing HSQC NMR data obtained using the CBD—collagenous peptide interactions. FIG. 8A shows an overlay of $^1$H-$^{15}$N HSQC spectrum of CBD (black) and $^1$H-$^{15}$N HSQC spectrum of [(POG)$_{10}$]$_3$:CBD complex (green) at 1:1 ratio. Amide resonances of S906, S997 and G998 are present during this titration. FIG. 8B shows an overlay of $^1$H-$^{15}$N HSQC spectrum of CBD (black) and $^1$H-$^{15}$N HSQC spectrum of [(POG)$_4$POA(POG)$_5$C-PROXYL]$_3$:CBD complex (red) at ratio 1:1. Amide resonances of S906, S997 and G998 are line broadened due to the PROXYL moiety. FIG. 8C shows an overlay of $^1$H-$^{15}$N HSQC spectrum of CBD (black) and $^1$H-$^{15}$N HSQC spectrum of [(POG)$_4$POA(POG)$_5$C-carbamidomethyl]$_3$:CBD (cyan) at 1:1 ratio. In the absence of spin label, amide resonances of S906, S997 and G998 are not line broadened. FIG. 8D is a cartoon of the structure of CBD showing the CBD residues that are line broadened due to the spin label of $[(POG)_4POA(POG)_5C$-PROXYL$]_3$. Amide resonances of S906, S997 and G998 (red) disappeared upon titration with $[(POG)_4POA(POG)_5$-PROXYL$]_3$. FIG. 8E shows an overlay of $^1$H-$^{15}$N HSQC spectrum of CBD (black) and $^1$H-$^{15}$N HSQC spectrum of $[(POG)_{10}]_3$:CBD complex (green) at 1:1 ratio. Amide resonances of S906, Q972, V973, G975, S979, S997 and G998 are present during this titration. FIG. 8F shows an overlay of $^1$H-$^{15}$N HSQC spectrum of CBD (black) and $^1$H-$^{15}$N HSQC spectrum of [11PROXYL-$(POG)_3PCG(POG)_4]_3$:CBD complex (red) at 1:1 ratio. Amide resonances of S906, Q972, V973, G975, S979, S997 and G998 disappeared because of the spin-label. FIG. 8G shows an overlay of $^1$H-$^{15}$N HSQC spectrum of CBD (black) and $^1$H-$^{15}$N HSQC spectrum of $[(POG)_3PCG (POG)_4]_3$:CBD (cyan) at ratio of 1:1. Resonances of S906, Q972, V973, G975, S979, S997 and G998 are intact in the absence of the spin label. FIG. 8H is a cartoon of the structure of CBD showing the residues that are line broadened upon titration with [11PROXYL-$(POG)_3PCG (POG)_4]_3$. Only amide resonances of S906, R929, S997, and G998 (red) disappeared at 0.2:1 ratio. When the peptide ratio was raised to 0.3:1, additional resonances of V973, G975, S979 (blue) disappeared.

FIG. 9G and FIG. 9H show two probable binding modes of [11PROXYL-$(POG)_3PCG(POG)_4]_3$::CBD complex.

FIG. 10A is an overlay of $^1$H-$^{15}$N HSQC spectrum of [POGPO-$^{15}$N-G-$(POG)_8]_3$ (black) with $^1$H-$^{15}$N HSQC spectrum of [POGPO-$^{15}$N-G-$(POG)_8]_3$:CBD complex (red) at 1:1 ratio. FIG. 10B shows an overlay of $^1$H-$^{15}$N HSQC spectrum of [POGPO-$^{15}$N-G-$(POG)_2$-POA-$(POG)_5]_3$ (black) with $^1$H-$^{15}$N HSQC spectrum of [POGPO-$^{15}$N-G-$(POG)_2$-POA-$(POG)_5]_3$:CBD complex (red) at 1:1 ratio. FIG. 10C shows an overlay of $^1$H-$^{15}$N HSQC spectrum of $[(POG)_8$-PO-$^{15}$N-G-POG$]_3$ (black) with $^1$H-$^{15}$N HSQC spectrum of $[(POG)_8$-PO-$^{15}$N-G-POG$]_3$:CBD complex (red) at 1:1 ratio. FIG. 10D shows an overlay of $^1$H-$^{15}$N HSQC spectrum of $[(POG)_4$-POA-PO-$^{15}$N-G-POG$]_3$ (black) with $^1$H-$^{15}$N HSQC spectrum of $[(POG)_4$-POA-PO-$^{15}$N-G-POG$]_3$:CBD complex (red) at 1:1 ratio.

FIG. 13 is a set of photographs showing the histology at Day 36 after the indicated treatment. Skin samples were taken from the dorsal region and processed for Hematoxylin and Eosin (H&E) staining. Representative sections are shown from each treatment group as indicated. (Antagonist=PTH(7-33)-CBD, Agonist=PTH-CBD).

FIG. 15 is a set of photographs showing the hair growth on the back of the mice after each of the indicated treatments and a graph showing the results of a grey scale analysis of the hair at the injection site over time after the injection.

FIG. 17 is a set of photographs and a graph showing the grey scale analysis of hair growth on the backs of mice comparing the indicated treatments with the PTH-CBD being administered prior to the chemotherapy as opposed to after chemotherapy began.

DETAILED DESCRIPTION

Figure 3A:
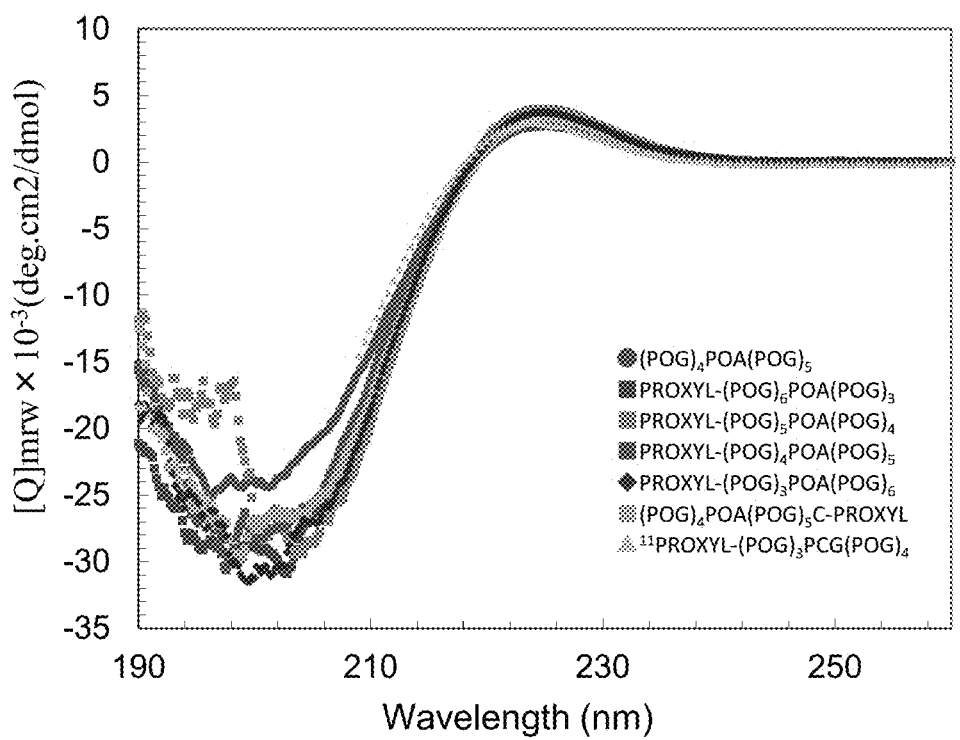
FIG. 3A is a graph showing the circular dichroism spectra of the collagenous peptides measured at 4° C.

Methods of delivering a therapeutic agent by administering a composition comprising a bacterial collagen-binding polypeptide segment linked to a therapeutic agent to a subject in need of treatment with the therapeutic agent are provided herein. In this embodiment, the therapeutic agent is not a PTH/PTHrP receptor agonist or antagonist and is not a bFGF or EGF polypeptide. The bacterial collagen-binding polypeptide segment delivers the therapeutic agent to sites of partially untwisted or under-twisted collagen.

In addition, methods of treating collagenopathies, such as osteogenesis imperfecta (OI), by administering a composition comprising a bacterial collagen-binding polypeptide segment linked to a PTH/PTHrP receptor agonist to a subject in need of treatment for a collagenopathy are provided. Collagenopathies include but are not limited to osteogenesis imperfecta, Stickler's syndrome, Ehlers-Danlos syndrome, Alport's syndrome, Caffey's disease, and localized collagen or cartilage damage. Many of these diseases are caused by genetic defects that result in the collagen in certain tissues being under twisted or partially untwisted.

For example, individuals with OI carry a mutation which causes an amino acid change in collagen changing a glycine to a bulkier amino acid which results in disruption of the triple helix structure of the collagen and under-twisting of the collagen. In the Examples, we demonstrate that the bacterial collagen-binding polypeptides described herein target and bind to these areas of under-twisted collagen. Thus, use of the collagen-binding polypeptides described herein to deliver a therapeutic agent capable of treating OI to the sites of under-twisted collagen may allow more effective treatment.

The collagen-binding polypeptide segment and the therapeutic agent may be chemically cross-linked to each other or may be polypeptide portions of a fusion protein. The terms "fusion protein" and "fusion polypeptide" may be used to refer to a single polypeptide comprising two functional segments, e.g., a collagen-binding polypeptide segment and a polypeptide based therapeutic agent, such as PTH/PTHrP receptor agonist polypeptide segment. The fusion proteins may be any size, and the single polypeptide of the fusion protein may exist in a multimeric form in its functional state, e.g., by cysteine disulfide connection of two monomers of the single polypeptide. A polypeptide segment may be a synthetic polypeptide or a naturally occurring polypeptide. Such polypeptides may be a portion of a polypeptide or may comprise one or more mutations. The two polypeptide segments of the fusion proteins can be linked directly or indirectly. For instance, the two segments may be linked directly through, e.g., a peptide bond or chemical cross-linking, or indirectly, through, e.g., a linker segment or linker polypeptide. The peptide linker may be any length and may include traditional or non-traditional amino acids. For example, the peptide linker may be 1-100 amino acids long, suitably it is 5, 10, 15, 20, 25 or more amino acids long such that the collagen binding portion of the fusion polypeptide can mediate collagen binding and the therapeutic agent can have its therapeutic effect. Peptide linkers may include but are not limited to a PKD (polycystic kidney disease) domain from a collagenase or other protein such as in SEQ ID NO: 2, a GST or His-tag, or a Ser or Gly linker.

The collagen-binding polypeptide segment is a polypeptide that binds collagen and may be part of a larger fusion protein, bioactive agent, or pharmaceutical agent. Determination of whether a composition, polypeptide segment, fusion protein, or pharmaceutical or bioactive agent binds collagen can be made as described in U.S. Patent Publication No. 2010/0129341, which is incorporated herein by reference in its entirety. Briefly, it is incubated with collagen in binding buffer, and the mixture is then filtered through a filter that would otherwise allow it to pass through but that blocks the collagen and therefore holds back materials that bind to the collagen. The filtrate is then assayed for the presence of the composition, polypeptide segment, fusion protein, or pharmaceutical or bioactive agent. Suitably, at least 80%, 85%, 90%, 95%, 98% or more suitably at least 99% of the collagen-binding composition, polypeptide segment, fusion protein, or pharmaceutical or bioactive agent is retained by the filter in this assay, as compared to when the filtration is performed without collagen.

The collagen-binding polypeptide segment may be a bacterial collagen-binding polypeptide segment. It may be a *Clostridium* collagen-binding polypeptide segment. The collagen-binding polypeptide segment may be a segment of a collagenase, or a bacterial collagenase, or a *Clostridium* collagenase. Suitably the polypeptide segment is only a portion of the collagenase and the collagen-binding polypeptide segment does not have collagenase activity. The collagen-binding polypeptide may be a bacterial M9B (including those derived from *Bacillus* spp. and *Clostridium* spp.) or M9A (including those derived from *Vibrio* spp.) collagen-binding protein or a collagen-binding peptide derived from such a protein. By "derived from" we mean that the peptide is a fragment of the full-length protein, a peptide that has amino acid changes relative to the wild-type protein or a combination thereof. The key is that the peptide retains the ability to bind collagen. For example, a peptide may be derived from a protein by selecting a region of the protein capable of binding to collagen. Compositions including a bacterial collagenase as a collagen binding peptide are described in US Patent Publication No. 2010/0129341, which is hereby incorporated herein by reference in its entirety.

Figure 1:
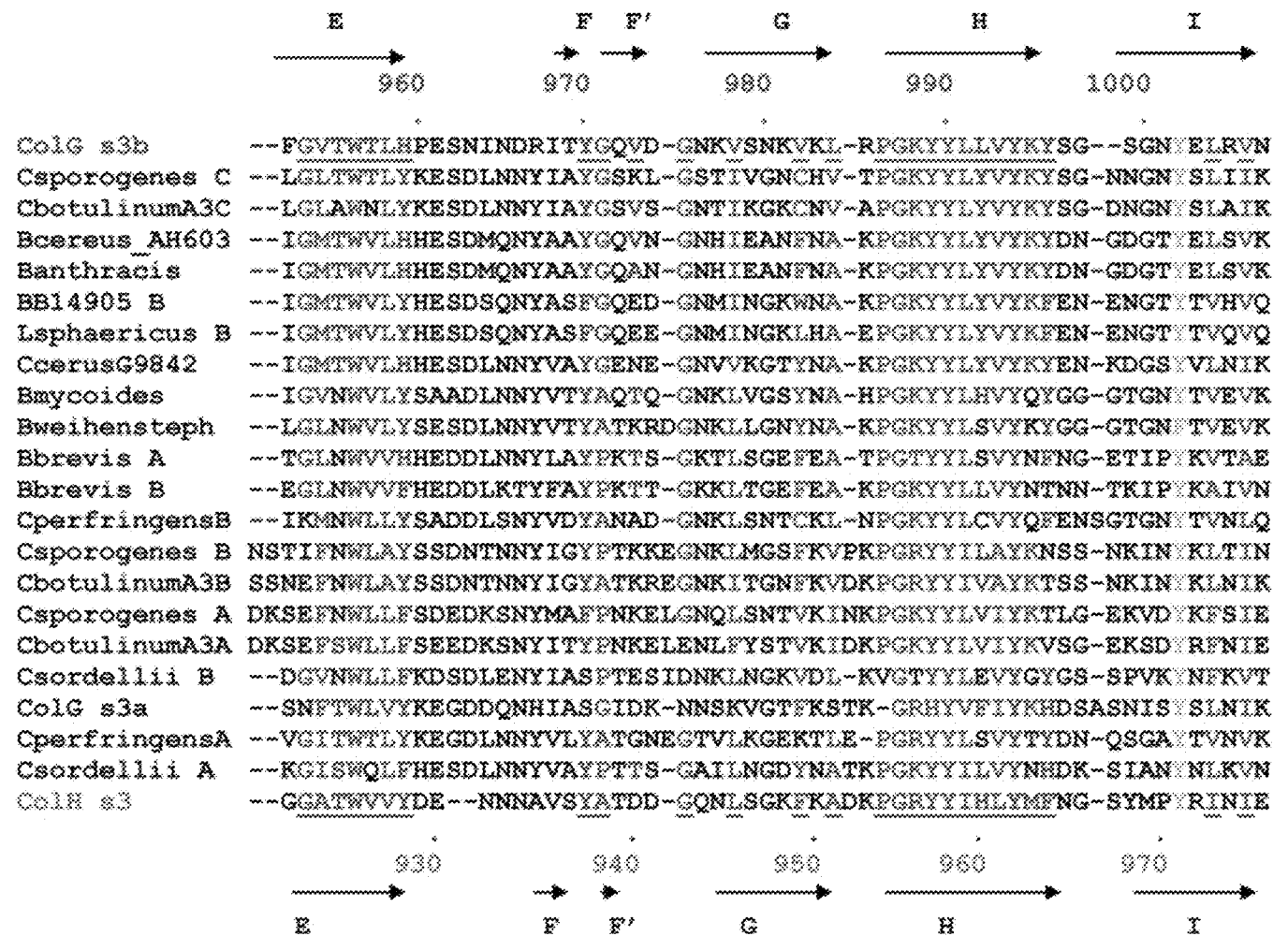

FIG. 1 shows a sequence alignment of the collagen-binding region of several M9B bacterial collagen-binding proteins included as SEQ ID NOs: 13-34. As can be seen from the sequence alignment, these proteins have a relatively small amount of sequence identity (about 30%), but they all bind to collagen in a similar fashion and are believed to have similar conformation as discussed in the Examples. Thus any of the peptides shown in FIG. 1 or collagen-binding fragments thereof can be used in the compositions and methods described herein. In FIG. 1, the amino acid residues critical for the conformation of the peptide and for the collagen-binding activity are underlined and shown in green and blue respectively. The key amino acid residues for collagen-binding are a tyrosine or phenylalanine at position 970 of ColG, position 977 of the ColH sequence of SEQ ID NO:1 (position 937 in FIG. 1) or a similar position of one of the sequences shown in FIG. 1; a tyrosine at position 994 of ColG, position 1000 of the ColH sequence of SEQ ID NO:1 (position 962 in FIG. 1) or a similar position of one of the sequences shown in FIG. 1; a tyrosine, phenylalanine or histidine at position 996 of ColG, position 1002 of the ColH sequence of SEQ ID NO:1 (position 964 in FIG. 1) or a similar position of one of the sequences shown in FIG. 1. Thus a peptide with relatively low sequence identity, sharing the structure and function of the ColG protein may also be used as a collagen binding domain (CBD) herein.

In one embodiment, the collagenase is ColH, SEQ ID NO: 6. The collagen-binding polypeptide segment may be or may include residues 901-1021 of SEQ ID NO:6 (residues 34-158 of SEQ ID NO:1), or a fragment of residues 34-158 of SEQ ID NO:1 at least 8, 10, 12, 15, 20, 25, 30, 40, 50, 60, 70, 80, 90, 100, 110 or 120 amino acid residues in length. The collagen-binding polypeptide segment is at least 50%, 60%, 70%, 80%, or at least 85%, at least 90%, at least 95%, at least 96%, at least 98%, or at least 99% identical to residues 34-158 of SEQ ID NO: 1. The collagen-binding polypeptide segment may be or may include residues 807-1021 of SEQ ID NO:6 (residues 37-251 of SEQ ID NO:2), or a fragment of residues 807-1021 of SEQ ID NO:6 at least 8, 10, 12, 15, 20, 25, 30, 40, 50, 60, 70, 80, 90, 100, 110 or 120 amino acid residues in length. Residues 807-901 comprise the polycystic kidney disease (PKD) domain of the collagen-binding protein. Those of skill in the art will appreciate that other linkers could be used to link the collagen-binding peptide to a therapeutic agent as outlined above. The collagen-binding polypeptide segment may be or may comprise a fragment of residues 901-1021 of SEQ ID NO:6, e.g., a fragment of at least 8, at least 10, at least 20, at least 30 at least 40, or at least 50 consecutive amino acid residues of residues 901-1021 of SEQ ID NO:6. Suitably the collagen-binding polypeptide consists of residues 894-1008, 894-1021, 901-1021, or 901-1008 of SEQ ID NO: 6 or a homolog thereof as shown by the sequence alignment in FIG. 9.

Among other proteins the collagen-binding segment can be derived from are ColG (Matsushita et al., (1999) J. Bacteriol. 181:923-933), a class I collagenase from *Clostridium histolyticum*. ColH is a class II collagenase (Yoshihara et al., (1994) J. Bacteriol. 176: 6489-6496). The collagen-binding polypeptide segment may also be a polypeptide segment from any one of the protein sequences provided in FIG. 1 which aligns collagen-binding peptides from members of *Clostridium* and *Bacillus*. Those of skill in the art will appreciate that other members of this collagen-binding protein family may be useful in the methods described herein.

The therapeutic agents linked to the collagen-binding polypeptide may be any suitable pharmaceutical or other active agent, including but not limited to, osteogenic promoters, antimicrobials, anti-inflammatory agents, polypeptides such as recombinant proteins, cytokines or antibodies, small molecule chemicals or any combination thereof. Suitably the therapeutic agents are capable of promoting bone growth, decreasing inflammation, promoting collagen stability. Suitably, the therapeutic agent is one whose therapeutic effect is in the region of collagen or damaged collagen. The therapeutic agent may include, but is not limited to, bone morphogenic protein (BMP), G-CSF, FGF, BMP-2, BMP-3, FGF-2, FGF-4, anti-sclerostin antibody, growth hormone, IGF-1, VEGF, TGF-β, KGF, FGF-10, TGF-α, TGF-β1, TGF-β receptor, CT, GH, GM-CSF, EGF, PDGF, celiprolol, activins and connective tissue growth factors. In alternative embodiments, the active agent may be a PTH/PTHrP receptor agonist or antagonist.

Bone loss due to a collagenopathy such as osteogenesis imperfecta, Stickler's syndrome or others which put an individual at higher risk for a bone fracture due to a collagen defect could be treated by administration of a bone anabolic peptide. The CBD may target the bone anabolic agents to sites where the collagen is malformed and thus may prevent fracture.

Vascular fragility due to defects such as Ehlers-Danlos syndrome type IV, Alport's syndrome or other diseases where blood vessel rupture is more likely due to a defect in collagen formation may be administered peptides that stimulate vascular growth or repair. The CBD will target the peptide to the areas having collagen damage and these areas are likely to have damaged vessels. The therapeutic agents will stimulate growth and repair at the site of damage and prevent vessel rupture.

Skin fragility due to disorders such as Ehlers-Danlos syndrome, Caffey's disease or other diseases where weakening of the skin due to a collagen defect leads to hyperelasticity, easy bruising or poor wound healing. Dermal and epidermal growth factors may serve as therapeutic agents which when linked to CBD and delivered to areas of damaged collagen will stimulate growth and repair of the skin, preventin striae and improving healing.

Collagen defects may also lead to cartilage malformation or insufficiency. Cartilage growth factors could be delivered locally to sites of damaged cartilage to aid in repair and restore function.

The PTH/PTHrP receptor agonist polypeptide segment may be a synthetic polypeptide or a naturally occurring polypeptide. Such polypeptides may be a portion of a polypeptide or may comprise one or more mutations. The mutations may make the PTH/PTHrP receptor agonist a better or worse agonist as compared to the wild-type PTH/PTHrP. Agonist activity with the PTH/PTHrP receptor can be assayed as described in Example 3 below by a cAMP stimulation assay. An agonist will stimulate cAMP synthesis in the assay described. Suitably, an agonist can activate receptor activity at least 10%, 20%, 30%, 40%, 50%, 60%, 70%, 80%, 90%, 100% or even 110% or 120% as much as wild-type PTH(1-34).

The PTH/PTHrP receptor agonist polypeptide segment is a PTH or PTHrP polypeptide segment. One human isoform of PTH is SEQ ID NO:7. One human isoform of PTHrP is SEQ ID NO:8. While the human isoforms are provided, those of skill in the art will appreciate that other non-human-derived isoforms may be used as well. Such non-human-derived isoforms may be able to interact with human PTH/PTHrP receptor and vice versa. The PTH/PTHrP receptor agonist polypeptide segment may be or may include residues 1-33 of SEQ ID NO:1 (residues 1-33 of PTH (SEQ ID NO:7)). The PTH/PTHrP receptor agonist polypeptide segment may be or may include residues 1-34 of PTH (SEQ ID NO:7). In other embodiments, it is a fragment of residues 1-34 of PTH (SEQ ID NO:7). In other embodiments, the PTH/PTHrP receptor agonist polypeptide segment may be or may include residues 1-84 of PTH (SEQ ID NO:7). In other embodiments, the PTH/PTHrP receptor agonist polypeptide segment may be or may include residues 1-14 of PTH (SEQ ID NO:7). In still other embodiments, the PTH/PTHrP receptor agonist is a PTH or PTHrP polypeptide segment for any other species.

The PTH/PTHrP receptor antagonist can include in one embodiment PTH(7-34), i.e., residues 7-34 of PTH (SEQ ID NO:7). In another embodiment, it is or includes residues 7-33 of PTH (SEQ ID NO:7). In other embodiments, it is a fragment of residues 7-34 of SEQ ID NO: 8. In another embodiment, the PTH/PTHrP receptor antagonist includes PTH(7-14), i.e., residues 7-14 of PTH (SEQ ID NO:7). In another embodiment, the PTH/PTHrP receptor antagonists include ((−1)-33) of PTH/PTHrP. In another embodiment, the PTH/PTHrP receptor antagonists include residues 1-14 of PTH with an N-terminal extension. Adding an N-terminal extension to PTH or active N-terminal fragments of PTH converts the PTH peptides to antagonists. The N-terminal extension can be 1, 2, 3, 4, 5, or more amino acids in length. The identity of the amino acids in the N-terminal extension is typically not important. In one embodiment, the PTH/PTHrP receptor antagonist includes residues 1-33 of PTH with a Gly-Ser extension at the N-terminus (SEQ ID NO:11). In another embodiment, the PTH/PTHrP receptor antagonist includes PTHrP(7-34), i.e., residues 7-34 of SEQ ID NO:8, or a fragment of residues 7-34 of SEQ ID NO:8. In another embodiment, the PTH/PTHrP receptor antagonist includes mouse TIP(7-39) (See Hoare S R, Usdin T B. 2002. Specificity and stability of a new PTH1 receptor antagonist, mouse TIP(7-39). Peptides 23:989-98). Other PTH/PTHrP receptor antagonists that may be used in the fusion proteins are also disclosed in Hoare et al. The PTH/PTHrP receptor antagonist may be a fragment of at least 8, 10, 12 or more amino acids from residues 1-34 of SEQ ID NO:7. In other embodiments the PTH/PTHrP receptor antagonist may be PTH/PTHrP receptor antagonist polypeptide from another species.

In one embodiment, the therapeutic agent or PTH/PTHrP receptor agonist or antagonist polypeptide segment is N terminal to the collagen-binding polypeptide segment in the fusion protein. That is, the two polypeptide segments each have an N-terminal and a C-terminal, and the N-terminal of the collagen-binding polypeptide segment is linked directly or indirectly, e.g., through a linker polypeptide segment (such as PKD, a Glycine or Serine linker) to the C-terminal of the therapeutic agent or PTH/PTHrP agonist or antagonist polypeptide segment.

The fusion proteins described above comprising (a) a collagen-binding polypeptide segment linked to (b) a therapeutic agent or a PTH/PTHrP receptor agonist or antagonist polypeptide segment can be replaced by pharmaceutical agents comprising (a) a collagen-binding polypeptide segment linked to (b) a therapeutic agent or PTH/PTHrP receptor agonist or a non-peptidyl PTH/PTHrP receptor agonist. An example of a non-peptidyl PTH/PTHrP receptor agonist is compound AH3960 (Rickard et al., (2007) Bone 39:1361-1372).

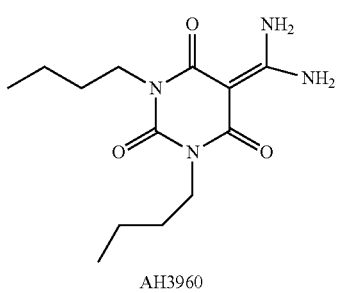

AH3960

AH3960 contains two amino groups. Amino groups in small chemical molecules such as AH3960 can be used to cross-link the therapeutic agent to amino groups on the collagen-binding polypeptide segment through a cross-linker such as DSG (disuccinimidyl glutarate) or through the combination of SANH (succinimidyl-4-hydrazinonicotinate acetone hydrazone) and SFB (succinimidyl-4-formyl benzoate). Therapeutic agents can be cross-linked through their amino group to a carboxyl group of the collagen-binding polypeptide segment by EDC (1-ethyl-3-[3-dimethylaminopropyl]carbodiimide hydrochloride) or vice versa. These cross-linking products are available from Pierce (piercenet.com, Thermo Fisher Scientific Inc., Rockford, Ill.). Protocols and reaction conditions are also available in the product literature from Pierce (piercenet.com).

In another embodiment of the pharmaceutical agents comprising (a) a collagen-binding polypeptide segment; linked to (b) a polypeptide therapeutic agent or a PTH/PTHrP receptor agonist or antagonist polypeptide segment, segment (a) and segment (b) are separate polypeptides, and the two polypeptides are linked by chemical cross-linking. The two polypeptides can be cross-linked through amino groups by reagents including DSG (disuccinimidyl glutarate) or glutaraldehyde. They can also be cross-linked through amino groups by derivatizing one polypeptide with SANH (succinimidyl-4-hydrazinonicotinate acetone hydrazone) and the other with SFB (succinimidyl-4-formyl benzoate), and then mixing the two derivatized polypeptides to cross-link. The two polypeptides can be cross-linked between an amino group of one polypeptide and a carboxyl of the other by reaction with EDC (1-ethyl-3-[3-dimethylaminopropyl]carbodiimide hydrochloride). The polypeptides can also be cross-linked (e.g., covalently coupled) by any other suitable method known to a person of ordinary skill in the art. These cross-linking reagents are available from Pierce (piercenet.com, Thermo Fisher Scientific Inc., Rockford, Ill.). Protocols and reaction conditions are also available in the product literature from Pierce (piercenet.com). These and other applicable cross-linking methods are described in U.S. published patent applications 2006/0258569 and 2007/0224119.

Also provided herein are methods of treating hyperparathyroidism by administering PTH-CBD to a subject in need of treatment for hyperparathyroidism. In one embodiment the PTH administered to the subject may be a PTH from a different species. As shown in the Examples a single administration of CBD-PTH to ovarectomized aged rats was able to reduce the amount of endogenous PTH produced by the animal. Thus, administration of PTH-CBD to individuals suffering from hyperparathyroidism may experience a decrease in symptoms associated with hyperparathyroidism and have decreased levels of PTH after administration of PTH-CBD.

The effects of PTH agonists and antagonists on hair growth have been studied for over almost 15 years. PTH has a common receptor with PTH-related peptide (PTHrP), which is normally produced by dermal fibroblasts. PTHrP affects keratinocyte proliferation/differentiation and modulates the hair cycle. Most of the testing on hair growth effects has been performed with PTH antagonists, as indications from initial testing were that these were the most effective agents. Both injected and topical formulations have been tested in animal models of chemotherapy-induced alopecia and in the SKH-1 hairless mouse. Part of the effect of PTH antagonists on hair growth is to transition the hair follicles into a dystrophic catagen stage, which protects them from chemotherapeutic damage. However, clinical trials of topical PTH antagonists for chemotherapy-induced alopecia by IGI Pharmaceuticals were discontinued in phase 2 because of limited efficacy. Thus new compositions for treating alopecia are needed.

The problems of delivery and retention of PTH to the skin can be overcome by using collagen-targeted PTH analogs. To accomplish this, we synthesized several fusion proteins of different PTH agonists and antagonists linked to a collagen binding domain derived from the ColH1 collagenase of *Clostridium histolyticum*. In the studies described in the Examples, we found that the agonist compound PTH-CBD promotes transition of hair follicles to the anagen phase and has potent effects on hair growth. The antagonist compound PTH(7-33)-CBD had little effect on hair growth in chemotherapy models and had a deleterious effect on hair regrowth after depilation. Compounds such as PTH-CBD, which promote anagen phase transition of hair follicles, have been sought after due to their potential to treat a large variety of disorders of hair loss. PTH-CBD appears to have a similar mechanism of action to cyclosporine, which also promotes transition of hair follicles to anagen phase, although the mechanism is less likely to be the result of direct effects on WNT signaling. While clinical use of cyclosporine for this purpose is limited by systemic toxicity, PTH-CBD has not shown toxic effects, even with systemic administration.

Thus in another aspect, methods of increasing hair growth are provided herein. The methods include administering a CBD linked to a PTH/PTHrP receptor agonist to a subject in need of treatment to induce hair growth or stop hair loss. The method is applicable to individuals with alopecia, including chemotherapy induced alopecia, but also alopecia areata, alopecia caused by male pattern baldness, polycystic ovarian syndrome or other hair loss. The compositions may be administered locally or topically to treat hair loss.

In another aspect, methods of slowing hair growth or regrowth after a hair removal procedure by administering a CBD linked to a PTH/PTHrP receptor antagonist to a subject are provided. In one embodiment, the PTH antagonist composition is applied locally, topically. The PTH antagonist may be applied after a hair removal procedure to prevent or slow hair regrowth. As described in the Examples, we have demonstrated that hair regrowth is slowed after waxing in animals treated with CBD-PTH antagonist as compared to control animals treated with PTH-CBD or vehicle alone. The compositions may be administered locally or topically to block hair growth.

The compositions described herein may be administered by any means known to those skilled in the art, including, but not limited to, oral, topical, intranasal, intraperitoneal, parenteral, intravenous, intramuscular, intradermal or subcutaneous. Thus the compositions may be formulated as an ingestable, injectable, topical or suppository formulation. The composition may be formulated for administration by injection to result in systemic administration or local administration. The compositions may also be delivered with in a liposomal or time-release vehicle. The compositions may also be delivered in a site-directed delivery vehicle, such as but not limited to, a targeted liposome or an absorbable collagen sponge carrier or other implant.

The inventors have found that when administering compositions including a CBD subcutaneously it binds locally at the site of injection if the composition is dissolved in neutral pH buffer. But if the composition is dissolved in a low pH buffer, for example a buffer having pH 5.0 or pH 4.5 or below, the collagen-binding domain does not bind collagen, and the composition has time to disperse systemically before it binds collagen elsewhere in the body at neutral pH. Thus systemic administration of the compositions involves administering the composition dissolved in buffer or aqueous solution at a pH lower than about 5.0 or at pH 4.5 or below. In another embodiment, systemic administration of the compositions involves administering the fusion proteins dissolved in aqueous solution at pH lower than about 6.0. Alternatively, if the skin condition is localized, the compositions described herein may be administered in a buffer with a pH of 6.0, 6.5, 7.0, 7.5 or above in order to allow for localized delivery of the compositions to the affected area of the skin.

Pharmaceutical compositions for topical administration may also be formulated using methods and compositions such as those available to those skilled in the art. For example, gels, creams or liposome preparations may be suitable for topical delivery. These delivery vehicles may be formulated to mediate delivery to the lower layers of the skin or to allow for extended release of the pharmaceutical at the site of application.

The compositions can be administered as a single dose or as divided doses. For example, the composition may be administered two or more times separated by 4 hours, 6 hours, 8 hours, 12 hours, a day, two days, three days, four days, one week, two weeks, or by three or more weeks. Optionally, such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. The composition is expected to be more effective than a comparable or control composition comprising the therapeutic agent or a PTH/PTHrP receptor agonist that is not linked to a collagen-binding protein. In one embodiment, a smaller amount of the composition may be used or the composition may be administered less frequently than a comparable composition comprising the therapeutic agent or a PTH/PTHrP receptor agonist which is not linked to a collagen-binding protein.

The dosage amounts and frequencies of administration provided herein are encompassed by the terms therapeutically effective and prophylactically effective. The individual doses of pharmaceutical agents comprising a collagen-binding polypeptide segment linked to a therapeutic agent may be approximately the same on a molar basis as doses used for the therapeutic agent alone. It is expected that the pharmaceutical agents comprising a collagen-binding polypeptide segment linked to a therapeutic agent may be administered less frequently, because linking the agent to the collagen-binding polypeptide segment gives it much more prolonged activity in vivo.

Administration of the compositions to a subject in accordance with the invention appears to exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the compositions being administered, the disease to be treated or inhibited, the condition of the subject, and other relevant medical factors that may modify the activity of the agent or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions of the invention and of the therapeutic agent administered alone, such as by means of an appropriate conventional pharmacological or prophylactic protocol.

The maximal dosage for a subject is the highest dosage that does not cause undesirable or intolerable side effects. The number of variables in regard to an individual prophylactic or treatment regimen is large, and a considerable range of doses is expected. The route of administration will also impact the dosage requirements. It is anticipated that dosages of the compositions will reduce symptoms of the condition being treated by at least 10%, 20%, 30%, 40%, 50%, 60%, 70%, 80%, 90% or 100% compared to pre-treatment symptoms or symptoms is left untreated. It is specifically contemplated that pharmaceutical preparations and compositions may palliate or alleviate symptoms of the disease without providing a cure, or, in some embodiments, may be used to cure the disease or disorder.

Suitable effective dosage amounts for administering the compositions may be determined by those of skill in the art, but typically range from about 1 microgram to about 10,000 micrograms per kilogram of body weight weekly, although they are typically about 1,000 micrograms or less per kilogram of body weight weekly. In some embodiments, the effective dosage amount ranges from about 10 to about 10,000 micrograms per kilogram of body weight weekly. In another embodiment, the effective dosage amount ranges from about 50 to about 5,000 micrograms per kilogram of body weight weekly. In another embodiment, the effective dosage amount ranges from about 75 to about 1,000 micrograms per kilogram of body weight weekly. The effective dosage amounts described herein refer to total amounts administered, that is, if more than one compound is administered, the effective dosage amounts correspond to the total amount administered.

The effectiveness of the compositions described herein may be enhanced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to a control treated with the therapeutic agent alone. It will be appreciated that the effectiveness of the treatment in any given case will be enhanced variably in accordance with the specific compositions used, the type of disease being treated, the condition of the subject, the specific formulations of the compounds and other relevant medical factors that may modify the activity of the compositions or the responses of the subject as is appreciated by those of skill in the art.

The following examples are meant only to be illustrative and are not meant as limitations on the scope of the

EXAMPLES

Example 1: CBD Targets Partially Untwisted or Undertwisted Regions of Collagen

*Clostridium histolyticum* collagenase causes extensive degradation of collagen in the connective tissue resulting in gas gangrene. The C-terminal collagen-binding domain (CBD) of these enzymes is the minimal segment required to bind to the collagen fibril. CBD binds unidirectionally to the partially untwisted C-terminus of triple helical collagen. Whether CBD could also target under-twisted regions even in the middle of the collagen triple helix was examined. Partially untwisted collageneous peptides were synthesized by introducing a Gly→Ala substitutions into the collagen ([(POG)$_x$POA(POG)$_y$]$_3$ where x+y=9 and x>3). $^1$H-$^{15}$N heteronuclear single quantum coherence nuclear magnetic resonance (HSQC NMR) titration studies with $^{15}$N-labeled CBD demonstrated that the untwisted mini-collagen binds to a 10 Å wide 25 Å long cleft. Six untwisted collagenous peptides each labeled with a nitroxide radical were then titrated with $^{15}$N-labeled CBD. The paramagnetic nuclear spin relaxation effects showed that CBD binds close to either the Gly→Ala substitution site or to the C-terminus of each mini-collagen. Small angle X-ray scattering (SAXS) measurements revealed that CBD prefers to bind the Gly→Ala site rather than the C-terminus. The HSQC NMR spectra of $^{15}$N-labeled mini-collagen and untwisted mini-collagen were unaffected by the titration of unlabeled CBD. The results imply that CBD binds to the partially unwound region of the mini-collagen but does not actively unwind the triple helix.

Materials and Methods $^{15}$N-labeled protein production: The s3b (Gly893-Lys1008) peptide derived from *Clostridium histolyticum* class I collagenase (ColG) was expressed as a glutathione S-transferase (GST)-fusion protein. The GST-tag was cleaved off by thrombin, and CBD was purified as described previously. Matsushita, et al., (2001) *J Biol Chem* 276, 8761-8770. Uniform $^{15}$N isotope labeling was achieved using Tanaka minimal medium containing 40 mM $^{15}$NH$_4$Cl. The labeling efficiency was estimated to be 99.6% by matrix-assisted laser desorption/ionization-time of flight mass spectrometry (MALDI-TOF-MS).

Peptides: (POG)$_{10}$ (SEQ ID NO: 35) was purchased from Peptide Institute, Inc. (Osaka, Japan). Other peptides were constructed by a standard N-(9-fluorenyl) methoxycarbonyl (Fmoc)-based strategy on Rink-amide resins (Novabiochem, Darmstadt, Germany). N-terminal spin-labeling was performed on the resin by the treatment with 5 equivalents of 3-carboxy-PROXYL (Aldrich), 1-hydroxybenzotriazole, diisopropylcarbodiimide in N,N-dimethylformamide at room temperature for 2 hours. Peptide cleavage and de-protection steps were performed by a treatment with a standard trifluoroacetic acid (TFA) scavenger cocktail (TFA: m-cresol:thioanisole:water:triisopropylsilane=82.5:5:5:5: 2.5, v/v). The spin-labeling at Cys residues was performed using 3-(2-iodoacetamido)-PROXYL (IPSL, Sigma-Aldrich). Briefly, 10 molar excess of IPSL dissolved in ethanol was added to the same volume of 10 mg/ml peptide in 0.1 M Tris-HCl (pH 8.8), 5 mM ethylenediaminetetraacetic acid. After reacting at room temperature for 1 hr, the reaction was quenched by adding excess dithiothreitol. All peptides were purified by reverse-phase HPLC using a Cosmosil 5C$_{18}$ AR-II column (Nacalai Tesque, Kyoto, Japan) and characterized by MALDI-TOF-MS. All the measured masses agreed with the expected values. The chemical structures of synthesized peptides are shown in FIG. 2.

Figure 3B:
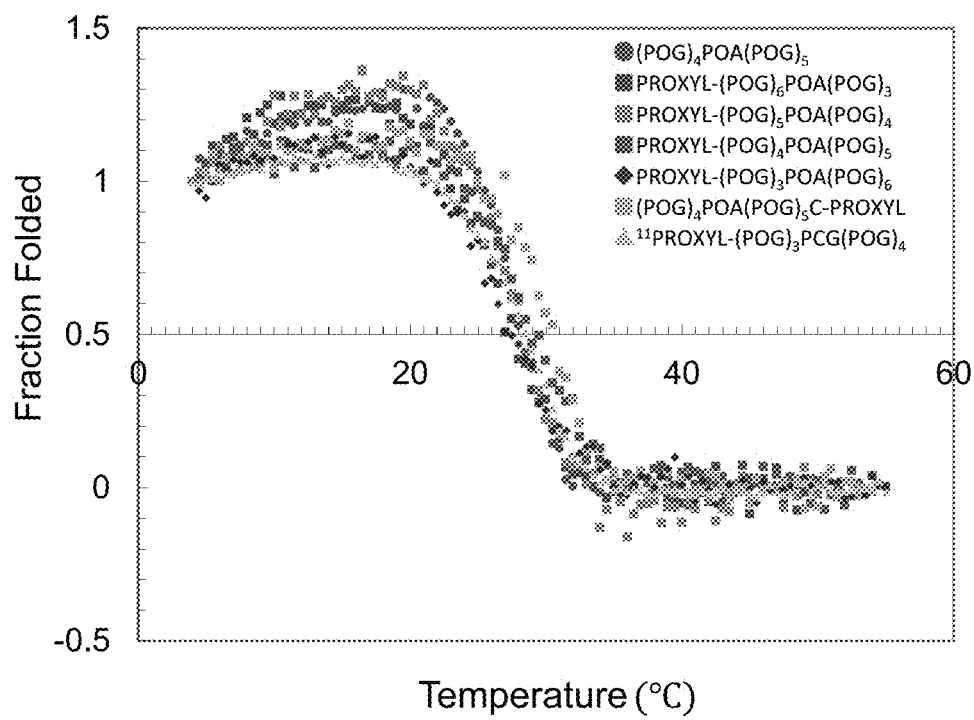
FIG. 3B is a graph showing the thermal denaturation profile of the various collagenous peptides. The temperature was increased at the rate of 0.3° C./min.

Circular dichroism spectroscopy: The triple helical conformation and the stability of the collagenous peptides were verified using CD spectroscopy (See FIGS. 3 and 4). CD spectra were recorded with a J-820 CD spectropolarimeter (JASCO Co., Hachioji, Japan) equipped with a Peltier thermo controller, using a 0.5-mm quartz cuvette and connected to a data station for signal averaging. All peptide samples were dissolved in water (1 mg/ml), and stored at 4° C. for 24 h. The spectra are reported in terms of ellipticity units per mole of peptide residues $[\theta]_{mrw}$. Thermostability of the triple helix was monitored by the $[\theta]_{225}$ values of each peptide with increasing temperature at the rate of 0.3° C./min.

NMR spectroscopy: NMR experiments were performed on a Bruker 700 MHz spectrometer equipped with Cryoprobe™. All the NMR titration experiments were carried out at 16±0.5° C. The working temperature is lower than the melting temperatures ($T_M$) of all the paramagnetic spin-labeled collagenous peptides (Table 1) used. The concentration of the protein was 0.1 mM in 50 mM Tris-HCl (pH 7.5) containing 100 mM NaCl and 20 mM CaCl$_2$. The dilution effect on the course of titration was minimized by the titration of a highly concentrated (4 mM) peptide stock. Aliquots of collagenous peptide were added to the protein and equilibrated for 5 min before acquiring $^1$H-$^{15}$N HSQC spectra. The pH of the NMR samples monitored during the titration exhibited no significant shift in the pH (within ±0.2 units).

TABLE 1

Melting temperatures ($T_m$) of various mini-collagen peptides that were used in NMR titration and the experiments described herein.

| Peptides | Tm (° C.) | SEQ ID NO: |
|---|---|---|
| (POG)$_4$POA(POG)$_5$ | 29 | 38 |
| PROXYL-(POG)$_4$POA(POG)$_5$ | 29 | 38 |
| PROXYL-(POG)$_3$POA(POG)$_6$ | 28 | 39 |
| PROXYL-(POG)$_5$POA(POG)$_4$ | 28 | 37 |
| PROXYL-(POG)$_6$POA(POG)$_3$ | 27 | 36 |
| (POG)$_4$POA(POG)$_5$C-PROXYL | 30 | 41 |
| $^{11}$PROXYL-(POG)$_3$PCG(POG)$_4$ | 28 | 40 |

Dynamic light scattering experiments: The dynamic light scattering (DLS) data were collected using DynaPro-E equipped with a temperature controlled microsampler on the samples of CBD, collagenous peptides and CBD:mini-collagen complexes in 10 mM Tris-HCl (pH 7.5) containing 100 mM sodium chloride and 20 mM CaCl$_2$. The protein samples were spun at 10,000 rpm for 10 min and were filtered through 0.02 µm Whatman syringe directly into a 50-µL quartz cuvette. For each experiment, 20 measurements were made. The mean hydrodynamic radius ($R_H$), standard deviation, polydispersity, and percent of peak area were analyzed using Dynamics V6 (Protein Solutions). The hydrodynamic radius and molecular weight estimations were calculated from time dependent fluctuations induced by Brownian motion as described. Proteau, et al. (2010) *Curr Protoc Protein Sci* Chapter 17, Unit 17 10.

Small angle X-ray solution scattering experiments: The small angle X-ray solution scattering (SAXS) data were collected on solutions of CBD, collagenous peptides and CBD-mini-collagen complexes in 10 mM Tris-HCl (pH 7.5), 100 mM NaCl and 20 mM $CaCl_2$ at SAXS/WAXS setup located at the 5-ID-D beamline of the DND-CAT synchrotron research center, Advanced Photon Source, Argonne National Laboratory (Argonne, Ill.). The main advantage of X-ray scattering is that it can be carried out in solution in near physiological conditions. Petoukhov et al., (2007) *Curr Opin Struct Biol* 17, 562-571. 1.2398 Å (10 keV) radiation was selected from the APS Undulator A insertion device using a Si-111 monochromator, with 1:1 horizontal focusing and higher harmonic rejection from a Rh coated mirror, and beam defining slits set at 0.3 mm vertical by 0.25 mm horizontal. A 1.6 mm diameter capillary flow-cell with a flow rate of 4 μl/sec was used to collect four frames with 10 second exposure time. The SAXS detector used was a Mar165 scintillator fiber-optic coupled CCD detector and covered the momentum transfer range $0.005 < q < 0.198$ $Å^{-1}$, where $q = 4\pi \sin \theta/\lambda$ ($2\theta$ is the scattering angle). The WAXS detector was a custom Roper scintillator fiber-optic coupled CCD detector and covered $0.191 < q < 1.8$ $Å^{-1}$ S. Weigand, et al. (2009) *Advances in X-ray Analysis* 52, 58-68.

Figure 4A:
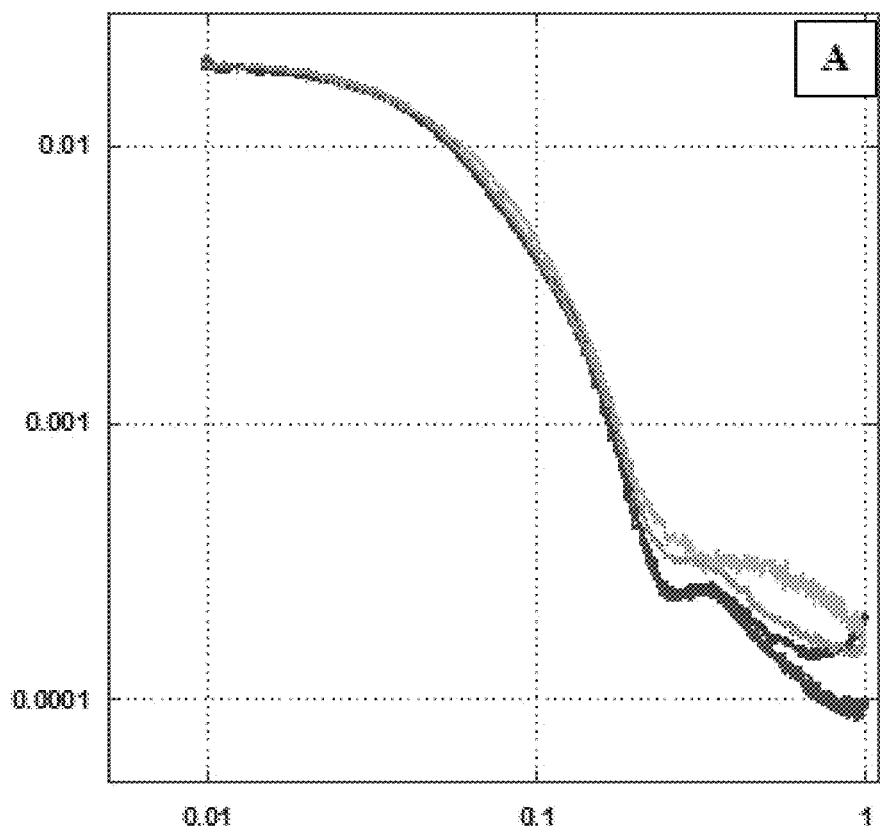
FIG. 4A is a graph showing the scattering profile with the intensity I(Q) plotted against the scattering vector Q.
Figure 4B:
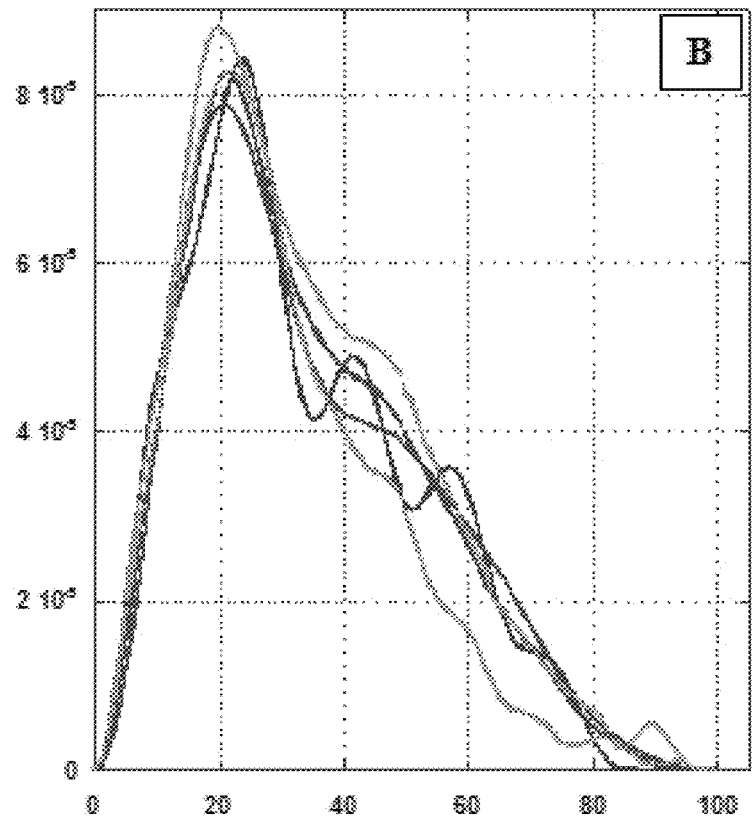
FIG. 4B is a graph showing the pair-distance distribution function P(r) in the real space obtained using GNOM for [PROXYL-(POG)$_3$POA(POG)$_6$]$_3$:CBD complex (Red), [PROXYL-(POG)$_4$POA(POG)$_5$]$_3$:CBD complex (Blue), [PROXYL-(POG)$_5$POA(POG)$_4$]$_3$:CBD complex (Green), [PROXYL-(POG)$_6$POA(POG)$_3$]$_3$:CBD complex (Orange) and [11PROXYL-(POG)$_3$PCG(POG)$_4$]$_3$:CBD complex (Cyan).

All scattering data were acquired at sample temperature of 10° C. The four scattering patterns from each detector were averaged and merged with the rejection of outlying scans. For further analysis the program IGOR Pro 5.5 A (WaveMetrics) was used. The scattering profiles of the protein, peptide and their complexes were obtained after subtracting the buffer profiles. The reduced scattering data were plotted as scattering intensity I(Q) vs. Q (FIG. 4A). The radius of gyration, $R_g$, was obtained from the Guinier approximation by linear least squares fitting in the $QR_g < 1$ region, where the forward scattering intensity I(0) is proportional to the molecular weight of the protein complex. An indirect Fourier transformation of I(Q) data using GNOM provided the particle distribution function P(r) in the real space (FIG. 4B). Svergun, D. (1992) *J Appl Crystallogr* 25, 495-503. Where P(r) intersects with x-axis represents the maximum diameter $D_{max}$ averaged in all orientations. The molecular envelopes were constructed for all the samples based on the SAXS data after ab initio calculation with the program GASBOR. Svergun, et al. (2001) *Biophys J* 80, 2946-2953. Simulated annealing minimization of randomly distributed dummy atoms converged to the protein structure after being tested for the best fit to the I(Q) scattering data. No symmetry restraints were applied to any of the shape reconstructions. For each of the complexes, ten ab initio models were calculated with GASBOR and averaged using DAMAVER. Svergun, D. (2003) *J Appl Crystallog* 36. The atomic models represented as a compact interconnected configuration of beads with diameter $D_{max}$ were adjusted to fit the experimental data $I_{exp}(s)$ to minimize error. Atomic models were docked into ab initio envelopes with the program SUBCOMB. Kozin, M. B., and Svergun, D. (2000) *J Appl Crystallogr* 33, 775-777.

Docking model: The CBD-collagenous peptide complex is generated from Protein Data Bank entries of ColG s3b (1NQD) and partially untwisted collagenous peptide 1CAG (Ala mutation in $15^{th}$ position). Other untwisted mini collagen molecules were generated by modifying 1CAG using fragments derived from $[(POG)_{10}]_3$ structure (1K6F). To obtain the complex, the soft docking algorithm BiGGER was used. Palma, et al. (2000) *Proteins* 39, 372-384. Solutions were filtered using NMR titration data and the highest scoring model that satisfied NMR and SAXS results was chosen. The manual adjustments were aided by the use of MIFit. McRee. (1999) *J Struct Biol* 125, 156-165.

Figure 5A:
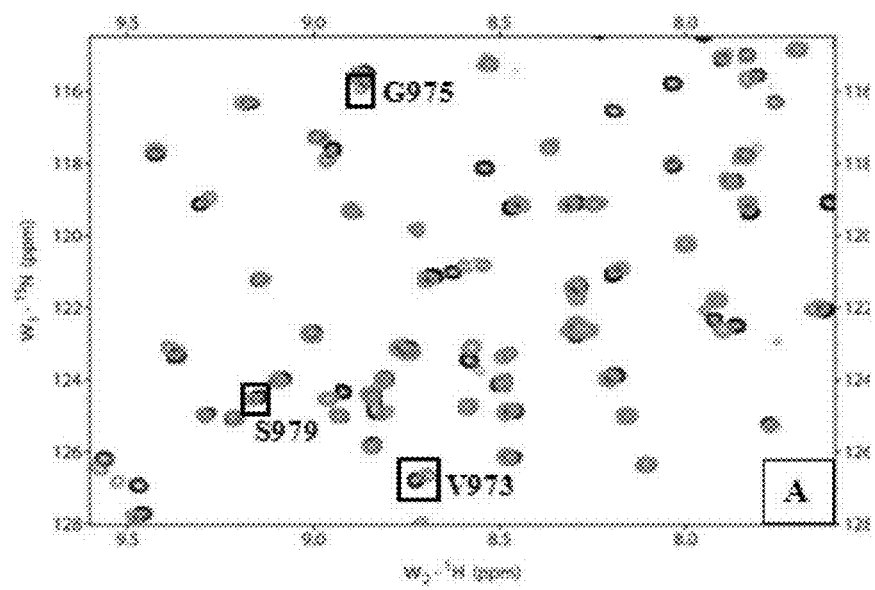
FIG. 5A, FIG. 5B and FIG. 5C are a set of plots showing HSQC NMR data obtained using the collagen binding domain (CBD)—collagenous peptide interactions.
Figure 5B:
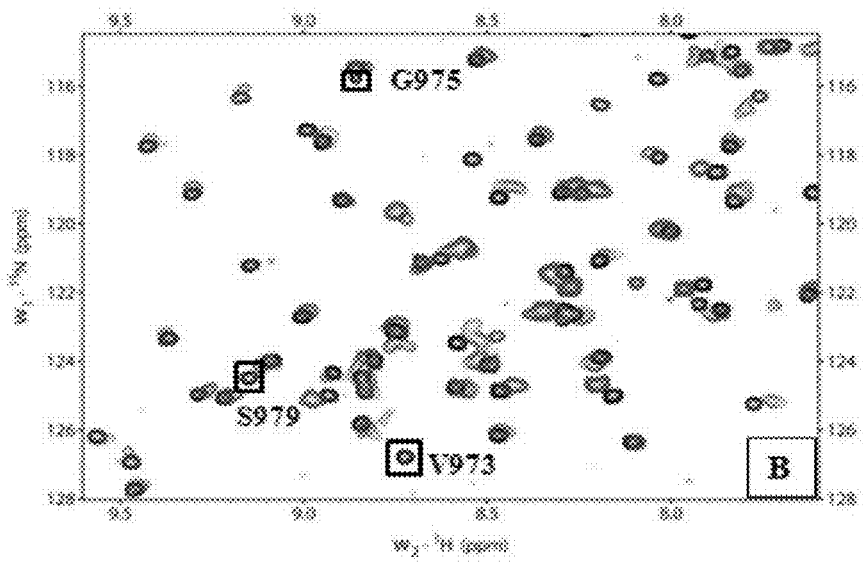
Figure 5C:
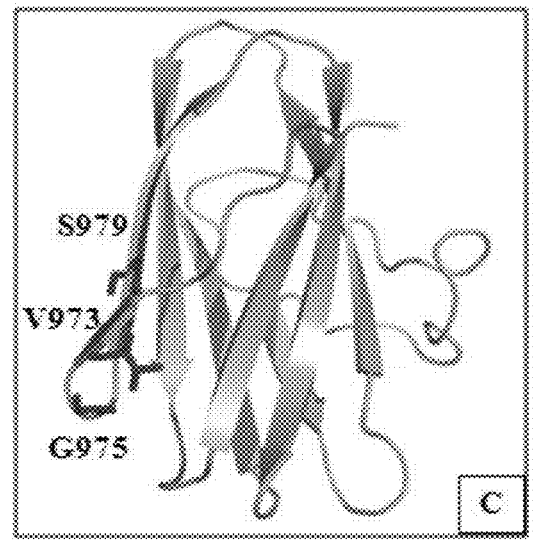

Results and Discussion $^1H$-$^{15}N$ HSQC NMR titration-CBD targeting the under-twisted sites in collagen: The untwisted collagenous peptide $[(POG)_6POA(POG)_3]_3$ (SEQ ID NO: 36) that has Ala in the $21^{st}$ position from the N-terminus was synthesized. This peptide was further modified to accommodate a paramagnetic spin label at the N-terminus. $^1H$-$^{15}N$ HSQC NMR titrations were performed with [PROXYL-$(POG)_6POA(POG)_3]_3$ (SEQ ID NO: 36) and $^{15}N$-labeled CBD at ratios ranging from 0.02:1 to 1.5:1. As demonstrated earlier, a total of eleven residues on the collagen binding interface (S928, W956, G971, K995, Y996, L924, T957, Q972, D974, L991 and V993) either disappeared from the HSQC spectrum or exhibited significant chemical shift perturbation from their original position on the course of titration. Philominathan, et al. (2009) *J Biol Chem* 284, 10868-10876. The PROXYL group on the N-terminus of the collagenous peptides can cause a distance-dependent line broadening of the NMR signals of CBD during the course of titration. In addition to the eleven residues, three more residues, V973, G975 and S979 exhibited appreciable line broadening and these residues eventually disappeared from the $^1H$-$^{15}N$ HSQC spectrum of CBD (FIGS. 5A and 5B). When the [PROXYL-$(POG)_6POA(POG)_3]_3$ (SEQ ID NO: 36):CBD complex was reduced with ascorbic acid those three residues reappeared in the $^1H$-$^{15}N$ HSQC spectrum. The disappearance of these three residues was consistent with the titration of [PROXYL-$G(POG)_7]_3$ (SEQ ID NO: 42) (C-terminus is at $22^{nd}$ position from the N-terminal PROXYL) in our earlier publication. The comparison of the two titration results demonstrates that CBD is targeting the Gly→Ala substituted site. If CBD had only bound to the C-terminus of [PROXYL-$(POG)_6POA(POG)_3]_3$ (SEQ ID NO: 36) (C-terminus is at $30^{th}$ position from the N-terminal PROXYL), we would expect to observe the disappearance of only one residue (V973) at the most, as in the published titration of [PROXYL-$G(POG)_7(PRG)]_3$ (SEQ ID NO: 43). The disappearance of the residues (V973, G975 and S979) located at distal side from the $Ca^{2+}$ binding site (FIG. 5C) confirmed that CBD binds unidirectionally to untwisted collagen as well. The collagen binding surface in CBD is a 10-Å-wide and 25-Å-long cleft. The width of the binding cleft in CBD matches the diameter of the triple helix and its length could accommodate $[(POG)_3]_3$ (SEQ ID NO: 44). NMR results imply that CBD is binding to the under-twisted $[(POG)_2POA]_3$ (SEQ ID NO: 45) region of the collagen.

As paramagnetic relaxation enhancement is a distance dependent phenomenon, Gly→Ala substitution made at closer to the N-terminal PROXYL group should result in the disappearance of more residues on CBD. PROXYL containing collagenous peptides, [PROXYL-$(POG)_5POA(POG)_5POA(POG)_4]_3$ (SEQ ID NO: 37) (Ala at $18^{th}$ position from the N-terminal PROXYL), [PROXYL-$(POG)_4POA(POG)_5]_3$ (SEQ ID NO: 38) (Ala at the $15^{th}$ position from the PROXYL) and [PROXYL-$(POG)_3POA(POG)_6]_3$ (SEQ ID NO: 39) (Ala at the $12^{th}$ position from the PROXYL) were synthesized. Just as in the previous titrations, the line broadening effects on the residues of CBD were analyzed from the changes in the $^1H$-$^{15}N$ HSQC spectrum. The shorter the distance between Gly→Ala substitution site and the N-terminal PROXYL, more residues in CBD disappeared (FIG. 6 and Table 2). The magnitude of intensity drop for four amide resonances (Q972, G975, S979 and L924) of four different mini-collagen molecules was also the function of the distance (FIG. 7). The NMR results are consistent with CBD binding to the [(POG)$_2$POA]$_3$ (SEQ ID NO: 45) region in each of the four under-twisted mini-collagen. The binding constants obtained from all the NMR titrations were <100 μM indicating a moderate binding affinity between CBD and under-twisted mini-collagen.

the HSQC spectrum of CBD were monitored. When the mini-collagen was bound to the cleft, a total of eleven residues on the collagen binding interface either line broadened or showed significant chemical shift perturbation as described earlier. Philominathan, et al. (2009) *J Biol Chem* 284, 10868-10876. Four additional residues S906, R929, S997 and G998 disappeared from the HSQC spectrum due to PROXYL (FIGS. 6 A, B and D). These peaks reappeared upon addition of ascorbic acid. This phenomenon is identical to our previous titration of [GPRG(POG)$_7$C-PROXYL]$_3$ (SEQ ID NO: 46) when CBD bound the C-terminus. If CBD

TABLE 2

Residues that disappear due to the presence of PROXYL either at the N-terminus, C- terminus or in the middle of the collagenous peptide sequence.

| No. | Peptides | Alanine position | Residues disappeared due to PROXYL |
|---|---|---|---|
|  | Blank |  |  |
| 1 | [(POG)10]3 (SEQ ID NO: 35) |  |  |
|  | PROXYL at N-terminus |  |  |
| 2 | [PROXYL-(POG)6POA(POG)3]3 (SEQ ID NO: 36) | 21 | V973, G975, S979 |
| 3 | [PROXYL-(POG)5POA(POG)4]3 (SEQ ID NO: 37) | 18 | Q972, V973, G975, S979 |
| 4 | [PROXYL-(POG)4POA(POG)5]3 (SEQ ID NO: 38) | 15 | L946, Q972, V973, G975, S979 L946, G953, Q972, V973, D974, |
| 5 | [PROXYL-(POG)3POA(POG)6]3 (SEQ ID NO: 39) | 12 | G975, N976, V978, S979 |
|  | PROXYL at C-terminus |  |  |
| 6 | [(POG)4POA(POG)5-PROXYL]3 (SEQ ID NO: 41) | 15 | S906, R929, S997, G998 |
|  | PROXYL in the middle |  |  |
| 7 | [11PROXYL-(POG)3PCG(POG)4]3 (SEQ ID NO: 40) |  | V973, G975, S979 and S906, R929, S997, G998 |

The helical conformation in both the [(POG)$_2$POA]$_3$ (SEQ ID NO: 45) and the C-terminal [(POG)$_3$]$_3$ (SEQ ID NO: 44) are similarly under-wound. The degree of rotation about the screw axis symmetry that describes the internal triple helical twist is defined as the helical twist value κ. The κ-value oscillates around an average value of −103° for [(POG)$_{10}$]$_3$ (SEQ ID NO: 35). Bella (2010) *J Struct Biol* 170, 377-391. The C-terminus of a mini-collagen is under-twisted (κ value shifts from −103° to −110°) but the N-terminus is usually over-twisted. Collagen peptides with Gly→Ala substitution in the center of the peptide sequence still form triple helices, but with an abrupt under-twisting (κ value shifts from −103° to −115°) at the substitution site followed over-twisting to the norm. Because the [(POG)$_2$POA]$_3$ (SEQ ID NO: 45) region is somewhat more under-twisted than C-terminal [(POG)$_3$]$_3$ (SEQ ID NO: 44), the former could be preferentially targeted by CBD than the latter. However, CBD could still bind to the C-terminus.

CBD also targets the C-terminus of the under-twisted mini-collagen: To demonstrate that CBD binds to the C-terminal (POG)$_3$ (SEQ ID NO: 44) as well, a collagenous peptide [(POG)$_4$POA(POG)$_5$-PROXYL]$_3$ (SEQ ID NO: 38) was synthesized. [(POG)$_4$POA(POG)$_5$C-PROXYL]$_3$ (SEQ ID NO: 41) was titrated with $^{15}$N-labeled CBD at ratios 0.02:1 to 1.5:1 with increments of 0.02, and the changes in were to bind only to the partially unwound Ala site, we would have observed the disappearance of fewer residues. Thus in addition to targeting the (POG)$_2$POA (SEQ ID NO: 45) region of the collagenous peptide, CBD also binds to the C-terminal (POG)$_3$ (SEQ ID NO: 44). As described, the helical confirmation of both the (POG)$_2$POA (SEQ ID NO: 45) region and the C-terminal (POG)$_3$ (SEQ ID NO: 44) are similarly under-twisted compared to the norm. Bella. (2010) *J Struct Biol* 170, 377-391. Our current explanation for why CBD is targeting the under-twisted regions is that the partial unwinding positions main-chain carbonyl groups to favor hydrogen-bonding interactions with the hydroxyl group of Tyr994. Tyr994 mutation to Phe resulted in 12-fold reduction in binding to mini-collagen, and the mutation to Ala lost binding capability. Wilson, et al. (2003) *EMBO J* 22, 1743-1752.

To demonstrate CBD's ability to target both the (POG)$_2$POA (SEQ ID NO: 45) region and the C-terminal (POG)$_3$ (SEQ ID NO: 44) region, a collagenous peptide [11PROXYL-(POG)$_3$PCG(POG)$_4$]$_3$ (SEQ ID NO: 40) modified to accommodate PROXYL group in the middle (11$^{th}$ position) was synthesized. PROXYL group is covalently joined to the cysteine residue. Due to the presence of the bulky PROXYL group, this peptide is expected to be partially untwisted. The precise degree of under-twisting is not known for the peptide, but mini-collagen with GPX repeats exhibits a moderate under-twisting ($\kappa=-105°$). Bella. (2010) *J Struct Biol* 170, 377-391. The bulky PROXYL group will likely induce greater untwisting than $\kappa=-105°$. In addition to the eleven amide resonances either line-broaden or shifted, $^1$H-$^{15}$N HSQC NMR titrations revealed two distinct phenomena. At lower ratio (0.2:1) amide resonances corresponding to S906, R929, S997, and G998 disappeared from the HSQC spectrum of CBD (FIGS. 8E, F and H). Then at higher ratio (0.3:1), additional amide resonances corresponding to V973, G975 and S979 disappeared from the HSQC spectrum of CBD (FIGS. 8E, F and H). In order to cause the disappearance of four residues (S906, R929, S997 and G998), CBD must initially bind to the N-terminal (POG)$_3$ (SEQ ID NO: 44). The disappearance of resonances V973, G975 and S979 can be explained if CBD binds to the C-terminal (POG)$_3$ (SEQ ID NO: 44) of the mini-collagen. However the initial phenomenon signifies that CBD binds preferentially to the under-twisted midsection to C-terminus.

To demonstrate that PROXYL caused the line broadening and Ala or Cys residues did not, three more control peptides, titration results were nearly identical with those of [(POG)$_{10}$]$_3$ (SEQ ID NO: 35). Only the eleven amide resonances were either line broadened or shifted even at 1:1 (mini-collagen:CBD) ratio. These control peptides bound to the same cleft, and PROXYL caused the additional residues to line broaden.

To illustrate if CBD binds only to the partially untwisted site in the middle of the collagen peptide and/or to the C-terminus of mini-collagen, dynamic light scattering experiments (DLS) were performed. DLS experiments provided the stoichiometries of collagen:CBD complexes. The hydrodynamic radius of [(POG)$_4$POA(POG)$_5$-PROXYL]$_3$ (SEQ ID NO: 38):CBD and [11PROXYL-(POG)$_3$PCG (POG)$_4$]$_3$ (SEQ ID NO: 40):CBD was 3 nm and the apparent molecular weight of the complex was 42±1 kDa, which is similar to those observed for [(POG)$_{10}$]$_3$ (SEQ ID NO: 35):CBD complex (Table 3). Other complexes also exhibited similar values. Thus far, all the mini-collagen and CBD always formed 1:1 complex. CBD binds to either one of the available sites in mini-collagen but does not occupy both sites to form a 1:2 complex.

TABLE 3

Hydrodynamic radius (RH), apparent molecular weight (Mw), Radius of gyration (Rg) and Maximum particle diameter (Dmax) computed from Dynamic light scattering (DLS) and small angle X-ray scattering (SAXS) for various CBD:collagenous peptides complexes.

| No | Complexes | Dynamic Light Scattering (DLS) | | Small Angle X-ray Scattering (SAXS) | |
|---|---|---|---|---|---|
| | | Hydrodynamic Radius (RH) | Apparent Molecular Weight (Mw) | Radius of Gyration (Rg) | Max Diameter (Dmax) |
| 1 | CBD:[(POG)10]3 (SEQ ID NO: 35) | 3 | 43 | 22.62 ± 0.04 | 93 |
| 2 | CBD:[PROXYL-(POG)6POA(POG)3]3 (SEQ ID NO: 36) | 3 | 44 | 24.67 ± 0.09 | 87 |
| 3 | CBD:[PROXYL-(POG)5POA(POG)4]3 (SEQ ID NO: 37) | 3 | 42 | 21.08 ± 0.02 | 90 |
| 4 | CBD:[PROXYL-(POG)4POA(POG)5]3 (SEQ ID NO: 38) | 3 | 43 | 25.48 ± 0.08 | 92 |
| | CBD:[(POG)4POA(POG)5]3 (SEQ ID NO: 38) | 3 | 43 | 24.45 ± 0.14 | 85 |
| 5 | CBD:[PROXYL-(POG)3POA(POG)6]3 (SEQ ID NO: 39) | 3 | 42 | 21.97 ± 0.14 | 94 |
| 6 | CBD:[(POG)4POA(POG)5C-PROXYL]3 (SEQ ID NO: 41) | 3 | 44 | 24.09 ± 0.16 | 85 |
| | CBD:[(POG)4POA(POG)5]3 (SEQ ID NO: 38) | 3 | 42 | 24.67 ± 0.1 | 84 |
| 7 | CBD:[11PROXYL-(POG)3PCG(POG)4]3 (SEQ ID NO: 40) | 3 | 42 | | 96 |
| | CBD:[(POG)3PCG(POG)4]3 (SEQ ID NO: 40) | 3 | 43 | 23.59 ± 0.05 | 90 |

Figure 6A:
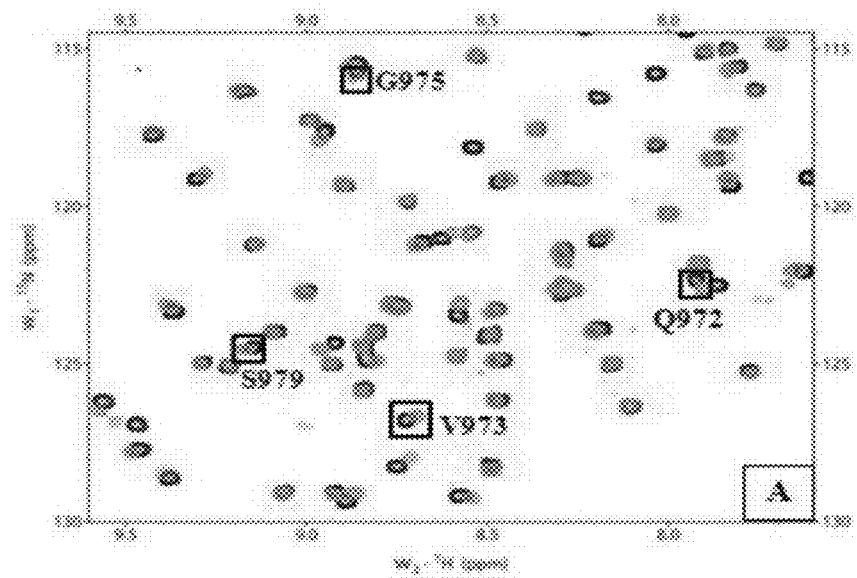
FIG. 6A through FIG. 6I are a set of plots showing HSQC NMR data obtained using the CBD—collagenous peptide interactions.
Figure 6B:
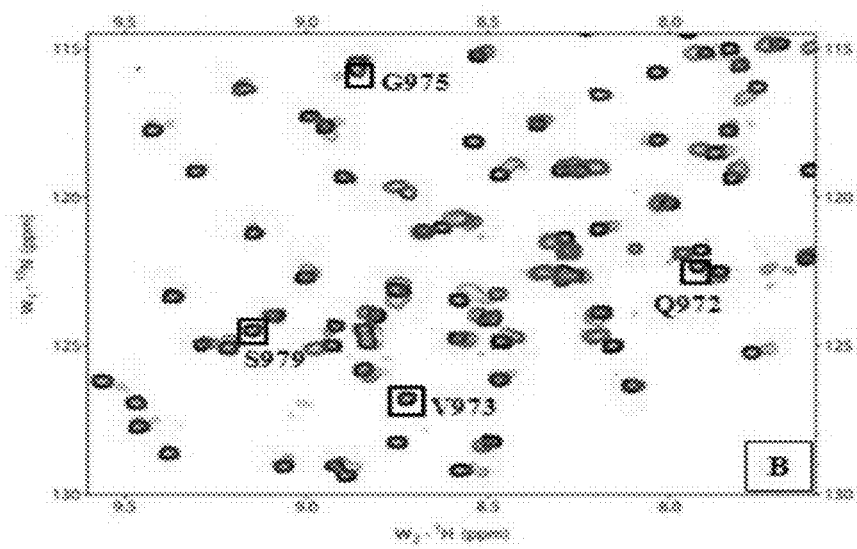
Figure 6C:
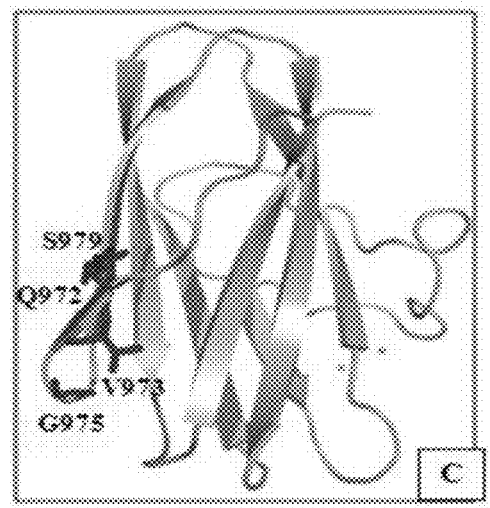
Figure 6D:
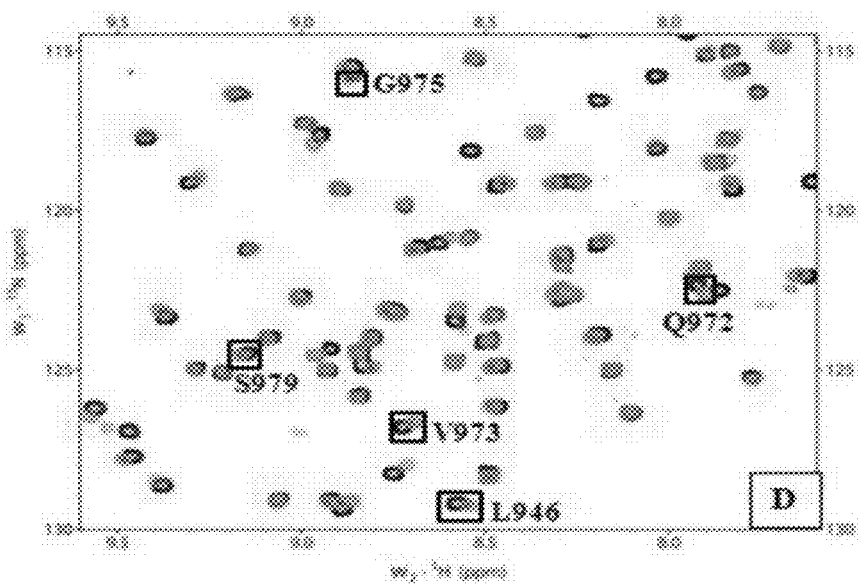
Figure 6E:
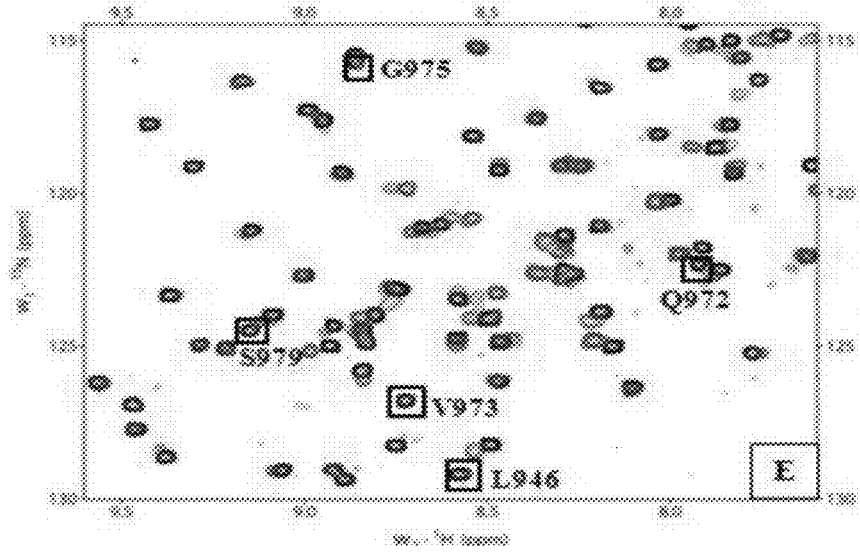
Figure 6F:
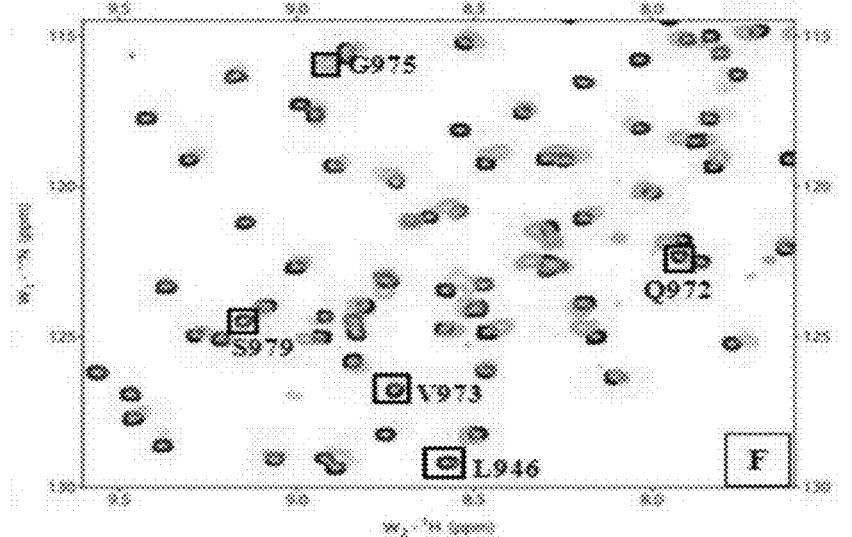
Figure 6G:
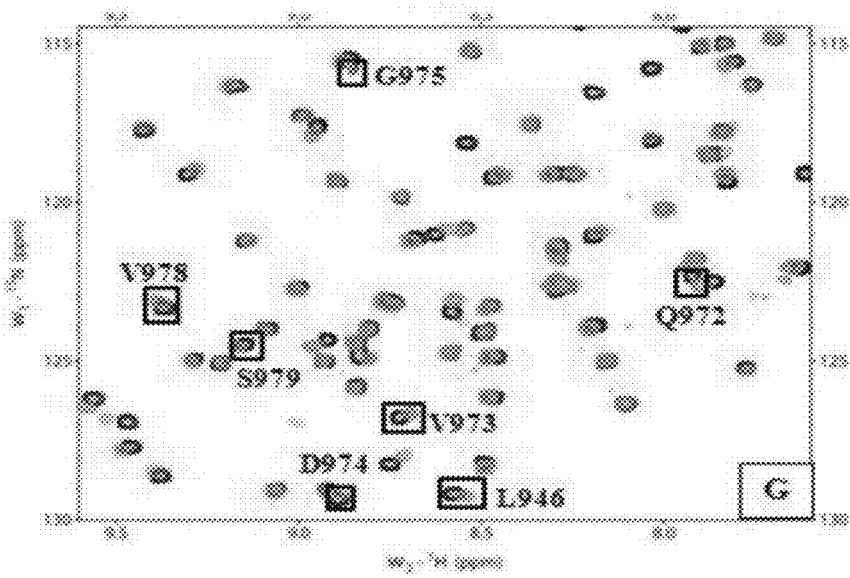
Figure 6H:
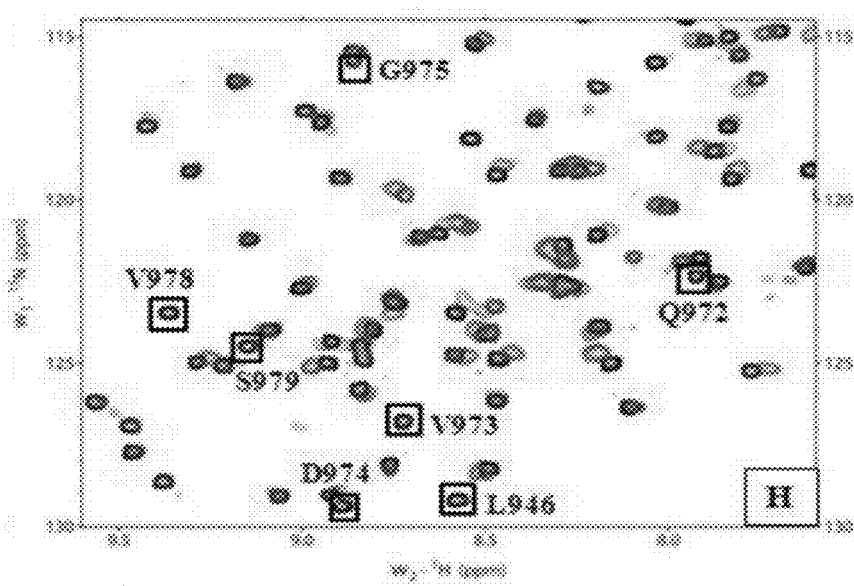
Figure 6I:
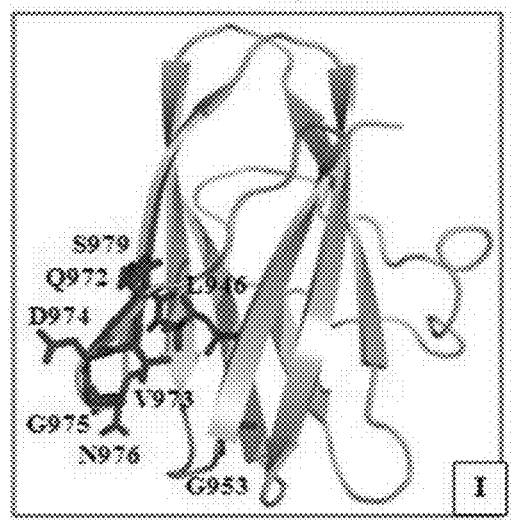
Figure 7A:
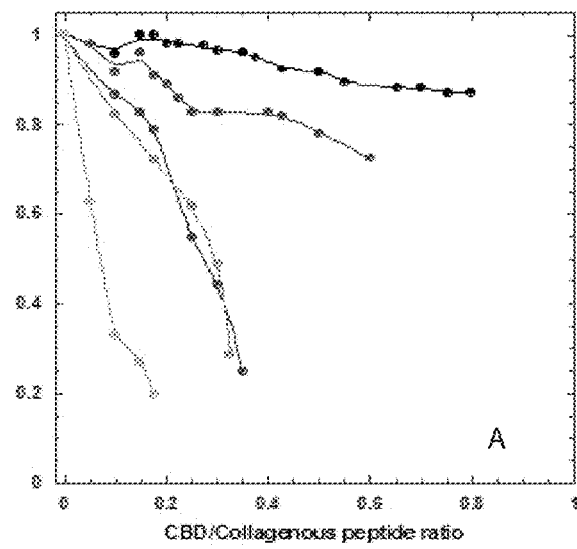
FIG. 7A through FIG. 7D are a set of graphs showing the intensity drop of Q972 (FIG. 7A), G975 (FIG. 7B), S979 (FIG. 7C) and L924 (FIG. 7D) on CBD as a function of increasing concentrations of mini-collagen i.e. [(POG)$_{10}$]$_3$ (black), [PROXYL-(POG)$_6$POA(POG)$_3$]$_3$(red), [PROXYL-(POG)$_5$POA(POG)$_4$]$_3$(blue), [PROXYL-(POG)$_4$POA (POG)$_5$]$_3$(green), and [PROXYL-(POG)$_3$POA(POG)$_6$]$_3$ (cyan).
Figure 7B:
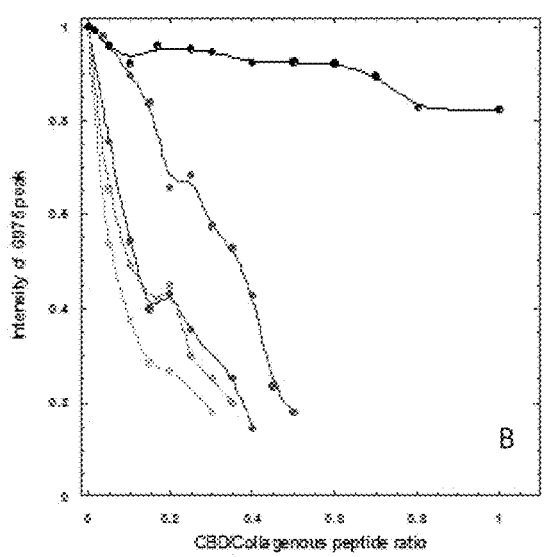
Figure 7C:
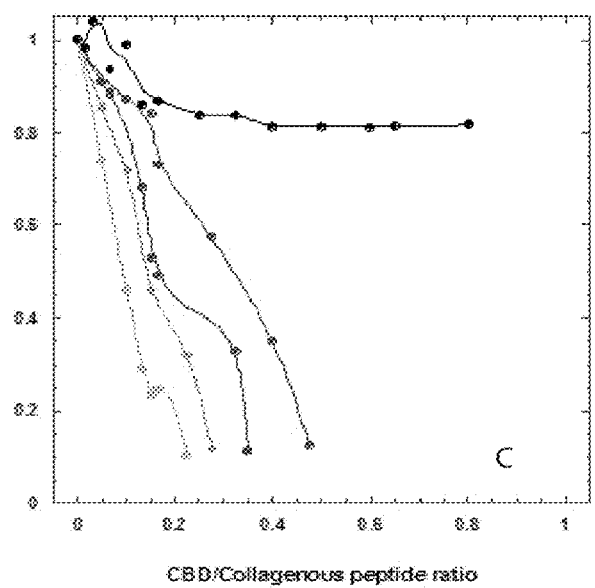
Figure 7D:
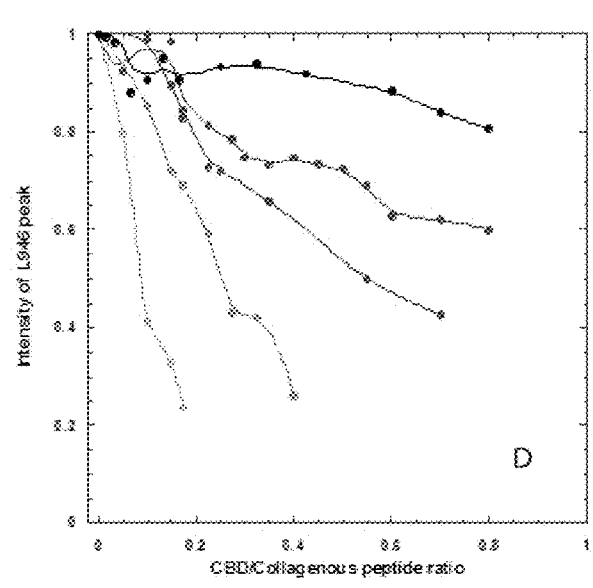
Figure 9A:
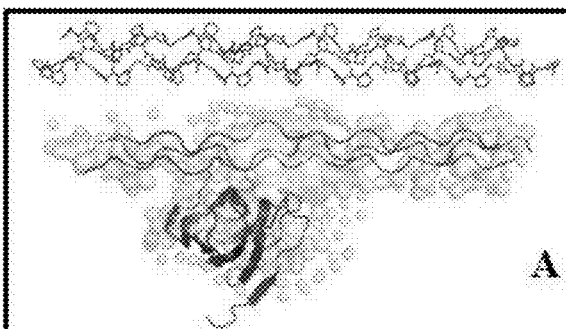
FIG. 9A-FIG. 9H are a set of structure drawings derived from SAXS scattering profiles using ab initio simulated annealing calculations for (FIG. 9A) [PROXYL-$(POG)_3POA(POG)_6]_3$:CBD complex, (FIG. 9B) [PROXYL-$(POG)_4POA(POG)_5]_3$:CBD complex, (FIG. 9C) [PROXYL-$(POG)_5POA(POG)_4]_3$:CBD complex and (FIG. 9D) [PROXYL-$(POG)_6POA(POG)_3]_3$:CBD complex, (FIG. 9E) $[(POG)_4POA(POG)_5C$-PROXYL$]_3$:CBD complex, (FIG. 9F) $[(POG)_4POA(POG)_5C$-carbamidomethyl$]_3$:CBD. The Gly→Ala mutation sites are highlighted.
Figure 9B:
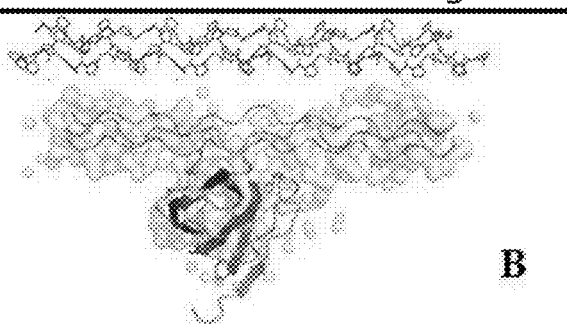
Figure 9C:
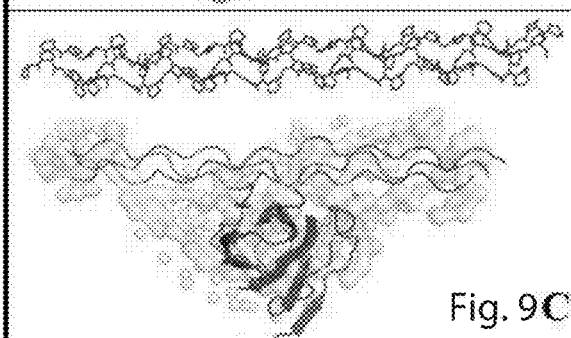
Figure 9D:
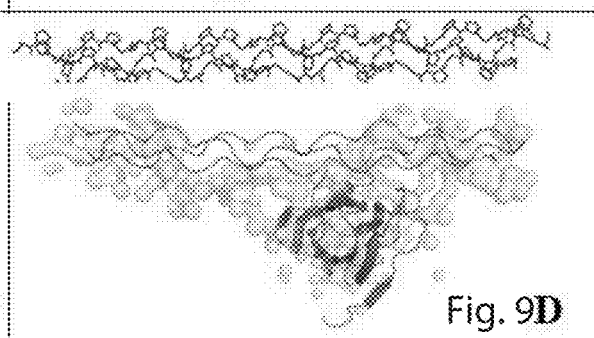
Figure 9E:
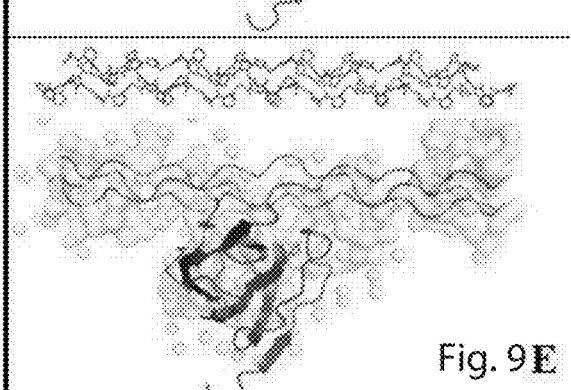
Figure 9F:
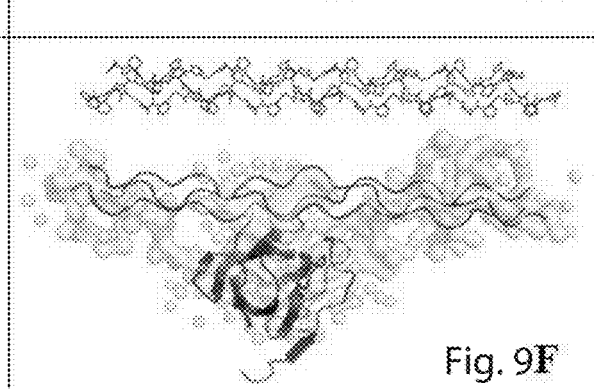

[(POG)$_4$POA(POG)$_5$]$_3$ (SEQ ID NO: 38), [(POG)$_4$POA (POG)$_5$C-carbamidomethyl]$_3$ (SEQ ID NO: 41), and [(POG)$_3$ PCG(POG)$_4$]$_3$ (SEQ ID NO: 40) that lack the PROXYL groups were synthesized, and NMR titrations were repeated (FIGS. 6F, 8C and 8G, respectively). The Small angle X-ray scattering experiments (SAXS): The three dimensional molecular shapes of the CBD-collagenous peptide complexes were constructed using SAXS measurements. The main advantage of SAXS measurements is that the experiments are performed in solution under near physiological conditions. In our previous work, these three dimensional molecular envelopes were used to demonstrate asymmetric binding of CBD to the C-terminal (POG)$_3$ (SEQ ID NO: 44) of mini-collagen. The molecular shapes were constructed for complexes of CBD and six different untwisted mini-collagen molecules. In all cases CBD bound to (POG)$_2$POA (SEQ ID NO: 45) region preferentially to C-terminal (POG)$_3$ (SEQ ID NO: 44) (FIGS. 9A-F). For example the docking model for CBD:[(POG)$_4$POA(POG)$_5$]$_3$ (SEQ ID NO: 38) constructed using the crystal structure of CBD (pdb accession code 1NQD) interacting with (POG)$_2$POA (SEQ ID NO: 45) region of the untwisted collagen (pdb accession code 1CAG) fit the envelope well (FIG. 9B). Although NMR results demonstrated that CBD also binds to the C-terminal (POG)$_3$ (SEQ ID NO: 44) of [(POG)$_4$POA(POG)$_5$-PROXYL]$_3$ (SEQ ID NO: 38), CBD predominantly binds to the (POG)$_2$POA (SEQ ID NO: 45) region of the peptide (FIGS. 9E and 9F).

Figure 9G:
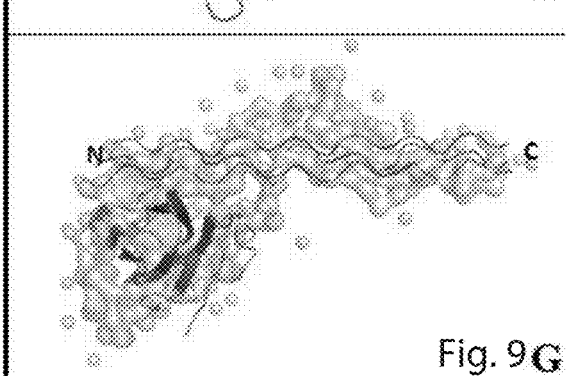
Figure 9H:
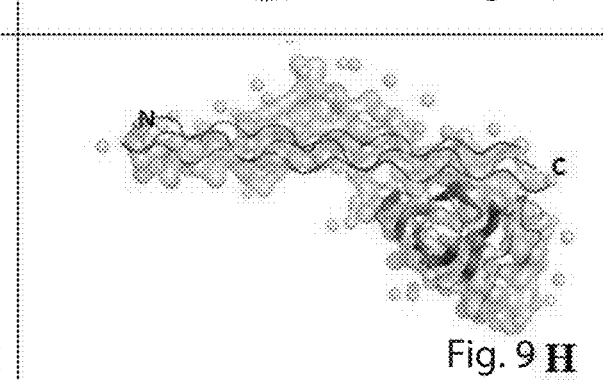
Figure 10A:
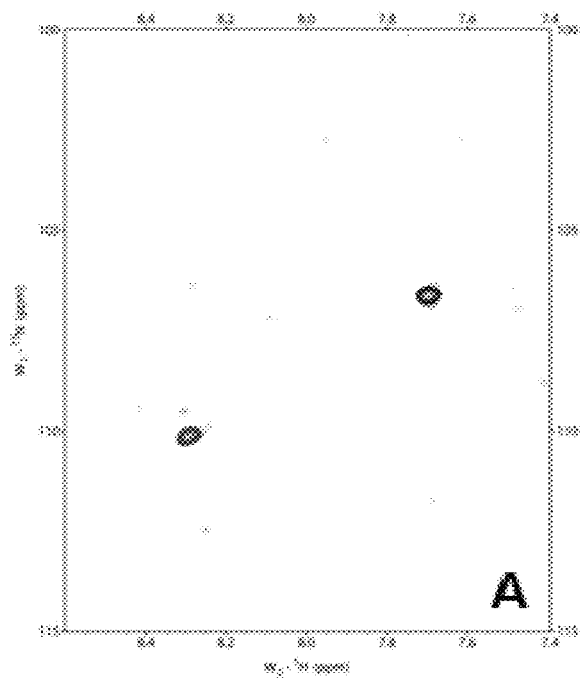
FIG. 10A to FIG. 10D are a set of plots showing HSQC NMR data obtained using the CBD—collagenous peptide interactions.
Figure 10B:
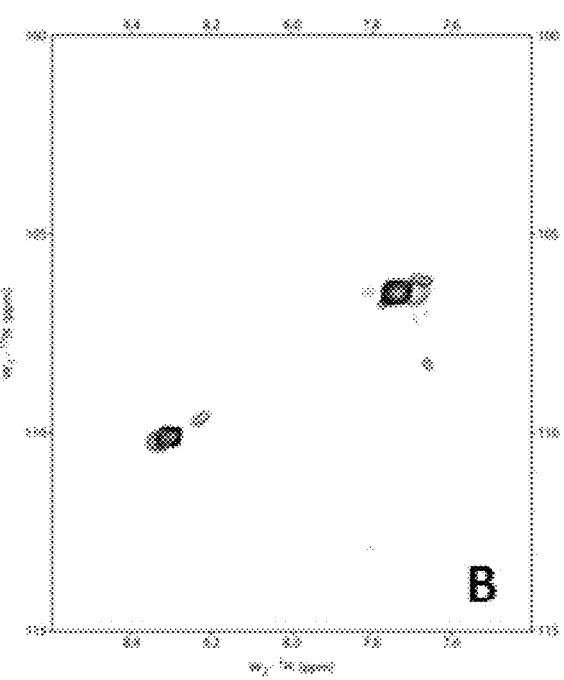
Figure 10C:
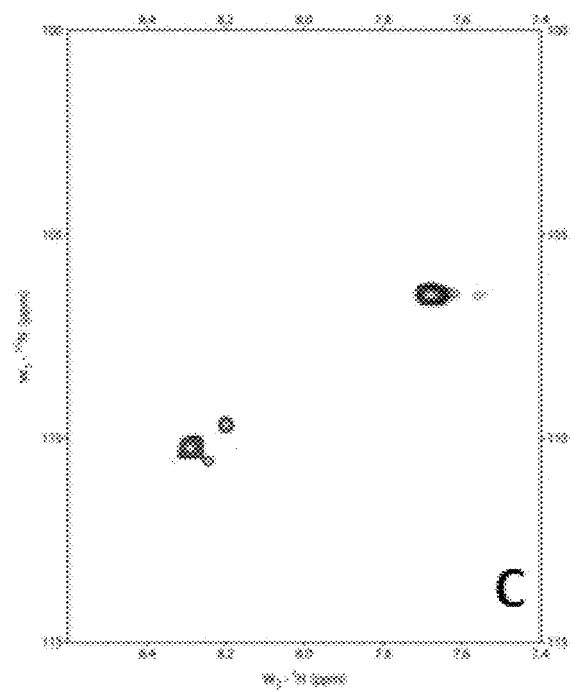
Figure 10D:
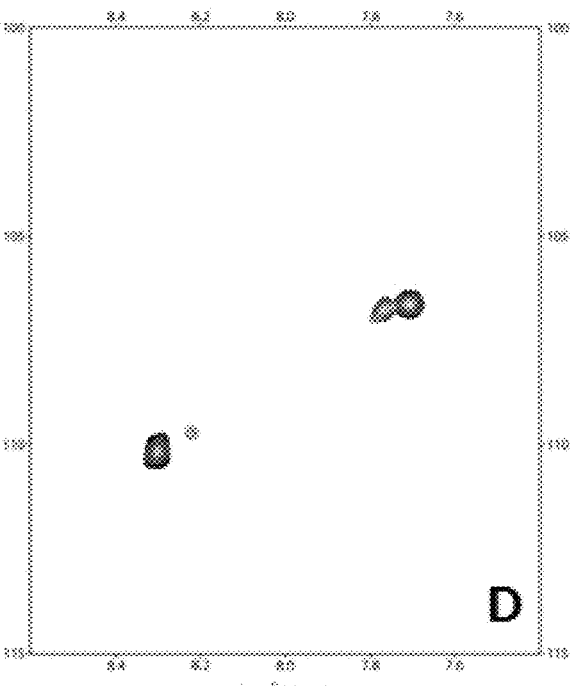

Structures derived from SAXS profiles using simulated annealing calculations for [11PROXYL-(POG)$_3$PCG (POG)$_4$]$_3$ (SEQ ID NO: 40) (FIGS. 9G and 9H) indicated an additional density that could be attributed to the PROXYL group. The SAXS derived three-dimensional shape of [11PROXYL-(POG)$_3$PCG(POG)$_4$]$_3$ (SEQ ID NO: 40):CBD complex superimposes well with either NMR derived complexes i.e., CBD binding to the N-terminal (POG)$_3$ (SEQ ID NO: 44) or to the C-terminal (POG)$_3$ (SEQ ID NO: 44) (FIGS. 9G and 9H).

Little structural change of $^{15}$N-minicollagen upon CBD binding: The studies thus far suggest that CBD scans the collagen fibril for under-twisted regions. Upon binding to the less structured regions, does it actively unwind collagen? Active unwinding by CBD would facilitate collagenolysis. To investigate two collagenous peptides selectively labeled with $^{15}$N near N- or near C-terminus of [(POG)$_{10}$]$_3$ (SEQ ID NO: 35) were synthesized (Table 4, peptides A,B), and the structural changes due to the binding of unlabeled CBD were monitored using $^1$H-$^{15}$N HSQC titration.

TABLE 4

| | $^{15}$N-Labeled Mini-collagen | SEQ ID NO: |
|---|---|---|
| A | POGPOG*POGPOGPOGPOGPOGPOGPOGPOG | 35 |
| B | POGPOGPOGPOGPOGPOGPOGPOGPOG*POG | 35 |
| C | POGPOG*POGPOGPOAPOGPOGPOGPOGPOG | 38 |
| D | POGPOGPOGPOGPOAPOGPOGPOGPOG*POG | 38 |

*indicates the $^{15}$N-labeled Glycine; A indicates Gly→Ala substitution.

The $^{15}$N-Gly labeled peptides exhibited two distinct cross peaks in the $^1$H-$^{15}$N HSQC spectrum (FIGS. 10A and 10B). Those cross peaks corresponded to unwound monomer and triple helical conformations assigned in earlier NMR studies. Liu, et al. (1996) *Biochemistry* 35, 4306-4313 and Li, et al. (1993) *Biochemistry* 32, 7377-7387. The Gly residue closer to the terminal triplets exhibits both monomer and trimer peaks in the HSQC spectrum, whereas the Gly residue in the middle of the triple helix exhibits a strong trimer cross peak. If CBD is to bend or to cause any unwinding of the triple helix upon binding, we expected the cross peak corresponding to the triple helix to line broaden and disappear on the course of titration, and the cross peak corresponding to the single chain to intensify. However during the course of the titration, CBD did not instigate any changes on the $^1$H-$^{15}$N HSQC spectra of the collagenous peptides. Thus CBD bound to C-terminal $(POG)_3$ (SEQ ID NO: 35) imposed little structural changes to the triple helix.

Untwisted mini-collagen molecule selectively labeled with $^{15}$N-Gly either at near the N- or C-termini (Table 4C and D) was titrated with unlabeled CBD. Cross peaks corresponding to monomer and triple-helix were identified on the HSQC spectra (FIGS. 10C and 10D). The titration of unlabeled CBD induced little change in the intensity of either monomer or trimer cross peak. Even upon binding to the partially unwound mini-collagen, CBD does not initiate any further unwinding.

CBD unidirectionally binds to the under-twisted site in the triple helical collagen. CBD may help disband the collagen fibril, but does not unwind the triple helix. Targeting under-twisted regions of tropocollagen may circumvent the energy barrier required for unwinding the triple helices. When CBD is used as a drug delivery molecule, the injected molecule distributes prominently to the end plates of vertebral discs, near the growth plates of tibia and fibula, and also to skin. It could be unloading its payload to the most blood accessible collagen that is undergoing remodeling, thus rich in under-twisted regions.

Example 2: Structural Comparison of ColH and ColG Collagen-Binding Domains

The C-terminal collagen-binding domain (CBD) of collagenase is required for insoluble collagen fibril binding and for subsequent collagenolysis. The high resolution crystal structures of ColG-CBD (s3b) and ColH-CBD (s3) the molecules resemble one another closely (r.m.s.d. $C_\alpha$=1.5 Å), despite sharing only 30% sequence identity. Five out of six residues chelating $Ca^{2+}$ are conserved. The dual $Ca^{2+}$ binding sites in s3 are completed by a functionally equivalent aspartate. The three most critical residues for collagen interaction in s3b are conserved in s3. The general shape of the binding pocket is retained by altered loop structures and side-chain positions. Small angle X-ray scattering data revealed that s3 also binds asymmetrically to mini-collagen. Besides the calcium-binding sites and the collagen-binding pocket, architecturally important hydrophobic residues and hydrogen-bonding network around the cis-peptide bond are well-conserved in metallopeptidase subfamily M9B.

Common structural features described above and in Bauer et al. (2012) J Bacteriol November 9 (which is incorporated herein by reference in its entirety), enabled us to update the sequence alignment of the CBD in the M9B subfamily (FIG. 1). Conserved residues are important for one of four reasons: calcium chelation (red), cis-trans isomerization of the linker (yellow), collagen-binding (blue) or protein folding (green). FIG. 1 also indicates the strands of the structure along the top of the figure.

The dual calcium-binding site is formed by four chelating residues (Glu899, Glu901, Asn903, and Asp904) within the N-terminal linker, two chelating residues (Asp927 and Asp930) from the β-strand C and invariant Tyr1002 hydrogen-bonds and orients Asp930. Residue numbers used in this paragraph are of s3b. Likewise other supporting cast such as Gly921 is conserved in the middle of β-strand strategically placed to make room for Glu899. The dual calcium chelation site is fashioned sometimes by functionally equivalent residues. As mentioned, Asp897 of s3 acts equivalently to Asp927 of s3b. Asp897 equivalents are tentatively identified in *B. brevis* s3a and s3b, *C. botulinum* A3 s3a and *C. histolyticum* ColG s3a. Tridentate and divalent Asp and Glu residues are conserved with only *C. sordellii* s3a as the exception. The monodentate Asp904 residue is sometimes substituted by Asn. For those substituted, the net charge of the dual calcium site is neutral rather than −1.

The peptide between residues 901-902 has cis conformation in the holo state for both s3b and s3. The position 902 in other CBD molecules is Pro, Asp or Asn. Pro frequently succeeds the peptide bond to ease trans-cis isomerization. The s3 molecule has Pro. In s3b, OD of Asn902 hydrogen-bonds with the main-chain N of Asp904. The hydrogen-bond is critical for the peptide isomerization. Spiriti and van der Vaart. (2010) Biochemistry 49:5314-5320, which is incorporated herein by reference in its entirety. For the remainder of CBD molecules with Asp at the position, OD of Asp could play the same role as that of Asn902. Other hydrogen-bonds identified by simulation studies important in stabilizing the transition states are well conserved. These donor-acceptor pairs in s3 and s3b are tabulated (Table 5). Calcium ions could catalyze the isomerization in all the CBD molecules and their transition states and catalytic mechanism may look very similar.

TABLE 5

Hydrogen-bonds important in trans-cis peptide isomerization in s3b and their counterparts in s3.

| Important H-bonds in s3b for transition state formation | Corresponding H-bonds in s3 |
| --- | --- |
| T910_OG1 . . . N903_NH2 | S879_OG1 . . . N872_ND2 |
| T910_OG1 . . . N900_N | S879_OG1 . . . K86_N |
| E899_OE1 . . . N903_ND2 | E868_OE1 . . . N872_ND2 |
| E899_OE2 . . . S922_N | E868_OE2 . . . T891_N |
| N902_OD1 . . . D904_N | NA (N902 replaced with P871) |
| D930_OD2 . . . Y1002_OH | D939_OD2 . . . Y97_OH |
| Y1002_OH . . . Y932_OH | NA (Y932 replaced with F901) |

Non-functional residues that are important in either folding or architectural stability are conserved. Hydrophobic residues packed between the β-sheets are better conserved if they are located in the vicinity of functionally critical residues. For example, invariant Trp956 of strand E is packed between the β-sheets. The residues flanking (Thr955 & Thr957) interact with mini-collagen. Tyr932 is packed between the sheets and helps positioning Tyr1002. Residues at tight turns are conserved as well. Gly975 is well conserved to allow a type II' turn in s3b. Gly942 (Gly975 equivalent) in s3 allows Asp941 side-chain to stabilize the reverse turn. A highly conserved six-residue stretch, between residues 986 and 991, adopts a tight turn and precedes the functionally important strand H. The region is well ordered in the crystal structures with low B-factors, and is the least dynamic based on NMR and limited proteolysis MALDI-TOF MS (25). Philominathan, et al. (2009) J Biol Chem 284:10868-10876 and Sides et al. J Am Soc Mass Spectrom. (2012) 23(3):505-19 both of which are incorporated herein by reference in their entireties. The main-chain carbonyl and amino groups of Arg985 hydrogen-bond with OH of Tyr989 to stabilize the turn. Only Gly987 can make room for the bulky Tyr989 side chain. Tyr990 packs against the invariant Ala909 and conserved $3_{10}$ helix. Ala909 is at the base of the linker that undergoes α-helix→β-strand transformation. The tight turn may ensure that collagen interacting Leu992, Tyr994, and Tyr996 would be correctly positioned. Tyr994 is the most critical residue in interacting with collagenous peptides. Wilson, et al. (2003) EMBO J 22:1743-1752. The strands adjacent to strand H, i.e. strands C and E, are very well conserved. The three antiparallel strands mold the collagen-binding pocket. Strand F staples the β-sheets by interacting with both sheets. The β-strand first interacts in an antiparallel orientation with strand E then breaks its direction at Gly971 to interact with strand G. In place of Gly971, Ala or Pro is found at the location where the strand switches its allegiance. The dual interaction of the strand helps positioning Tyr970 to interact with mini-collagen.

Three residues shown to interact strongly with mini-collagen are conserved. The invariant Tyr994 and well conserved Tyr970 and Tyr996 constitute the "hot spot". Y994A mutation lost binding capability. Since Y994F resulted in 12-fold reduction in binding to mini-collagen, the hydroxyl group of Tyr994 may interact with collagen through a hydrogen-bond. Tyr996, which is a critical residue in binding mini-collagen, is not so well conserved. Y996A caused 40-fold reduction in binding to the mini-collagen. Y996 is s3b is replaced with Phe in s3, though both side chains have identical orientation. In other CBD molecules, an aromatic residue, such as Phe or His, is sometimes found at the site. Y970A results in 12-fold reduction in binding to mini-collagen. Thr957 was found to interact with mini-collagen by $^{15}$N-HSQC-NMR titration. The β-branched amino acid residues or Leu are found at the positions equivalent to Thr957 in most of the CBDs. Six other residues were identified by $^{15}$N-HSQC-NMR titration to interact with mini-collagen are not very well conserved. Since divergent CBDs (s3 and s3b) adopted a similar saddle-shaped binding pocket, other CBDs may also adopt similar collagen-binding strategy.

Divergent CBD could target different collagen sequences and could possibly target different collagen types; however, this structural study suggest otherwise. Rather, all the CBD domains may bind similarly to an under-twisted region such as the C-terminus of a collagen fibril. The C-terminus of type I collagen is exposed in the fibril surface based on X-ray fiber diffraction experiments, and it is the most accessible site for the bacterial collagenase to initiate assaults. However CBD binding only at the C-terminal region of tropo-collagen is unfounded. Gold particle-labeled tandem ColG-CBD (s3a-s3b) labeled with gold particle bound to type I collagen fibrils exhibited no periodicity. In the collagen fibrils, the molecules are staggered from each other by about 67 nm. Therefore CBD could target partially under-twisted regions in the middle of a tropocollagen that are also vulnerable for assaults.

Much like s3b, s3 is both compact, and extremely stable in the presence of physiological $Ca^{2+}$. Thus, the enzyme could degrade extracellular matrix for prolonged time. The linker that induced structural transformation is a common feature found in M9B collagenase. It could act as $Ca^{2+}$ sensor to trigger domain rearrangement as means of enzyme activation. $Ca^{2+}$ concentration in extracellular matrix is higher than that inside a bacterium. Both s3 and s3b bind similarly to a mini-collagen, thus M9B collagenase molecules could initiate collagenolysis from analogous structural features in various collagen fibril. Fusion protein of any CBD derived from M9B collagenase and a growth factor should result in comparable clinical outcome.

Example 3: CBD-PTH Agonist Spurs Hair Growth and CBD-PTH Antagonist Inhibits Hair Growth In-Vitro Characterization of CBD-Linked PTH Compounds: Collagen binding of each peptide was verified in flow-through collagen binding assays as previously described in U.S. Patent Publication No. 2010/0129341, which is incorporated herein by reference in its entirety. PTH-CBD, consisting of the first 33 amino acids of PTH linked directly to the collagen binding domain (SEQ ID NO:

1), was the most potent agonist, having a similar effect to that of PTH(1-34) (SEQ ID NO: 7) on cAMP accumulation. Ponnapakkam et al. (2011) Calcif 88:511-520. Epub 2011 April 2022. Among the antagonists, PTH(7-33)-CBD (SEQ ID NO: 10) had the best combination of low intrinsic activity and high receptor blockade (not shown), similar to those seen in other PTH antagonists, including those used in hair growth studies. Peters, et al. (2001) J Invest Dermatol 117:173-178.

Figure 11:
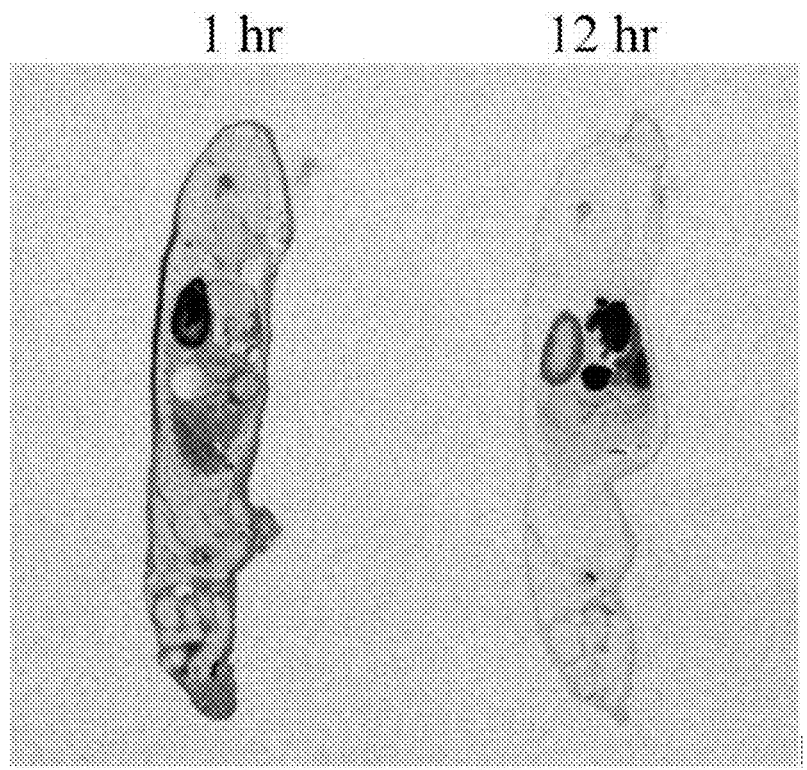
FIG. 11 shows the tissue distribution of $S^{35}$-PTH-CBD 1 hour and 12 hours after subcutaneous injection. Note the skin outline.

In-Vivo Distribution of PTH-CBD: Tissue distribution was assessed by administering $^{35}$S-labelled PTH-CBD via subcutaneous injection, followed by whole mount frozen and whole-body autoradiography. PTH-CBD with a phosphorylation site between PTH(1-33) and the CBD was purified, activated and labeled with [gamma-35] ATP as described previously. Tamai et al. (2003) Infect Immun. 71:5371-5375. Approximately 10.8 mcg of $^{35}$S-PTH-CBD (122 kcm/mcg) was injected subcutaneously in 7 week-old mice (32-35 g). Mice were sacrificed at 1 hour or 12 hours post-injection, and then frozen in dry ice-acetone. Frozen sections (50 µm) were prepared with an autocryotome, dried at −20° C., and exposed to an image plate for 4 weeks. There appeared to be an initial distribution of $^{35}$S-PTH-CBD to a broad area of skin around the site of injection, followed by a rapid redistribution to the skin of the entire animal, as well as to several other tissues (i.e. bone, intestine, bladder) (FIG. 11). PTH-CBD thus showed the desired properties of distribution and retention to skin with subcutaneous administration.

PTH-CBD Reverses Hair Loss in Chemotherapy-induced Alopecia in Mice: We compared efficacy of CBD linked PTH agonists and antagonists in chemotherapy-induced alopecia, utilizing an experimental design published by Peters, et al., for non-CBD linked PTH compounds. Peters, et al. (2001) J Invest Dermatol 117:173-178. C57BL/6J mice (Jackson Laboratories, Bar Harbor, Me.) were depilated to synchronize the hair follicles, and cyclophosphamide (CYP, 150 mg/kg) was administered on day 9 to maximize the chemotherapy-induced damage. The agonist (PTH-CBD) and the antagonist (PTH(7-33)-CBD) were administered 2 days prior to chemotherapy, and given the long-term retention of the compounds in the skin, we administered only a single dose to cover the timing of the multiple injections of PTH agonist and antagonist in the study by Peters, et. al. The administered dose of CBD-linked compounds (320 mcg/kg) is well tolerated in mice. Ponnapakkam et al. (2011) Calcif 88:511-520. Epub 2011 April 2022.

Figure 12:
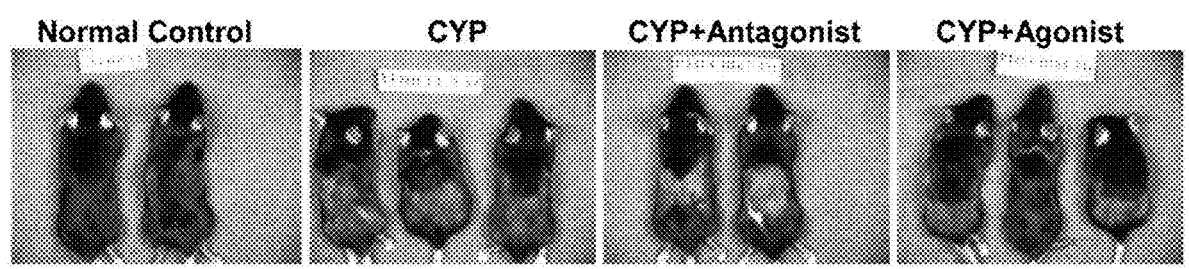
FIG. 12 is a set of photographs documenting the hair growth on the back of mice at day 36 after depilation, treatment groups as indicated (Antagonist=PTH(7-33)-CBD, Agonist=PTH-CBD).
Figure 14:
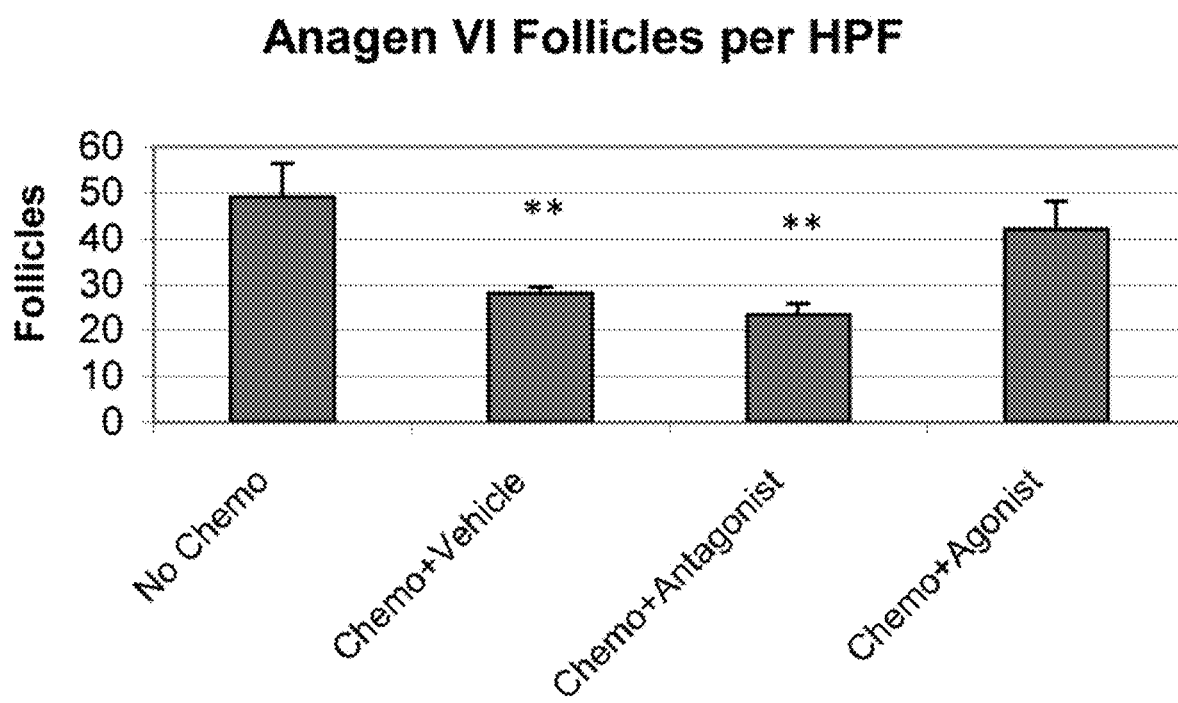
FIG. 14 is a graph showing the hair follicle counts per high powered field. Anagen VI hair follicles were counted by two independent observers in a blinded fashion. Results are expressed as mean+/−standard deviation. **=p<0.01 vs. no chemo ANOVA followed by Dunnett's test. (Antagonist=PTH(7-33)-CBD, Agonist=PTH-CBD).

The results of the photodocumentation record indicate that the agonist, PTH-CBD, was far more effective at stimulating hair growth than was the antagonist (FIG. 12). Histological examination revealed morphological changes in the hair follicles after CYP therapy, which were more superficially located and exhibited clumped melanocytes around the bulb, characteristics of the dystrophic anagen and catagen phase (FIG. 13). While the antagonist PTH(7-33)-CBD had no beneficial effect, treatment with the agonist PTH-CBD led to deeper rooting and reduced melanocyte clumping, thus reversing the dystrophic changes. Counts of anagen VI hair follicles per high-powered field (HPF) were compared between groups; animals treated with PTH-CBD had a higher number of hair follicles, approaching those of animals which did not receive chemotherapy (FIG. 14), while the antagonist PTH(7-33)-CBD had no beneficial effect.

Importantly, we saw no evidence of adverse effects from PTH-CBD administration. While PTH injections are known to elevate blood calcium and can cause kidney stones, PTH-CBD had no effect on serum calcium. In addition, there was no evidence of excess hair length on the body or of excess hair growth on the ears and tail, where a full coat is normally not present. The effects of PTH-CBD on hair growth have been confirmed in models of chemotherapy-induced alopecia without depilation, which more closely mimic clinical protocols.

Quantification of Effects of PTH-CBD in Chemotherapy-induced Alopecia: We followed these studies by comparing the effects of different doses of PTH-CBD in chemotherapy-induced alopecia. In these studies, we applied the injections more distally on the back and applied a gray-scale analysis to quantify the amount of hair growth. Injecting more distally in the back allows us to compare regrowth of hair after PTH-CBD treatment with less interference from the normal hair regrowth, which normally proceeds from head to tail in mice. The results are shown in FIG. 15, indicating a dose-dependent effect on hair regrowth both qualitatively and quantitatively.

Figure 16:
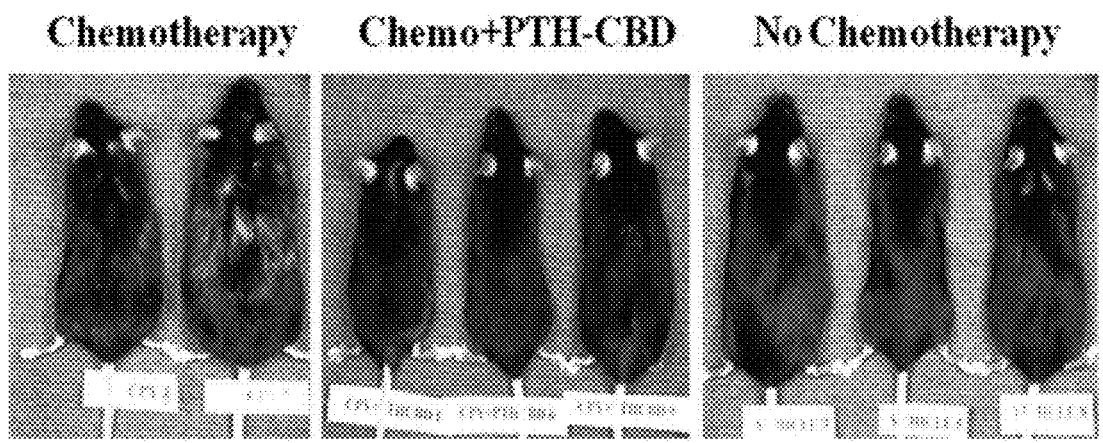
FIG. 16 is a set of photographs showing the hair on the back of mice after the indicated treatment without prior depilation.

Chemotherapy-induced Alopecia without Depilation: While the depilated model of chemotherapy-induced alopecia provides a uniform model for comparison of drug effects, the depilation process is known to cause hair follicle injury, and may alter the response of the animals to the PTH-CBD administration. We therefore tested the effects of PTH-CBD in another model of chemotherapy-induced alopecia, where the animals were given 3 courses of cyclophosphamide therapy (50 mg/kg/wk), similar to the usual manner in which cancer patients might be treated. In this model, it takes much longer (4-6 months) for alopecia to develop. Animals that received a single dose of PTH-CBD (320 mcg/kg subcutaneous) prior to the first cycle did not develop hair loss as shown in FIG. 16.

In a second study, we compared the effects of PTH-CBD when given prophylactically, at the time of the first cycle of chemotherapy, vs. therapeutically, after the hair loss had developed. While PTH-CBD was effective in both instances, the effects were more prominent when given prophylactically. This is evident both visually and quantitatively in FIG. 17, using the same grey scale analysis used in our dose-response study.

Figure 18:
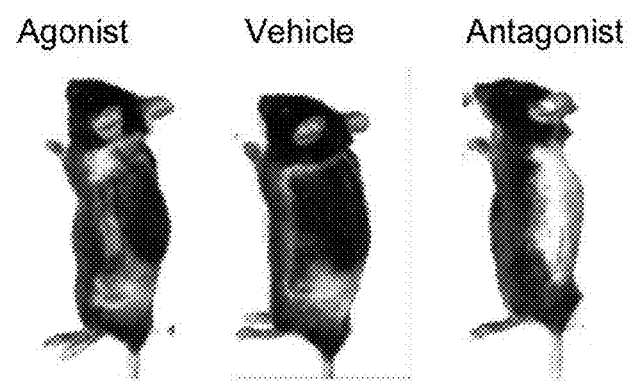
FIG. 18 is a photograph of three mice 13 days after waxing to remove hair and treatment with PTH-CBD, PTH antagonist-CBD or vehicle alone.

Depilation Alopecia: The agonist PTH-CBD appears to increase hair growth by increasing the number of anagen phase hair follicles. As such, there is no reason to believe that hair growth effects should be limited to the chemotherapy model. We therefore tested both PTH-CBD and antagonist compound, PTH(7-33)-CBD, after removing hair from C57/BL6J mice by waxing (FIG. 18). The results were quite interesting; agonist (PTH-CBD) treated animals had earlier anagen eruption (day 7 vs. day 9 for vehicle controls), and exhibited more complete regrowth of hair by the end of the study (day 18). Antagonist (PTH(7-33)-CBD) treated animals also had an early anagen eruption, but the hair growth which followed was markedly curtailed, and the hair cycle was arrested after this point, resulting no further observed regrowth of hair. Thus, it appears that agonist therapy is acting to promote more rapid regrowth of hair by promoting more rapid transition to the anagen phase, while the antagonist inhibited hair regrowth by blocking this transition.

PTH-CBD is a fusion protein of the first 33 amino acids of parathyroid hormone (PTH) and a bacterial collagen binding domain. The collagen binding activity causes PTH-CBD to be retained at its site of action in the dermal collagen, maximizing efficacy and reducing systemic side-effects. PTH-CBD stimulates hair growth by causing hair follicles to enter an anagen VI or growth phase, presumably by activating WNT signaling and increasing production of beta-catenin. We therefore plan to conduct the following additional studies to confirm this mechanism of action and to determine the effect of PTH-CBD in two distinct genetic mouse models with WNT signaling inhibition. These data will be used in formulating clinical trials for PTH-CBD as a therapy for alopecia.

Figure 19:
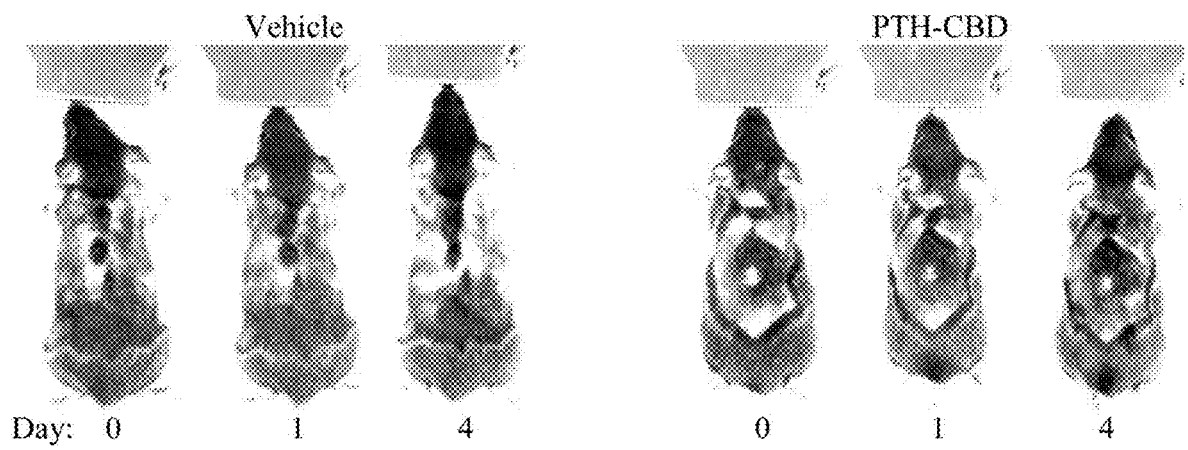
FIG. 19 is a set of photographs of mice showing hair regrowth in a model of alopecia areata after treatment with a control or with PTH-CBD.
Figure 20:
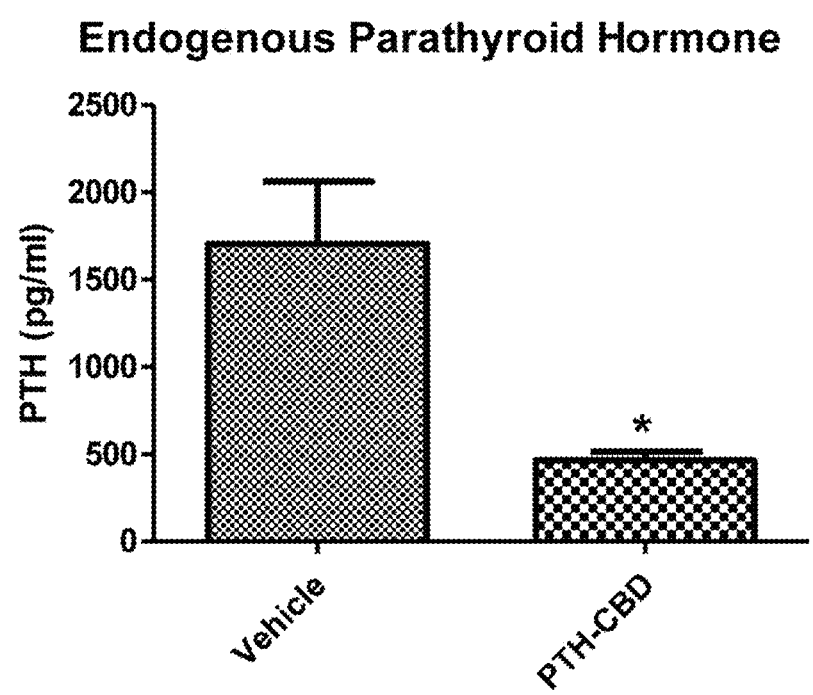
FIG. 20 is a graph showing the endogenous parathyroid hormone levels in ovarectomized aged rats injected with a single dose of human PTH-CBD 6 months prior to sacrifice.

Alopecia Areata: Alopecia Areata is a disease of patchy hair loss due to autoimmune destruction of the hair follicles. We tested the efficacy of PTH-CBD in promoting regrowth of hair in an animal model of alopecia areata, the engrafted C3H/Hej mouse. In this model, hair loss develops variably over the first 2 months of life. Shown in FIG. 19 is the results of a single dose of PTH-CBD (320 mcg/kg subcutaneous) administered into the engrafted site, the center of the back, where there was maximal hair loss. Compared to vehicle control animals, which continued to lose hair at this site, animals receiving PTH-CBD began to show regrowth of hair within the next 1-4 days. Importantly, the response was found to be sustained during the 2 month course of the experiment.

Example 4: CBD-PTH Can Prevent or Treat Hyperparathyroidism

In this experiment, rats had their ovaries surgically removed at age 3 months. At age 9 months, rats were injected with either a single dose of PTH-CBD (320 mcg/kg) or vehicle control. Animals were sacrificed 6 months after therapy (age 15 months). Human intact PTH levels were measured to assess serum levels of PTH-CBD, and were found to be undetectable in both groups. Serum calcium was measured and there were no differences between groups (Vehicle: 13.5+/−1.1 vs. PTH-CBD: 14.3+/−1.1 mg/dl, NS). Rat intact PTH levels were measured to assess endogenous PTH production, and PTH-CBD suppressed the normal increase in endogenous PTH levels seen in aged, ovarectomized rats. These findings indicate that a single injection of PTH-CBD can provide long-term suppression of endogenous PTH production, preventing the normal rise seen with age in the ovarectomized rat model, and thus may serve as a therapy for hyperparathyroidism.

We claim:

1. A method of treating a subject having a collagenopathy, the method comprising:
   a) selecting a subject in need of treatment for a collagenopathy selected from the group consisting of osteogenesis imperfecta, Stickler's syndrome, Ehlers-Danlos syndrome, Alport's syndrome, and Caffey's disease; and
   b) administering a composition comprising a bacterial collagen-binding polypeptide segment linked to a PTH/PTHrP receptor agonist to the subject;
      wherein the bacterial collagen-binding polypeptide segment delivers the agent to sites of partially untwisted or under-twisted collagen, wherein the bacterial collagen-binding polypeptide segment comprises a collagen-binding polypeptide derived from an M9 peptidase selected from the group consisting of Clostridium, Bacillus and Vibrio, one of SEQ ID NOs: 13-34 or a fragment thereof, residues 34-158 of SEQ ID NO: 1, a fragment of at least 8 consecutive amino acids from residues 34-158 of SEQ ID NO: 1, or a peptide that is at least 90% identical to residues 34-158 of SEQ ID NO: 1 or SEQ ID NOs: 13-34.

2. The method of claim 1, wherein the PTH/PTHrP receptor agonist comprises residues 1-33 of SEQ ID NO: 1, PTH (SEQ ID NO: 7), residues 1-14 of SEQ ID NO: 1, residues 1-34 of SEQ ID NO: 7 or a fragment of at least 8 consecutive amino acids from residues 1-34 of SEQ ID NO: 7.

3. The method of claim 1, wherein the composition has at least 50% greater activity in the subject than PTH(1-34) administered alone.

4. The method of claim 1, further comprising administering a therapeutic agent, wherein the therapeutic agent is an agent capable of promoting bone growth, decreasing inflammation, or promoting collagen stability.

5. The method of claim 4, wherein the therapeutic agent is selected from the group consisting of BMP-2, BMP-3, FGF-2, FGF-4, anti-sclerostin antibody, growth hormone, IGF-1, VEGF, TGF-b, KGF, FGF-10, TGF-α, TGF-β1, TGF-β receptor, GM-CSF, EGF, PDGF and connective tissue growth factors.

6. The method of claim 1, wherein the collagen-binding polypeptide segment and the PTH/PTHrP receptor agonist are chemically cross-linked to each other or are polypeptide portions of a fusion protein.

7. The method of claim 1, wherein the PTH/PTHrP receptor agonist is a polypeptide and the N-terminus of the collagen-binding polypeptide segment is linked directly or through a linker polypeptide segment to the C-terminus of the PTH/PTHrP receptor agonist polypeptide.

8. The method of claim 1, wherein the composition has at least 50% greater activity in the subject than the PTH/PTHrP receptor agonist administered alone.

9. The method of claim 1, wherein the composition is administered intramuscularly, intradermally, intravenously, subcutaneously, intraperitoneally, topically, orally, parenteral, or intranasally.

10. The method of claim 1, wherein the subject is a human.

11. The method of claim 1, wherein the composition is administered in aqueous solution at pH below about 5.0.

12. The method of claim 1, wherein the composition is administered in aqueous solution at pH above about 6.0.

13. The method of claim 7, wherein the linker polypeptide includes a polycystic kidney disease (PKD) domain.

14. The method of claim 13, wherein the PKD domain comprises residues 807-901 of SEQ ID NO: 6.

15. The method of claim 1, wherein the collagen-binding polypeptide includes residues 894-1008, 894-1021, 901-1021, or 901-1008 of SEQ ID NO: 6 or a homolog thereof.

16. The method of claim 7, wherein collagen binding polypeptide includes residues 37-251 of SEQ ID NO: 2 or residues 807-1021 of SEQ ID NO: 6.

17. The method of claim 1, wherein the collagen binding polypeptide comprises residues 34-158 of SEQ ID NO: 1.

18. The method of claim 1, wherein the collagen binding polypeptide comprises a peptide that is at least 90% identical to one of SEQ ID NOs: 13-34.

19. The method of claim 1, wherein the collagen binding polypeptide is a peptide that is at least 90% identical to residues 34-158 of SEQ ID NO: 1.

* * * * *